(12) United States Patent
Fischer et al.

(10) Patent No.: US 10,036,010 B2
(45) Date of Patent: Jul. 31, 2018

(54) RECOGNITION TAGS FOR TGASE-MEDIATED CONJUGATION

(71) Applicants: Innate Pharma, Marseilles (FR); Paul Scherrer Institut, Villigen PSI (CH)

(72) Inventors: Eliane Fischer, Eglisau (CH); François Romagne, Marseilles (FR); Patrick Dennler, Wettingen (CH)

(73) Assignees: INNATE PHARMA, Marseilles (FR); PAUL SCHERRER INSTITUT, Psi (CH)

( * ) Notice: Subject to any disclaimer, the term of this patent is extended or adjusted under 35 U.S.C. 154(b) by 205 days.

(21) Appl. No.: 14/441,157

(22) PCT Filed: Nov. 8, 2013

(86) PCT No.: PCT/EP2013/073428
§ 371 (c)(1),
(2) Date: May 6, 2015

(87) PCT Pub. No.: WO2014/072482
PCT Pub. Date: May 15, 2014

(65) Prior Publication Data
US 2015/0284713 A1 Oct. 8, 2015

Related U.S. Application Data

(60) Provisional application No. 61/724,414, filed on Nov. 9, 2012.

(51) Int. Cl.
*C40B 40/10* (2006.01)
*C12N 15/10* (2006.01)
(Continued)

(52) U.S. Cl.
CPC ...... *C12N 15/1065* (2013.01); *A61K 47/6889* (2017.08); *A61K 47/6898* (2017.08);
(Continued)

(58) Field of Classification Search
None
See application file for complete search history.

(56) References Cited

U.S. PATENT DOCUMENTS 4,741,900 A 5/1988 Alvarez et al.
4,816,567 A 3/1989 Cabilly et al.
(Continued)

FOREIGN PATENT DOCUMENTS

DE 19907588 A1 8/2000
EP 0555649 A2 8/1993
(Continued)

OTHER PUBLICATIONS

Altschul et al., "Gapped BLAST and PSI-BLAST: A new generation of protein database search programs", Nucl Acids Res. (1997) 25(17): 3389-3402.
(Continued)

*Primary Examiner* — Christian C Boesen
(74) *Attorney, Agent, or Firm* — Knobbe Martens Olson & Bear LLP

(57) ABSTRACT

The present application relates to methods for the functionalization of antibodies using transglutaminase, in particular antibodies lacking Fc regions. Also disclosed herein are peptide tags for transglutaminase, linking reagents, functionalized antibodies, multi-specific antibodies, pharmaceutical compositions, and method of treating disease and/or conditions.

8 Claims, 18 Drawing Sheets

(51) Int. Cl.
  B82Y 5/00 (2011.01)
  A61K 47/68 (2017.01)
(52) U.S. Cl.
  CPC ............ B82Y 5/00 (2013.01); C12N 15/1037 (2013.01); *C07K 2317/22* (2013.01); *C07K 2317/569* (2013.01); *C07K 2317/622* (2013.01); *C07K 2318/00* (2013.01); *C07K 2318/20* (2013.01); *C07K 2319/41* (2013.01); *C07K 2319/70* (2013.01); *C07K 2319/90* (2013.01); *C40B 40/10* (2013.01)

(56) References Cited

U.S. PATENT DOCUMENTS

| | | |
|---|---|---|
| 5,156,956 A | 10/1992 | Motoki et al. |
| 5,225,539 A | 7/1993 | Winter |
| 5,229,275 A | 7/1993 | Goroff |
| 5,252,469 A | 10/1993 | Andou et al. |
| 5,530,101 A | 6/1996 | Queen et al. |
| 5,565,332 A | 10/1996 | Hoogenboom et al. |
| 5,567,610 A | 10/1996 | Borrebaeck |
| 5,573,905 A | 11/1996 | Lerner et al. |
| 5,585,089 A | 12/1996 | Queen et al. |
| 5,693,761 A | 12/1997 | Queen et al. |
| 5,693,762 A | 12/1997 | Queen et al. |
| 5,712,120 A | 1/1998 | Rodriguez et al. |
| 5,714,350 A | 2/1998 | Co et al. |
| 5,731,183 A | 3/1998 | Kobayashi et al. |
| 5,736,356 A | 4/1998 | Sano et al. |
| 5,766,886 A | 6/1998 | Studnicka et al. |
| 5,770,196 A | 6/1998 | Studnicka |
| 5,777,085 A | 7/1998 | Co et al. |
| 5,821,123 A | 10/1998 | Studnicka |
| 5,821,337 A | 10/1998 | Carter et al. |
| 5,869,619 A | 2/1999 | Studnicka |
| 5,877,293 A | 3/1999 | Adair et al. |
| 5,886,152 A | 3/1999 | Nakatani et al. |
| 5,895,205 A | 4/1999 | Werner et al. |
| 5,929,212 A | 7/1999 | Jolliffe et al. |
| 6,054,297 A | 4/2000 | Carter et al. |
| 6,162,963 A | 12/2000 | Kucherlapati et al. |
| 6,180,370 B1 | 1/2001 | Queen et al. |
| 6,204,388 B1 | 3/2001 | Danishefsky et al. |
| 6,380,394 B1 | 4/2002 | Nicolaou et al. |
| 6,387,927 B1 | 5/2002 | Altmann et al. |
| 6,407,213 B1 | 6/2002 | Carter et al. |
| 6,548,640 B1 | 4/2003 | Winter |
| 6,632,927 B2 | 10/2003 | Adair et al. |
| 6,639,055 B1 | 10/2003 | Carter et al. |
| 6,750,325 B1 | 6/2004 | Jolliffe et al. |
| 6,797,492 B2 | 9/2004 | Daugherty et al. |
| 6,881,557 B2 | 4/2005 | Foote |
| 7,087,409 B2 | 8/2006 | Barbas, III et al. |
| 7,090,843 B1 | 8/2006 | Francisco et al. |
| 7,117,096 B2 | 10/2006 | Luo et al. |
| 7,135,174 B2 | 11/2006 | Corvalan et al. |
| 7,338,933 B2 | 3/2008 | DeFrees et al. |
| 7,378,091 B2 | 5/2008 | Gudas et al. |
| 7,393,648 B2 | 7/2008 | Rother et al. |
| 7,498,298 B2 | 3/2009 | Doronina et al. |
| 7,657,380 B2 | 2/2010 | Lazar et al. |
| 7,659,241 B2 | 2/2010 | Senter et al. |
| 7,763,736 B2 | 7/2010 | Sharpless et al. |
| 7,807,619 B2 | 10/2010 | Bertozzi et al. |
| 7,981,843 B2 | 7/2011 | Flynn et al. |
| 8,133,515 B2 | 3/2012 | Boons et al. |
| 9,340,615 B2 | 5/2016 | Maeda et al. |
| 9,427,478 B2 | 8/2016 | Bregeon et al. |
| 9,676,871 B2 | 6/2017 | Strop et al. |
| 9,717,803 B2 | 8/2017 | Bregeon et al. |
| 9,764,038 B2 | 9/2017 | Dennler et al. |
| 2002/0034765 A1 | 3/2002 | Daugherty et al. |
| 2002/0052028 A1 | 5/2002 | Santi et al. |
| 2002/0058286 A1 | 5/2002 | Danishefsky et al. |
| 2002/0062030 A1 | 5/2002 | White et al. |
| 2002/0102208 A1 | 8/2002 | Chinn et al. |
| 2002/0161201 A1 | 10/2002 | Filpula et al. |
| 2003/0153043 A1 | 8/2003 | Carr et al. |
| 2004/0253645 A1 | 12/2004 | Daugherty et al. |
| 2005/0026263 A1 | 2/2005 | Meares et al. |
| 2005/0238646 A1 | 10/2005 | Ledbetter et al. |
| 2005/0238649 A1 | 10/2005 | Doronina et al. |
| 2005/0256030 A1 | 11/2005 | Feng |
| 2006/0073137 A1 | 4/2006 | Adair et al. |
| 2006/0116422 A1 | 6/2006 | de Groot et al. |
| 2007/0122408 A1 | 5/2007 | Barbas, III et al. |
| 2008/0038260 A1 | 2/2008 | Ponath et al. |
| 2009/0028856 A1 | 1/2009 | Chen et al. |
| 2010/0004431 A1 | 1/2010 | Bernett et al. |
| 2011/0184147 A1 | 7/2011 | Kamiya et al. |
| 2011/0256157 A1 | 10/2011 | Howard et al. |
| 2011/0305631 A1 | 12/2011 | Govindan et al. |
| 2012/0322686 A1 | 12/2012 | Lyon et al. |
| 2013/0122020 A1 | 5/2013 | Liu et al. |
| 2013/0189287 A1 | 7/2013 | Bregeon et al. |
| 2013/0230543 A1* | 9/2013 | Pons ............... A61K 47/48369 424/178.1 |
| 2014/0088089 A1 | 3/2014 | Chari |
| 2014/0356385 A1 | 12/2014 | Dennler et al. |
| 2015/0346195 A1 | 12/2015 | Belmant et al. |
| 2016/0022833 A1 | 1/2016 | Bregeon et al. |
| 2016/0114056 A1 | 4/2016 | Bregeon et al. |
| 2016/0331842 A1 | 11/2016 | Bregeon et al. |
| 2017/0313787 A1 | 11/2017 | Strop et al. |

FOREIGN PATENT DOCUMENTS

| | | |
|---|---|---|
| EP | 1859811 A1 | 11/2007 |
| JP | 2003199569 A | 7/2003 |
| WO | WO 1992/02190 | 1/1992 |
| WO | WO 1992/11018 | 7/1992 |
| WO | WO 1992/22583 | 12/1992 |
| WO | WO 1993/10102 | 5/1993 |
| WO | WO 1996/06931 | 3/1996 |
| WO | WO 1996/22366 | 7/1996 |
| WO | WO 1998/25929 A1 | 6/1998 |
| WO | WO 1999/02514 A2 | 1/1999 |
| WO | WO 1999/07692 A2 | 2/1999 |
| WO | WO 1999/58534 A2 | 11/1999 |
| WO | WO 1999/67252 A2 | 12/1999 |
| WO | WO 1999/67253 A2 | 12/1999 |
| WO | WO 2000/000485 A1 | 1/2000 |
| WO | WO 2000/037473 A1 | 6/2000 |
| WO | WO 2000/049019 A2 | 8/2000 |
| WO | WO 2000/049020 A2 | 8/2000 |
| WO | WO 2000/049021 A2 | 8/2000 |
| WO | WO 2000/057874 A1 | 10/2000 |
| WO | WO 2000/066589 A1 | 11/2000 |
| WO | WO 2000/071521 A1 | 11/2000 |
| WO | WO 2001/027308 A2 | 4/2001 |
| WO | WO 2001/064650 A2 | 9/2001 |
| WO | WO 2001/070716 A1 | 9/2001 |
| WO | WO 2001/073103 A2 | 10/2001 |
| WO | WO 2001/081342 A2 | 11/2001 |
| WO | WO 2001/092255 A2 | 12/2001 |
| WO | WO 2002/008440 A2 | 1/2002 |
| WO | WO 2002/014323 A2 | 2/2002 |
| WO | WO 2002/030356 A2 | 4/2002 |
| WO | WO 2002/032844 A2 | 4/2002 |
| WO | WO 2002/080846 A2 | 10/2002 |
| WO | WO 2002/083180 A1 | 10/2002 |
| WO | WO 2003/074053 A1 | 9/2003 |
| WO | WO 2004/014919 A1 | 2/2004 |
| WO | WO 2004/043493 A2 | 5/2004 |
| WO | WO 2004/043880 A2 | 5/2004 |
| WO | WO 2005/040219 A1 | 5/2005 |
| WO | WO 2005/070468 A2 | 8/2005 |
| WO | WO 2005/085251 A1 | 9/2005 |
| WO | WO 2007/008603 A1 | 1/2007 |
| WO | WO 2007/008848 A2 | 1/2007 |
| WO | WO 2007/020290 A1 | 2/2007 |
| WO | WO 2008/017122 A1 | 2/2008 |
| WO | WO 2008/102008 A1 | 8/2008 |
| WO | WO 2009/067663 A1 | 5/2009 |

(56) References Cited

FOREIGN PATENT DOCUMENTS

| | | |
|---|---|---|
| WO | WO 2009/105969 A1 | 9/2009 |
| WO | WO 2010/115630 A1 | 10/2010 |
| WO | WO 2010/136598 A1 | 12/2010 |
| WO | WO 2011/023883 A1 | 3/2011 |
| WO | WO 2011/136645 A1 | 3/2011 |
| WO | WO 2011/085523 A1 | 7/2011 |
| WO | WO 2011/120053 A1 | 9/2011 |
| WO | WO 2011/130616 A1 | 10/2011 |
| WO | WO 2012/041504 A1 | 4/2012 |
| WO | WO 2012/059882 A2 | 5/2012 |
| WO | WO 2012/112687 A1 | 8/2012 |
| WO | WO 2013/092998 A1 | 6/2013 |
| WO | WO 2013/177481 A1 | 11/2013 |
| WO | WO 2014/009426 A1 | 1/2014 |
| WO | WO 2014/140300 A1 | 9/2014 |
| WO | WO 2014/202773 A1 | 12/2014 |

OTHER PUBLICATIONS

Altschul et al., "Basic Local Alignment Search Tool", J Mol Biol. (1990) 215:403-410.
Amersham Biosciences, Antibody Purification Handbook, (2002) Publication No. 18-1037-46, Edition AC, 112 pages.
Amsberry et al., "The Lactonization of 2'-Hydroxyhydrocinnamic Acid Amides: A Potential Prodrug for Amines", J. Org Chem (1990) 55:5867-5877.
Ando et al., "Purification and Characteristics of a Novel Transglutaminase Derived from Microorganisms", Agric Biol Chem. (1989) 53(10):2613-2617.
Ausubel et al. (Eds.) Current Protocols in Molecular Biology (1993) John Wiley & Sons, Inc., Table of Contents, 15 pages.
Baeuerle et al., "Bispecific T-cell engaging antibodies for cancer therapy", Cancer Res. (2009) 69(12):4941-4944.
Bernhard et al., "Cysteine analogs of recombinant barley ribosome inactivating protein form antibody conjugates with enhanced stability and potency in vitro", Bioconjugate Chem., (1994) 5(2):126-132.
Brabez et al., "Design, synthesis and biological studies of efficient multivalent melanotropin ligands: tools towards melanoma diagnosis and treatment", J Med Chem. (2011) 54(20):7375-7384.
Carillo et al., "The Multiple Sequence Alignment Problem in Biology", Siam J. Appl Math. (1988) 48(5):1073-1082.
Carter et al., "Improved oligonucleotide site-directed mutagenesis using M13 vectors", Nucl Acids Res. (1985) 13(12):4431-4443.
Carter et al., "Humanization of an anti-p185HER2 antibody for human cancer therapy", Proc Natl Acad Sci. USA (1992) 89:4285-4289.
Chapman, Andrew P., "PEGylated antibodies and antibody fragments for improved therapy: a review", Advan Drug Del Rev. (2002) 54:531-545.
Chothia et al., "Canonical Structures for the Hypervariable Regions of Immunoglobulins", J Mol Biol. (1987) 196:901-917.
Connolly et al., "In Vivo Inhibition of Fas Ligand-Mediated Killing by TR6, a Fas Ligand Decoy Receptor", J Pharmacol Exp Ther. (2001) 298(1):25-33.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", J Immunol. (2002) 169(6):3076-3084.
Dennler et al., Enzymatic antibody modification by bacterial transglutaminase. Bioconjugate Chemistry, (2013) 1045:205-215.
Dennler et al., Transglutaminase-based chemo-enzymatic conjugation approach yields homogeneous antibody-drug conjugates. Bioconjugate Chemistry, (2014) 25(3):569-578.
Devereux et al., "A comprehensive set of sequence analysis programs for the VAX", Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003) 21(8):941.
Doronina et al., "Enhanced activity of monomethylauristatin F through Monoclonal Antibody Delivery", Bioconjugate Chem. (2006) 17(1):114-124.
Dosio et al., "Immunotoxins and Anticancer Drug Conjugate Assemblies: The Role of the Linkage between Components", Toxins (2011) 3:848-883.
Edelman et al., "The Covalent Structure of an Entire γG Immunoglobulin Molecule", Proc Natl Acad. USA, (1969) 63:78-85.
Folk et al., "Polyamines as Physiological Substrates for Transglutaminases", J. Biol. Chem. (1980) 255(8):3695-3700.
Genbank Reference Sequence NM_024003.2; "*Homo sapiens* L1 cell adhesion molecule (L1CAM), transcript variant 2, mRNA", May 4, 2013; 8 pages.
Genbank Reference Sequence NM_024003.3; "*Homo sapiens* L1 cell adhesion molecule (L1CAM), transcript variant 2, mRNA", May 26, 2013; 10 pages.
Genbank Reference Sequence NM_0764493.1; "Neural cell adhesion molecule L1 isoform 2 precursor [*Homo sapiens*]", May 26, 2014; 6 pages.
Gorman et al., "Transglutaminase Amine Substrates for Photochemical Labeling and Cleavable Cross-linking of Proteins", J Biol Chem. (1980) 255(3):1175-1180.
Green et al., "Antigen-specific human monoclonal antibodies from mice engineered with human Ig heavy and light chain YACs", Nature Gen. (1994) 7:13-21.
Gribskov et al., (Eds.) Sequence Analysis Primer; Stockton Press (1991); Table of Contents, 7 pages.
Griffin et al, (Eds.) Methods in Molecular Biology-24: Computer Analysis of Sequence Data; Part I & II; Humana Press, New Jersey (1994) Tables of Contents, 8 pages.
Griffiths et al., "Human anti-self antibodies with high specificity from phage display libraries", EMBO J. (1993) 12(2):725-734.
Griffiths et al., "Isolation of high affinity human antibodies directly from large synthetic repertoires", EMBO J. (1994) 13(14):3245-3260.
Grünberg et al. 2013. DOTA-functionalized polylysine: A high number of DOTA chelates positively influences the biodistribution of enzymatic conjugated anti-tumor antibody chCE7agl. PLOS ONE, 8(4):e60350.
Hamblett et al., "Effects of Drug Loading on the Antitumor Activity of a Monoclonal Antibody Drug Conjugate", Clin Cancer Res. (2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Hay et al., "A 2-nitroimidazole carbamate prodrug of 5-amino-1-(Chloromethyl)-3-[(5,6,7-Trimethoxyindol-2-YL)Carbonyl]-1,2-dihydro-3H-Benz[e]indole (amino-SECO-CBI-TMI) for use with ADEPT and GDEPT", Bioorg Med Chem Lttrs. (1999) 9:2237-2242.
Higuchi, Russell "Recombinant PCR" Chapter 22 in Part II of PCR Protocols, A Guide to Methods and Applications [Innis et al. (Eds.)], Academic Press, (1990) pp. 177-183.
Ho et al. Site-directed Mutagenesis by Overlap Extension Using the Polymerase Chain Reaction. Gene (1989) 77(1):51-59.
Hollinger et al., "Engineered antibody fragments and the rise of single domains", Nature Biotech. (2005) 23(9):1126-1136.
Ill et al., "Design and construction of a hybrid immunoglobulin domain with properties of both heavy and light chain variable regions", Prot Engineer. (1997) 10(8):949-957.
Ito et al., "A General Method for Introducing a Series of Mutations into Cloned DNA Using the Polymerase Chain Reaction", Gene (1991) 102(1):67-70.
Jackman et al., "Development of a two-part strategy to identify a therapeutic human bispecific antibody that inhibits IgE receptor signaling", J Biol Chem. (2010) 285(27):20850-20859.
Jakobovits et al., "Germ-line transmission and expression of a human-derived yeast artificial chromosome", Nature (1993) 362:255-258.
Jones et al., "Replacing the complementarity-determining regions in a human antibody with those from a mouse", Nature (1986) 321:522-525.

(56) References Cited

OTHER PUBLICATIONS

Josten et al., "Use of microbial transglutaminase for the enzymatic biotinylation of antibodies", J Immunol Meth. (2000) 240:47-54.
Junutula et al., "Site-specific conjugation of a cytotoxic drug to an antibody improves the therapeutic index", Nature Biotech (2008) 26(8):925-932.
Kabat et al., (Eds.) Sequences of Proteins of Immunological Interest, 5th Edition; (1991) Table of Contents; 11 pages.
Kämpfer et al., "A numerical classification of the genera *Streptomyces* and *Streptoverticillium* using miniaturized physiological tests", J Gen Microbiol. (1991) 137:1831-1891.
Kajiwara et al., "Expression of L1 Cell Adhesion Molecule and Morphologic Features at the Invasive Front of Colorectal Cancer", Anat Pathol. (2011) 136(1):138-144.
Kamiya et al., "Site-specific cross-linking of functional proteins by transglutamination", Enzy Micro Tech. (2003) 33:492-496.
Kingsbury et al., "A Novel Peptide Delivery System Involving Peptidase Activated Prodrugs as Antimicrobial Agents. Synthesis and Biological Activity of Peptidyl Derivatives of 5-Fluorouracil", J Med Chem. (1984) 27:1447-1451.
Knappik et al., "Fully Synthetic Human Combinatorial Antibody Libraries (HuCAL) Based on Modular Consensus Frameworks and CDRs Randomized with Trinucleotides", J Mol Biol. (2000) 296:57-86.
Knogler et al., "Copper-67 Radioimmunotherapy and Growth Inhibition by Anti-L1-Cell Adhesion Molecule Monoclonal Antibodies in a Therapy Model of Ovarian Cancer Metastasis", Clin Cancer Res (2007) 13(2):603-611.
Kuil et al., "ITAM-derived phosphopeptide-containing dendrimers as multivalent ligands for Syk tandem SH2 domain", Org Biomol Chem. (2009) 7:4088-4094.
Kunkel, Thomas A., "Rapid and efficient site-specific mutagenesis without phenotypic selection", Proc Natl Acad Sci USA (1985) 82:488-492.
Lesk, Arthur M. (Ed.) Computational Molecular Biology, Oxford University Press (1988); Table of Contents; 4 pages.
Lin et al., "Transglutaminase-catalyzed site-specific conjugation of small-molecule probes to proteins in vitro and on the surface of living cells", J Am Chem Soc. (2006) 128(14):4542-4543 (7pages).
Liu et al, "Identification of Active Site Residues in the "GyrA" Half of Yeast DNA Topoisomerase II", J Biol Chem. (1998) 273(32):20252-20260.
Lonberg et al., "Antigen-specific human antibodies from mice comprising four distinct genetic modifications", Nature (1994) 368:856-859.
Lonberg, Nils, "Human antibodies from transgenic animals", Nature Biotech. (2005) 23(9):1117-1125.
Lorand et al., "Specificity of Guinea Pig Liver Transglutaminase for Amine Substrates", Biochem. (1979) 18(9):1756-1765.
Lorand et al., "Transglutaminases: Cross-linking enzymes with pleiotropic functions", Nature (2003) 4:140-156.
Lyon et al., "Conjugation of Anticancer Drugs through Endogenous Monoclonal Antibody Cysteine Residues", Meth Enzymol. (2012) 502:123-138.
Maeda et al., "Susceptibility of human T-cell leukemia virus type I-infected cells to humanized anti-CD30 monoclonal antibodies in vitro and in vivo", Cancer Sci. (2010) 101(1):224-230.
McCafferty et al., "Phage antibodies: Filamentous phage displaying antibody variable domains", Nature (1990) 348:552-554.
Morrison et al., "Chimeric human antibody molecules: Mouse antigen-binding domains with human constant region domains", Proc Natl Acad Sci. USA (1984) 81:6851-6855.
Murthy et al., "Residue Gln-30 of Human Erythrocyte Anion Transporter is a Prime Site for Reaction with Intrinsic Transglutaminase" J Biolog Chem. (1994) 269(36):22907-22911.
Murthy et al., "Selectivity in the Post-Translational, Transglutaminase-dependent Acylation of Lysine Residues", Biochem. (2009) 48:2654-2660.
Nilsson et al., a synthetic IgG-binding domain based on stapylococcal protein A. Protein Eng. (1987) 1(2):107-113.
Pearson, William R., "Rapid and Sensitive Sequence Comparison with FASTP and FASTA", Meth Enzymol. (1990) 183(5):63-98.
Pearson, William R., "Flexible sequence similarity searching with the FASTA3 program package", Methods Mol Biol. (2000) 132:185-219.
Presta, Leonard G., "Antibody engineering", Curr Opin Struct Biol. (1992) 2:593-596.
Presta et al., "Humanization of an Antibody Directed Against IgE", J Immunol. (1993) 151(5):2623-2632.
Riechmann et al., "Reshaping human antibodies for therapy", Nature (1988) 332:323-327.
Rodrigues et al., "Synthesis and β-lactamase-mediated activation of a cephalosporin-taxol prodrug", Chem Biol. (1995) 2:223-227.
Roguska et al., "Humanization of murine monoclonal antibodies through variable domain resurfacing", Proc Natl Acad Sci. (1994) 91:969-973.
Sambrook et al., (Eds.) Molecular Cloning—A Laboratory Manual, [2nd Edition]; Cold Spring Harbor Laboratory Press, NY; (1989) Table of Contents, 30 pages.
Sambrook et al., (Eds.) Molecular Cloning—A Laboratory Manual, [3rd Edition]; vol. 1; Cold Spring Harbor Laboratory Press, NY; (2001); Table of Contents, 18 pages.
Sazinsky et al., "Aglycosylated immunoglobulin G1 variants productively engage activating Fc receptors", PNAS (2008) 105(51):20167-20172.
Sims et al., "A Humanized CD18 Antibody can block Function without Cell Destruction", J Immunol. (1993) 151:2296-2308.
Smith, Douglas W. (Ed.), Biocomputing—Informatics and Genome Projects, Academic Press, Inc. (1993) Table of Contents, 7 pages.
Strop et al., "Location Matters: Site of Conjugation Modulates Stability and Pharmacokinetics of Antibody Drug Conjugates", Chem Biol. (2013) 20(2):161-167.
Sung et al., "Functional glass surface displaying a glutamyl donor substrate for transglutaminase-mediated protein immobilization", Biotech J. (2010) (5):456-462.
Suzuki et al., Glycopinion Mini-Review: N-Glycosylation/ Deglycosylation as a Mechanism for the Post-Translational Modification/Remodification of Proteins. Glycoconjug J. (1995) 12:183-193.
Takazawa et al., Enzymatic Labeling of a Single Chain Variable Fragment of an Antibody With Alkaline Phosphates by Microbial Transglutaminase. Biotech Engin. (2004) 86(4):399-404.
Tan et al., "Superhumanized" Antibodies: Reduction of Immunogenic Potential by Complementarity-Determining Region Grafting with Human Germline Sequences: Application to an Anti-CD28. J Immunol. (2002) 169:1119-1125.
Tomlinson et al., The Repertoire of Human Germline VH Sequences Reveals about Fifty Groups of VH Segments with Different Hypervariable Loops. J Mol Biol. (1992) 227:776-798.
Uhlén et al., Complete Sequence of the Staphylococcal Gene Encoding Protein A—A Gene Evolved Through Multiple Duplications. J Biol Chem. (1984) 259(3):1695-1702.
Vallette et al., Construction of Mutant and Chimeric Genes Using the Polymerase Chain Reaction. Nuc Acids Res. (1989) 17(2):723-733.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wakankar et al., Analytical Methods for Physicochemical Characterization of Antibody Drug Conjugates. Landes Biosci. (2011) 3(2):161-172.
Wängler et al., "Antibody-Dendrimer Conjugates: The Number, Not the Size of the Dendrimers, Determines the Immunoreactivity" Bioconjugate Chem. (2008) (19)4:813-820.
Ward et al., Binding Activities of a Repertoire of Single Immunoglobulin Variable Domains Secreted From *Escherichia coli*. Nature (1989) 341:544-546.
Wells et al., Cassette Mutagenesis: An Efficient Method for Generation of Multiple Mutations at Defined Sites. Gene (1985) 34(2-3):315-323.

(56) References Cited

OTHER PUBLICATIONS

Xu et al., "Characterization of intact antibodydrug conjugates from plasma/serum in vivo by affinity capture capillary liquid chromatography mass spectrometry", Anal Biochem. (2011) 412(1): 56-66.
Yu et al., "Interaction between Bevacizumab and Murine VEGF-A: A Reassessment", Invest Ophtalmol Vis Sci. (Feb. 2008);49(2):522-527.
Yurkovetskiy et al., Synthesis of a Macromolecular Camptothecin Conjugate with Dual Phase Drug Release. Mol Pharm. (2004) 1(5):375-382.
Zoller et al., "Oligonucleotide-directed mutagenesis using M13-derived vectors: an efficient and general procedure for the production of point mutations in any fragment of DNA", Nucl Acids Res. (1982) 10(20):6487-6500.
Zoller et al., "Oligonucleotide-directed mutagenesis of DNA fragments cloned into M13 vectors", Methods Enzymol. (1983) 100:468-500.
International Search Report dated Apr. 23, 2013 for International Application No. PCT/EP2012/076631 filed Dec. 21, 2012.
International Search Report dated Feb. 5, 2014 for International Application No. PCT/EP2012/076606 filed Dec. 21, 2012.
International Search Report and Written Opinion dated Sep. 24, 2014 for International Application No. PCT/EP2014/063064 filed Jun. 20, 2014, 16 pages.
International Search Report dated Jan. 31, 2014 for International Application No. PCT/EP2013/064605 filed Jul. 10, 2013.
U.S. Appl. No. 61/410,840, filed Nov. 5, 2010.
U.S. Appl. No. 61/553,917, filed Oct. 31, 2011.
U.S. Appl. No. 61/579,908, filed Dec. 23, 2011.
U.S. Appl. No. 61/661,569, filed Jun. 19, 2012.
U.S. Appl. No. 61/671,122, filed Jul. 13, 2012.
U.S. Appl. No. 61/671,128, filed Jul. 13, 2012.
U.S. Appl. No. 61/837,932, filed Jun. 21, 2013.
U.S. Office Action dated Feb. 27, 2015 in U.S. Appl. No. 13/725,382, filed Dec. 21, 2012.
U.S. Office Action dated Apr. 23, 2015 in U.S. Appl. No. 14/582,040, filed Dec. 23, 2014.
U.S. Preliminary Amendment dated May 3, 2013 in U.S. Appl. No. 13/883,535, filed May 3, 2013.
U.S. Office Action dated Dec. 19, 2014 in U.S. Appl. No. 13/883,535, filed May 3, 2013.
U.S. Second Preliminary Amendment dated Feb. 17, 2015 in U.S. Appl. No. 13/883,535, filed May 3, 2013.
Chari, Ravi V.J., "Targeted Cancer Therapy: Conferring Specificity to Cytotoxic Drugs", Acc of Chem Res. (Jan. 2008) 41(1):98-107.
Lhospice et al., "Cite-specific conjugation of monomethyl auristatin E to Anti-CD30 antibodies improves their pharmacokinetics and therapeutic index in rodent models", Mol Pharmaceutics (2015) 12:1863-1871.
International Search Report and Written Opinion of the International Searching Authority dated Aug. 20, 2014 for International Application No. PCT/EP2014/063061 filed Jun. 20, 2014.
U.S.Response to Office Action filed Dec. 11, 2015 in U.S. Appl. No. 13/725,382, filed Dec. 21, 2012.
U.S. Office Action dated Feb. 25, 2016 in U.S. Appl. No. 13/725,382, filed Dec. 21, 2012.
U.S. Office Action dated Jan. 29, 2016 in U.S. Appl. No. 14/367,840, filed Jun. 20, 2014.
U.S. Office Action dated Oct. 8, 2015 in U.S. Appl. No. 14/582,040, filed Dec. 23, 2014.
Response to Office Action filed Dec. 8, 2015 in U.S. Appl. No. 14/582,040, filed Dec. 23, 2014.
U.S. Office Action dated Feb. 11, 2016 in U.S. Appl. No. 14/582,040, filed Dec. 23, 2014.
Response to Office Action filed Feb. 29, 2016 in U.S. Appl. No. 14/582,040, filed Dec. 23, 2014.
U.S. Office Action dated Sep. 16, 2015 in U.S. Appl. No. 13/883,535, filed May 3, 2013.
U.S. Response dated Nov. 16, 2015 in U.S. Appl. No. 13/883,535, filed May 3, 2013.
U.S. Office Action dated Dec. 30, 2015 in U.S. Appl. No. 13/883,535, filed May 3, 2013.
Agard et al., "A Strain-Promoted [3+2] Azide-Alkyne Cycloadditiorifor Covalent Modification of Biomolecules in Living Systems", J Am Chem Soc Comm, (2004) 126:15046-15047.
U.S. Response to Office Action filed May 23, 2016 in U.S. Appl. No. 13/725,382, filed Dec. 21, 2012.
U.S. Office Action dated Aug. 8, 2016 in U.S. Appl. No. 13/725,382, filed Dec. 21, 2012.
US. Response to Office Action filed Nov. 9, 2016 in U.S. Appl. No. 13/725,382, filed Dec. 21, 2012.
U.S. Response to Office Action filed Mar. 25, 2016 in U.S. Appl. No. 14/367,840, filed Jun. 20, 2014.
U.S. Office Action dated Jun. 17, 2016 in U.S. Appl. No. 14/367,840, filed Jun. 20, 2014.
U.S. Response to Office Action filed Nov. 14, 2016 in U.S. Appl. No. 14/367,840, filed Jun. 20, 2014.
U.S. Notice of Allowance dated Jun. 6, 2016 in U.S. Appl. No. 14/582,040, filed Dec. 23, 2014.
U.S. Office Action dated Aug. 17, 2016 in U.S. Appl. No. 14/414,432, filed Jan. 12, 2015.
U.S. Response to Office Action filed Nov. 17, 2016 in U.S. Appl. No. 14/414,432, filed Jan. 12, 2015.
U.S. Response dated May 2, 2016 in U.S. Appl. No. 13/883,535, filed May 3, 2013.
U.S. Office Action dated Jul. 5, 2016 in U.S. Appl. No. 13/883,535, filed May 3, 2013.
U.S. Response dated Sep. 1, 2016 in U.S. Appl. No. 13/883,535, filed May 3, 2013.
Starling et al., "In vivo antitumor activity of a panel of four monoclonal antibody-vinca alkaloid immunoconjugates which bind to three distinct epitopes of carcinoembryonic antigen", Bioconjug Chem. (1992) 3(4):315-322.
U.S. Notice of Allowance dated Mar. 28, 2017 in U.S. Appl. No. 13/725,382, filed Dec. 21, 2012.
U.S. Office Action dated Jan. 31, 2017 in U.S. Appl. No. 14/367,840, filed Jun. 20, 2014.
U.S. Office Action dated Mar. 31, 2017 in U.S. Appl. No. 14/414,432, filed Jan. 12, 2015.
U.S. Office Action dated Mar. 28, 2017 in U.S. Appl. No. 14/775,647, filed Sep. 11, 2015.
U.S. Office Action dated Mar. 31, 2017 in U.S. Appl. No. 14/898,693, filed Dec. 15, 2015.
U.S. Notice of Allowance dated Feb. 8, 2017 in U.S. Appl. No. 13/883,535, filed May 3, 2013.
U.S. Rule 312 Amendment dated Apr. 3, 2017 in U.S. Appl. No. 13/883,535, filed May 3, 2013.
Golay et al., "Mechanism of action of therapeutic monoclonal antibodies: Promises and pitfalls of in vitro and in vivo assays", Arch Biochem Biophys (2012) 526:146-153.
Gregson et al., "Linker Length Modules DNA Cross-Linking Reactivity and Cytotoxic Potency of C8/C8' Ether-linked C2-exo-Unsaturated Pyrrolo[2,1-c][1,4]benzodiazepine (PBD) Dimers", J Med Chem (2004) 47:1161-1174.
Hay et al., "Clinical development success rates for investigational drugs", Nat Biotech. (Jan. 2014) 32(1):40-51.
Hu et al., "Rational design of transglutaminase substrate peptides for rapid enzymatic formation of hydrogels", J Am Chem Soc. (Nov. 2003) 125(47):14298-14299.
Jeffrey et al., "Development and Properties of beta-Glucuronide Linkers for Monoclonal Antibody-Drug Conjugates", Bioconj Chem. (2006) 17:831-840.
Jubala et al., "CD20 Expression in Normal Canine B Cells and in Canine non-Hodgkin Lymphoma", Vet Pathol. (2005) 42:368-476.
Kamal et al., "Synthesis of 1,2,3-triazole-linked pyrrolobenzodiazepine conjugates employing 'click' chemistry: DNA-binding affinity and anticancer activity", Bioorg Med Chem Lett. (Feb. 2008) 18(4):1468-1473.
Moses et al., "The growing applications of click chemistry", Chem Soc Rev. (Aug. 2007) 36(8):1249-1262.
Stancovski et al., "Mechanistic aspects of the opposing effects of monoclonal antibodies to the ERBB2 receptor on tumor growth", Proc Natl Acad Sci USA. (Oct. 1991) 88(19):8691-8695.

(56) References Cited

OTHER PUBLICATIONS

International Search Report dated Jun. 25, 2014 for International Application No. PCT/EP2014/055140 filed Mar. 14, 2014.
U.S. Response to Office Action filed May 28, 2015 in U.S. Appl. No. 13/725,382, filed Dec. 21, 2012.
U.S. Office Action dated Aug. 13, 2015 in U.S. Appl. No. 13/725,382, filed Dec. 21, 2012.
U.S. Response to Office Action filed May 20, 2015 in U.S. Appl. No. 14/582,040, filed Dec. 23, 2014.
U.S. Pre-Interview Communication dated Jul. 2, 2015 in U.S. Appl. No. 14/582,040, filed Dec. 23, 2014.
U.S. Response to Pre-Interview Communication filed Jul. 31, 2015 in U.S. Appl. No. 14/582,040, filed Dec. 23, 2014.
Jeger, Simone. 2009. Site-specific conjugation of tumour-targeting antibodies using transglutaminase. *Dissertation submitted to ETH Zurich*, 140 pages.
Jeger et al. 2010. Site-specific and stoichiometric modification of antibodies by bacterial transglutaminase. *Angewandte Chemie International Edition, Wiley VCH*, 49(51):9995-9997.
Jeger et al. 2010. Site-specific and stoichiometric modification of antibodies by bacterial transglutaminase—Supporting Information. *Angewandte Chemie International Edition, Wiley VCH*, 46 pages.
Kamiya et al. 2003. S-peptide as a potent peptidyl linker for protein cross-linking by microbial transglutaminase from *Streptomyces mobaraensis*. *Bioconjugate Chem.*, 14(2):351-357.
Mindt et al. 2008. Modification of different IgG1 antibodies via glutamine and lysine using bacterial and human tissue transglutaminase. *Bioconjugate Chemistry*, 19(1):271-278.
Plagmann et al. 2009. Transglutaminase-catalyzed covalent multimerization of camelidae anti-human TNF single domain antibodies improves neutralizing activity. *Journal of Biotechnology*, 142:170-178.
International Search Report and Written Opinion of the International Searching Authority dated Apr. 15, 2014 for International Application No. PCT/EP2013/073428 filed Nov. 8, 2013, 24 pages.
Alley et al., "Antibody-drug conjugates: targeted drug delivery for cancer", Curr Opin Chem Biol. (2010) 14:529-537.
Beranger S. et al., International ImMunoGeneTics Information Systems, "MCT Scientific Chart" (downloaded from the web Aug. 20, 2017) URL: http://www.imgt.org/IMGTScientificChart/Numbering/Hu_IGHGnber.html; 4 pages.
U.S.Notice of Allowability/Examiner's Amendment dated Apr. 28, 2017 in U.S. Appl. No. 13/725,382, filed Dec. 21, 2012.
U.S. Preliminary Amendment dated Jul. 19, 2017 in U.S. Appl. No. 15/654,585, filed Jul. 19, 2017.
U.S. Response to Office Action filed Apr. 28, 2017 in U.S. Appl. No. 14/367,840, filed Jun. 20, 2014.
U.S. Notice of Allowance dated May 16, 2017 in U.S. Appl. No. 14/367,840, filed Jun. 20, 2014.
U.S. Preliminary Amendment dated Jan. 9, 2017 in U.S. Appl. No. 15/214,331, filed Jul. 19, 2016.
U.S. Response to Office Action filed Aug. 29, 2017 in U.S. Appl. No. 14/414,432, filed Jan. 12, 2015.
U.S. Office Action dated Nov. 17, 2017 in U.S. Appl. No. 14/414,432, filed Jan. 12, 2015.
U.S. Response to Office Action filed Jun. 28, 2017 in U.S. Appl. No. 14/775,647, filed Sep. 11, 2015.
U.S. Office Action dated Aug. 22, 2017 in U.S. Appl. No. 14/775,647, filed Sep. 11, 2015.
U.S. Response to Office Action filed Nov. 21, 2017 in U.S. Appl. No. 14/775,647, filed Sep. 11, 2015.
U.S. Response to Office Action filed Jun. 29, 2017 in U.S. Appl. No. 14/898,693, filed Dec. 15, 2015.
U.S. Office Action dated Oct. 19, 2017 in U.S. Appl. No. 14/898,693, filed Dec. 15, 2015.
U.S. Response to Office Action filed Jan. 19, 2018 in U.S. Appl. No. 14/898,693, filed Dec. 15, 2015.
U.S. Divisional Application/Preliminary Amendment dated May 16, 2017 in U.S. Appl. No. 15/593,259, filed May 11, 2017.
U.S. Response to Pre-Exam Formalities dated Jul. 21, 2017 in U.S. Appl. No. 15/593,259, filed May 11, 2017.

\* cited by examiner

Lys-Val-Cit-PAB-MMAF

Linker Lys-Val-Cit-

SEQUENCE LISTING

```
<160> NUMBER OF SEQ ID NOS: 10

<210> SEQ ID NO 1
<211> LENGTH: 10
<212> TYPE: PRT
<213> ORGANISM: HOMO SAPIENS

<400> SEQUENCE: 1

Glu Gln Lys Leu Ile Ser Glu Glu Asp Leu
1               5                   10

<210> SEQ ID NO 2
<211> LENGTH: 11
<212> TYPE: PRT
<213> ORGANISM: mus musculus

<400> SEQUENCE: 2

Leu Thr Val Leu Gly Ala Ala Ala Glu Gln Lys
1               5                   10

<210> SEQ ID NO 3
<211> LENGTH: 19
<212> TYPE: PRT
<213> ORGANISM: Artificial
<220> FEATURE:
<223> OTHER INFORMATION: Nanobody terminal sequence

<400> SEQUENCE: 3

Thr Pro Thr Gly Gln Gly Thr Gln Val Thr Val Ser Ser Ala Ala Ala
1               5                   10                  15

Glu Gln Lys

<210> SEQ ID NO 4
<211> LENGTH: 8
<212> TYPE: PRT
<213> ORGANISM: Artificial
<220> FEATURE:
<223> OTHER INFORMATION: Affibody terminal sequence

<400> SEQUENCE: 4

Val Asp Ala Asn Ser Glu Gln Lys
1               5

<210> SEQ ID NO 5
<211> LENGTH: 5
```

```
<212> TYPE: PRT
<213> ORGANISM: Artificial
<220> FEATURE:
<223> OTHER INFORMATION: BTG Tag

<400> SEQUENCE: 5

Ser Leu Leu Gln Gly
1               5

<210> SEQ ID NO 6
<211> LENGTH: 7
<212> TYPE: PRT
<213> ORGANISM: Artificial
<220> FEATURE:
<223> OTHER INFORMATION: BTG Tag

<400> SEQUENCE: 6

Gly Gly Gly Gln Gly Gly Leu
1               5

<210> SEQ ID NO 7
<211> LENGTH: 5
<212> TYPE: PRT
<213> ORGANISM: Artificial
<220> FEATURE:
<223> OTHER INFORMATION: BTG Tag

<400> SEQUENCE: 7

Leu Leu Gln Gly Gly
1               5

<210> SEQ ID NO 8
<211> LENGTH: 5
<212> TYPE: PRT
<213> ORGANISM: Artificial
<220> FEATURE:
<223> OTHER INFORMATION: BTG Tag

<400> SEQUENCE: 8

Leu Leu Gln Gly Ala
1               5

<210> SEQ ID NO 9
<211> LENGTH: 5
<212> TYPE: PRT
<213> ORGANISM: Artificial
<220> FEATURE:
<223> OTHER INFORMATION: BTG Tag

<400> SEQUENCE: 9

Leu Leu Gln Gly Gly
1               5

<210> SEQ ID NO 10
<211> LENGTH: 5
<212> TYPE: PRT
<213> ORGANISM: Artificial
<220> FEATURE:
<223> OTHER INFORMATION: BTG Tag

<400> SEQUENCE: 10

Leu Leu Gln Gly Ala
1               5
```

RECOGNITION TAGS FOR TGASE-MEDIATED CONJUGATION

CROSS-REFERENCE TO RELATED APPLICATIONS

This application is the U.S. National Phase of Application No. PCT/EP2013/073428 entitled "RECOGNITION TAGS FOR TGASE-MEDIATED CONJUGATION" filed Nov. 8, 2013, which designated the United States and this application claims the benefit of U.S. Provisional Application No. 61/724,414 filed Nov. 9, 2012, which is incorporated herein by reference in its entirety, including any drawings.

REFERENCE TO SEQUENCE LISTING

The present application is being filed along with a Sequence Listing in electronic format. The Sequence Listing is provided as a file entitled "TGase5 PCT_ST25", created Nov. 7, 2013, which is 2 KB in size. The information in the electronic format of the Sequence Listing is incorporated herein by reference in its entirety.

FIELD OF THE INVENTION

The present invention relates to a method for the functionalization of polypeptides.

BACKGROUND

Protein conjugates are a promising area of therapeutic research. For example. immunoglobulins conjugated to a drug of interest, generally known as antibody drug conjugates (ADCs) have shown promising clinical results. The feasibility of an ADC approach, however, is not only dependent on linker technologies and drugs, but also on the cellular target, and moreover upon the particular antibody to which a drug is linked. Antibodies may bind antigens in different ways, e.g. giving rise to different profiles of internalization, or antibodies may bind to epitopes present on non-targeted tissues. As a consequence, it is generally believed that each antibody must be examined separately. Evaluating large numbers of antibodies for their suitability for ADC approaches is difficult because antibodies must be conjugated to drugs in a stoichiometric manner such that the effect of the antibody (e.g. epitope specificity, affinity, etc.) can be separated from the effect of the drug. Screening of antibodies suitable for further development as ADCs therefore remains an expensive and time-consuming process.

The development of bispecific antibodies shares certain difficulties with ADCs. A variety of formats for bispecific antibodies that bind to two targets simultaneously have been reported. Cross-linking two different receptors using a bispecific antibody to inhibit a signaling pathway has shown utility (see, e.g., Jackman, et al., (2010) J. Biol. Chem. 285:20850-20859), for example to neutralize two different receptors. In other approaches, bispecific antibodies have been used to recruit immune effector cells, where T-cell activation is achieved in proximity to tumor cells by the bispecific antibody which binds receptors simultaneously on the two different cell types (see Baeuerle, P. A., et al, (2009) Cancer Res 69(12):4941-4). Most such approaches involve bispecific antibodies that link the CD3 complex on T cells to a tumor-associated antigen. In another example, a bispecific antibody having one arm which bound FcγRIII and another which bound to the HER2 receptor was developed for therapy of ovarian and breast tumors that overexpress the HER2 antigen. Screening different components of a bispecific antibody to select the best constituent antibodies or fragments however is tedious, requiring expression of many different fusion proteins. In view of the foregoing, there remains a need in the art for methods to screen for new bispecific (or trispecific or other multispecific) antibodies and for new ways to produce such antibodies.

Transglutaminases (TGases) have been exploited for some time in the food industry for their ability to cross-link proteins. TGases have been shown to be capable of conjugating glutamine and lysine residues, including antibodies (see, e.g., Josten et al. (2000) J. Immunol Methods 240, 47-54; Mindt et al (2008) Bioconjug. Chem. 19, 271-278; Jeger et al (2010) Angew. Chem. Int. Ed. 49: 9995-9997); Kamiya et al (2003) Enzyme. Microb. Technol. 33, 492-496 and US patent publication no. 2011/0184147. It appears that both positioning within a protein and neighboring amino acids influence selection by TGase of acceptor glutamines. However, the rules which govern selection by TGases of glutamine residues for modification are still largely unknown. In particular, antibodies typically contain numerous glutamines and lysines, yet would be desirable to have conjugation occur only at certain specified sites.

There is therefore a need in the art for improved methods to predictably conjugate moieties onto polypeptides using TGases.

SUMMARY OF THE INVENTION

The present invention arises, inter alia, from the discovery that a lysine-based linking reagent can be site-specifically conjugated by transglutaminase (TGase) to a glutamine within a peptide tag introduced into an antibody fragment. In one embodiment, the antibody fragment lacks an Fc domain (e.g. lacks a CH2 and/or CH3 domain). In one embodiment, the fragment is a single chain antibody. In one embodiment, the fragment is a F(ab), a F(ab')$_2$, an scFv, an affibody, a V$_H$ domain, a V$_L$ domain, a single domain antibody (e.g., nanobody) such as a V-NAR domain or a V$_H$H domain.

The present invention also provides a multiple step conjugation approach that makes use of a lysine-based linking reagent having a reactive group to functionalize, via TGase, a glutamine of an antibody fragment or a single chain antibody. The glutamine functionalized with a reactive group can then be reacted with a reagent having a complementary reactive group and a moiety of interest. The approach has several advantages, including the ability to conjugate moieties of interest that are typically not well taken up TGase (e.g. poor completion, poor drug:antibody ratios), such as large and/or hydrophobic compounds. The approach also provides for TGase conjugation reactions that are improved because they are in the absence of organic solvents that would otherwise be needed to solubility hydrophobic moieties to be conjugated. Finally, the approach provides for dramatically decreased cost of production because linking small lysine-based linkers with reactive moieties can be provided in excess over antibody, and subsequent moiety of interest (e.g. expensive cytotoxic drugs) can be provided at low excesses (e.g. between 1, 2, or 5 and 10 excess or between 2.5 or 10 and 20 fold excess).

The present invention also arises, from the discovery that attempts at direct TGase-mediated linking of an antibody fragment lacking an Fc domain to another polypeptide via an isopeptide bond (i.e. between a lysine on one antibody and a glutamine on another antibody) can result in significant polymerization of antibodies rather than site-specific conjugation. The present invention provides a multiple step conjugation approach that makes use of lysine-based linking reagents to link two antibodies via acceptor glutamines of each of the two antibodies (e.g. full length antibodies, antibody fragments or a full length antibody and a fragment). By linking two antibodies via their glutamines, the strategy avoids the need to create an isopeptide bond between a glutamine on one antibody and a lysine on the other antibody. Lysine-based reagents may be preferentially conjugated to acceptor glutamines on antibodies, thus preventing auto-polymerization due to reactions between acceptor glutamines and one or more of the many lysines naturally present in antibodies. The aforementioned site specific conjugation of lysine based reagents onto a peptide tag of an antibody fragment enables multispecific (e.g. bispecific) antibodies to be created which include an antibody fragment.

The invention furthermore provides a TGase recognition tag derived from a myc peptide that can be introduced to a variety of polypeptides, including but not limited to antibodies. Applicants show that such TGase recognition tag permits TGase conjugation of several different antibody fragment formats and antibodies having different variable regions. Advantageously, a myc tag can be employed which permits many readily available protein-myc conjugates to be used directly for conjugation without the need for genetic engineering. This opens the possibility for screening approaches where many (e.g. 10, 100, 1000 or more) polypeptides (e.g. antibodies, antibody fragments, non-antibody polypeptides, etc.) are conjugated to a moiety via a lysine-based linker by TGase activity, and then tested for a characteristic of interest. For example, libraries of antibodies, antibody fragments, non-antibody polypeptides, etc., can be screened in which the members of the library are conjugated to a moiety via a lysine-based linker by TGase activity, and then tested for a characteristic of interest.

The use of a linking reagent along with single chain antibodies and/or TGase recognition tags of the invention thus permits highly stoichiometric and efficient conjugation and consequently highly homogenous compositions, particularly useful for pharmaceutical applications.

The conjugation approach is useful for functionalizing polypeptides (e.g. antibodies) with a moiety-of-interest (e.g. a drug, another polypeptide). Advantageously, the acceptor glutamine-comprising sequence of amino acids that serves as a TGase substrate (TGase recognition tag) will serve as a universal recognition tag for TGase that can be introduced into a variety of different polypeptides. The TGase recognition tag can be introduced into a polypeptide that does not naturally comprise such a tag or such particular amino acid sequence. The same tag sequence can be incorporated into different polypeptide species such that different polypeptides can be conjugated to a moiety-of-interest. Such methods permit, inter alia, different polypeptides to be compared to one another in such conjugated form to evaluate which polypeptide is most effective (e.g. best adapted to use with a particular moiety-of-interest or within a multimeric polypeptide (e.g. bispecific antibody).

When the moiety-of-interest is a polypeptide, multimeric polypeptides can be produced. In one aspect, the polypeptide that is functionalized is an antibody. When the polypeptide is an antibody and the moiety-of-interest is another antibody (e.g. a F(ab), a F(ab')$_2$, an scFv, an affibody, a V$_H$ domain, a V$_L$ domain, a single domain antibody (nanobody) such as a V-NAR domain or a V$_H$H domain), multivalent antibodies can be produced (e.g. bispecific antibodies).

In one embodiment, provided is a method for producing a multimeric polypeptide comprising separately coupling a first and a second polypeptide each comprising a TGase recognition tag comprising an acceptor glutamine to a lysine-based linker comprising a reactive group, and then reacting the first and a second polypeptide to create a multimer comprising the first and a second polypeptide linked to one another via the reactive groups of the respective lysine-based linkers. Thus in one embodiment provided is a multimeric polypeptide comprising (a) a first polypeptide comprising a TGase recognition tag, wherein the first polypeptide is linked, via an acceptor glutamine in the tag, to a lysine-based linker, and (b) a second polypeptide comprising a TGase recognition tag, wherein the second polypeptide is linked, via an acceptor glutamine in the tag, to a lysine-based linker, wherein the first and a second polypeptides are linked to one another via a group (RR') or bond formed between the lysine-based linker(s) of the first polypeptide and the lysine-based linker(s) of the second polypeptide. In one aspect, at least one of the first and second polypeptides is an antibody. In one aspect, at least one of (or both of) the first and second polypeptides lacks an Fc domain, optionally at least one of (or both of) the first and second polypeptides is a single chain antibody. Optionally, the single chain antibody is an scFv, an affibody, a V$_H$ domain, a V$_L$ domain, a V-NAR domain or a V$_H$H domain.

In one aspect, provided is an antibody lacking an Fc domain (e.g. a F(ab), a F(ab')$_2$, a single domain antibody (nanobody) such as an scFv, an affibody, a V$_H$ domain, a V$_L$ domain, V-NAR domain or a V$_H$H domain) linked to a moiety-of-interest via a lysine-based linker, wherein the lysine-based linker is conjugated (covalently bound) to an acceptor glutamine within a TGase recognition tag.

In one aspect, provided is a bispecific antibody (e.g. a bispecific antibody comprising two scFv units (a bis-scFv)) comprising a first and a second antibody lacking an Fc domain comprising a TGase recognition tag, wherein the first and second antibodies are linked to one another via a linker conjugated (covalently bound) to an acceptor glutamine within the TGase recognition tag. Optionally, the first antibody and/or the second antibody lacking an Fc domain are single chain antibodies. Optionally, the first antibody and/or the second antibody lacking an Fc domain are linked to one another via a linker conjugated (or covalently bound) to an acceptor glutamine within a TGase recognition tag of the first antibody and to an acceptor glutamine within a TGase recognition tag of the second antibody. Optionally, the linker comprises a group (RR') resulting from the reaction of a first and a second reactive group.

In one aspect provided is a polypeptide comprising a TGase recognition tag comprising a short peptide sequence derived from the c-myc oncogene (e.g. a "myc tag" or "c-myc tag"), or a fragment or derivative thereof. Optionally, said TGase recognition tag comprises an acceptor glutamine residue functionalized with a moiety-of-interest (for example, functionalized with a moiety-of-interest (Z) via a lysine based linker, or a compound of Formula IV).

In one aspect provided is a multi-functional peptide tag (e.g. 5 to 50, 5 to 25 or 4 to 12 amino acid residues), comprising a TGase recognition sequence positioned within a sequence having a second function. Optionally, the second function is recognition by a binding agent, i.e. the second sequence acts as an epitope tag which is specifically recognized by an agent such as an antibody. Optionally, the tag comprises an amino acid sequence from a c-myc tag and the second function is recognition by an anti-c-myc antibody. Preferably said TGase recognition tag comprises an acceptor glutamine residue functionalized with a moiety-of-interest (for example, functionalized with a moiety-of-interest (Z)

via a lysine based linker, or a compound of Formula IV). Such tags can be used to isolate or identify a polypeptide and can be directly used for conjugation of a moiety of interest via a TGase. Also encompassed are polypeptides comprising such tags, e.g. a polypeptide of interest fused to a multi-functional peptide tag described herein.

In one example, a TGase recognition tag comprises an amino acid sequence of SEQ ID NO: 1, a fragment thereof, a sequence at least 50%, 60%, 70% or 80% identical thereto, or a variant thereof comprising 1, 2, 3, 4, 5 or 6 amino acid modifications, wherein said TGase recognition tag comprises an acceptor glutamine residue functionalized with a moiety-of-interest. In one embodiment, the moiety-of-interest is an amino acid or polypeptide bound to the acceptor glutamine via an isopeptide bond. In one embodiment, the moiety-of-interest is bound via a linker, e.g. the acceptor glutamine is functionalized with a compound of Formula Ia, Ib or Ic. Optionally, the polypeptide comprises a polypeptide of interest (e.g. any antibody, an scFv, an affibody, a $V_H$ domain, a $V_L$ domain, a V-NAR domain or a $V_HH$ domain) and a TGase recognition tag comprising an amino acid sequence of SEQ ID NO: 1 or a variant thereof comprising 1, 2, 3, 4, 5 or 6 amino acid modifications. In one example, the TGase recognition tag is placed at the C-terminal or N-terminal end of the polypeptide of interest or antibody. Also provided is a kit comprising a library of at least such 100 polypeptides of, e.g., a library of polypeptides produced from a phage display library.

In one embodiment, provided is a method for making a polypeptide (e.g. an antibody), the method comprising reacting a polypeptide comprising a TGase recognition tag with a lysine-based linker comprising a moiety-of-interest (Z) (e.g. a linker of Formula Ic), in the presence of a TGase and under conditions sufficient such that a polypeptide conjugated to a moiety-of-interest (Z) via a lysine-based linker is obtained.

In one embodiment, provided is a method (e.g., for making a polypeptide), the method comprising:
 (a) providing a polypeptide comprising an epitope tag, wherein said epitope tag further comprises an acceptor glutamine (or providing a TGase recognition tag comprising an epitope tag; or providing a polypeptide comprising an epitope tag and (e.g. adjacent to) a TGase recognition tag);
 (b) bringing the polypeptide into contact with a reagent that has affinity for the epitope tag (e.g. an antibody reagent, a small molecule reagent, a solid support functionalized with the reagent), optionally wherein said bringing into contact results in the purification of the polypeptide comprising an epitope tag; and
 (c) reacting with a lysine-based linker comprising a moiety-of-interest (Z) (e.g. another polypeptide, a linker of Formula Ic), in the presence of a TGase and under conditions sufficient such that a polypeptide conjugated to a moiety-of-interest (Z), preferably via a lysine-based linker, is obtained.

It will be appreciated that steps (b) and (c) can be inverted (i.e. steps (b) and (c) can be performed in any order. Optionally, the polypeptide is an antibody, a single chain antibody, a F(ab), a F(ab)'2, an scFv, an affibody, a $V_H$ domain, a $V_L$ domain, a V-NAR domain or a $V_HH$ domain. Optionally, the polypeptide comprising an epitope tag comprises a polypeptide of interest fused (e.g., at its N-terminal or C-terminal) to the epitope tag.

In one embodiment, provided is a method for making an antibody (e.g. an antibody lacking an Fc domain, a single chain antibody, a F(ab), F(ab')$_2$, an scFv, an affibody, a $V_H$ domain, a $V_L$ domain, a V-NAR domain or a $V_HH$ domain) comprising a moiety-of-interest (Z), the method comprising the steps of:
 (i) reacting an antibody comprising a TGase recognition tag with a lysine-based linker comprising a reactive group (R) (e.g. a compound of Formula Ia) in the presence of a TGase and under conditions sufficient such that an antibody conjugated to such lysine-based linker comprising a reactive group (R) (e.g. an antibody of Formula II) is obtained, and
 (ii) further reacting the resulting antibody of step (i) (e.g. a polypeptide of Formula II) with a compound comprising: (a) a reactive group (R') that reacts with reactive group (R) on the lysine based linker, and (b) a moiety-of-interest (Z) (e.g., a compound of Formula III),
 whereby an antibody is conjugated to a lysine-based linker comprising a moiety-of-interest (Z) is obtained (e.g. a first and a second antibody of Formula IV).

In one embodiment, the moiety-of-interest (Z) is a polypeptide, preferably an antibody, preferably a single chain antibody (e.g. an scFv, an affibody, a $V_H$ domain, a $V_L$ domain, a V-NAR domain or a $V_HH$ domain). In one embodiment, both the moiety-of-interest (Z) and the antibody used as starting material are single chain antibodies (e.g. an scFv, an affibody, a $V_H$ domain, a $V_L$ domain, a V-NAR domain or a $V_HH$ domain) and are produced by a recombinant non-mammalian host cell (e.g. bacterial, E. coli).

In one embodiment provided is a method for producing a multimeric polypeptide comprising the step of:
 (a) providing (e.g. preparing, producing and/or adding to a reaction mixture) a first polypeptide comprising a TGase recognition tag, wherein the first polypeptide is linked, via an acceptor glutamine in the tag, to a lysine-based linker comprising a first reactive moiety;
 (b) providing (e.g. preparing, producing and/or adding to a reaction mixture) a second polypeptide comprising a TGase recognition tag, wherein the second polypeptide is linked, via an acceptor glutamine in the tag, to a lysine-based linker comprising a second reactive moiety, wherein the second reactive moiety is reactive with the first reactive moiety under suitable conditions; and
 (c) reacting the first and second polypeptides, under suitable conditions for said first and second reactive moieties to react with one another, to form a multimeric polypeptide comprising both the first and second polypeptides. Optionally steps (a) and/or (b) comprise a step of reacting the polypeptide comprising a TGase recognition tag with a lysine-based linker comprising a reactive group (R) (e.g. a compound of Formula Ia) in the presence of a TGase and under conditions sufficient such that a polypeptide conjugated to such lysine-based linker comprising a reactive group (R) (e.g. an antibody of Formula II) is obtained. Preferably the resulting multimeric polypeptide comprises said first and second polypeptides linked to one another via a group (RR') resulting from the reaction of the first and second reactive groups. In one preferred embodiment, each polypeptide(s) comprising a TGase recognition tag is an antibody, and antibody lacking an Fc domina, optionally a single chain antibody, (e.g. an scFv, an affibody, a $V_H$ domain, a $V_L$ domain, a V-NAR domain or a $V_HH$ domain).

In one embodiment, provided is a method for making a multispecific (e.g. bispecific) antibody, the method comprising the steps of:
 (i) reacting a first antibody comprising a TGase recognition tag with a lysine-based linker comprising a first reactive group (R) (e.g. a compound of Formula Ia) in the presence of a TGase and under conditions sufficient such that a first antibody conjugated to such lysine-based linker comprising a first reactive group (R) (e.g. an antibody of Formula II) is obtained, (ii) reacting a second antibody comprising a TGase recognition tag with a lysine-based linker comprising a second reactive group (R') reactive with the first reactive group (R) (e.g. a compound of Formula Ib) in the presence of a TGase and under conditions sufficient such that a second antibody conjugated to such lysine-based linker comprising a second reactive group (R') (e.g. an antibody of Formula II) is obtained, (iii) reacting the resulting antibodies of step (i) and (ii) under suitable conditions sufficient for R and R' to form a bond, preferably a covalent bond, such that a multispecific antibody (e.g. an antibody of Formula V) is formed.

Preferably, in any the methods or compositions herein, an antibody sample comprising a plurality of antibody conjugates is obtained, wherein the antibodies have a uniform ratio of functionalized acceptor glutamines:antibody (i.e. acceptor glutamines within a TGase recognition tag).

In one aspect of any of the embodiments herein, the methods are performed (e.g. repeated) for a plurality of polypeptides or polypeptide samples (e.g. 2, 5, 10, 100, 1000 or more). Optionally plurality of polypeptides or polypeptide samples are provided as a library of polypeptides (or a kit comprising such a library), e.g. a library produced from a phage display library.

In one aspect, a polypeptide (e.g. antibody) library is provided that includes a population of phage or a collection of vectors encoding such a population of phage, or cell(s) harboring such a collection of phage or vectors, wherein the vectors encode polypeptides (e.g. antibodies) comprising a TGase recognition tag (e.g. a myc tag), and the library (e.g., some or all of the members of the library). Optionally, the polypeptide comprises an antibody lacking an Fc domain, a single chain antibody, (e.g. an scFv, an affibody, a $V_H$ domain, a $V_L$ domain, a V-NAR domain or a $V_HH$ domain) and is fused at a terminal amino acid (e.g. [C-terminus]) to a myc tag (a full myc tag of SEQ ID NO: 1, a fragment thereof or sequence derived therefrom). In one aspect provided is a method of making a polypeptide comprising reacting one or a plurality of such polypeptides from the library in the presence of a TGase and under conditions sufficient such that a polypeptide is conjugated to a moiety-of-interest (Z) (or to a reactive group) via a lysine-based linker is obtained.

In one aspect, the step of providing an antibody or sample of polypeptides (e.g. antibodies) comprises generating a plurality (e.g. a library, collection) of candidate polypeptides (e.g. antibodies that bind an antigen of interest) comprising a TGase recognition tag, preferably a myc tag, wherein said plurality comprises a first and a second polypeptide. Optionally said step of generating candidate antibodies comprises immunizing animal(s) with an antigen of interest or generating or selecting from a combinatorial library of immunoglobulins to generate a plurality of candidate antibodies that bind the antigen of interest.

As presented herein, the TGase recognition tag (and the acceptor glutamine residue within such tag) is part of the polypeptide (e.g. antibody), and the lysine-based linker is part of the moiety that is conjugated to the acceptor glutamine residue on the polypeptide (e.g. antibody). The lysine based linker is not a lysine residue within the primary sequence of a polypeptide; the lysine based linker comprises a primary amino group and at least five atoms (e.g. five $(CH_2)$— groups, optionally substituted, or a spacer of equal length) that separates the primary amino group from other elements linked thereto (e.g. a moiety-of-interest (Z), a reactive group R or R', etc.).

In one embodiment, a moiety-of-interest (Z) can be attached to the linking reagent. In one embodiment, the lysine-based linker is connected to at least one reactive group. The reactive group is preferably a functionality that is insensitive to water but selectively undergoes a very high conversion addition reaction with a complementary reagent.

Preferably, the lysine-based linker comprises a lysine derivative (Lys), or a functional equivalent thereof. The functional equivalent of a lysine derivative comprises a 2 to 20 carbon chain, or a functional equivalent thereof, with an $H_2N$ or $H_2NCH_2$ (aminomethylene) group, or a protected $H_2N$ or $H_2NCH_2$ group that can be derived from the $H_2N$ or aminomethylene positioned at one or more ends of the carbon chain. The functional equivalent of the carbon chain is a chain of 2 to 20 atoms where one or more atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

One exemplary functional equivalent of the carbon chain is an oligo (ethylene oxide) chain. The functionality within the carbon chain can be included to couple the reactive group to the $H_2NCH_2$ group or protected $H_2NCH_2$ group. The carbon chain, or its functional equivalent, can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The aminomethylene end of a carbon chain is necessarily included in the linking reagent.

Starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverine).

In one embodiment, a polypeptide comprises an acceptor glutamine residue (Q) within a TGase recognition tag, wherein the polypeptide is conjugated (i.e., covalently attached) via said acceptor glutamine residue (Q) to one or more moieties-of-interest (Z) through a linker that comprises a lysine derivative (Lys), or a functional equivalent thereof, optionally wherein the linker further comprises a RR' moiety, a V (or V') moiety, and/or a Y (or Y') moiety. Optionally, the polypeptide is an antibody, preferably an scFv, an affibody, a $V_H$ domain, a $V_L$ domain, a V-NAR domain or a $V_HH$ domain.

In one embodiment, provided is a polypeptide (e.g. an antibody lacking an Fc domain, a single chain antibody) comprising a TGase recognition tag having functionalized acceptor glutamine residue (Q) of Formula IV, below,

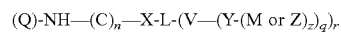   Formula IV where:

Q is a glutamine residue present in the TGase recognition tag;

$(C)_n$ is independently a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

each n is independently an integer selected from among the range of 2 to 20, preferably 3 to 6;

each X is independently NH, O, S, or absent;

each L is independently a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond or a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example). In some embodiments, V is, preferably, a di-, tri-, tetra-, or oligopeptide as described below in the section entitled "The V Moiety";

Y is independently absent, a bond or a continuation of a bond, or a spacer system (e.g., a self-eliminating spacer system or a non-self-elimination spacer system) which is comprised of 1 or more spacers; and Z is a moiety-of-interest, optionally a moiety that improves the pharmacokinetic properties, or a therapeutic moiety or a diagnostic moiety, and each Z is directly coupled to either Y or V when Y is absent, or L when both Y and V are absent; and M is independently: R or (RR')-L'-(V'—(Y'—(Z)$_z$')$_q$')$_r$', wherein each of L', V', Y', z', q', and r' are as defined in Formula III for L, V, Y, z, q, and r, Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of formula III (see, for example, FIG. 1 and FIG. 2). RR' is preferably an addition product of a: thio-maleimide (or haloacetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Optionally, Formula IV will comprise V or V' but not both V and V'. Optionally, Formula IV will comprise Y or Y' but not both Y and Y'.

In one embodiment, any polypeptide (e.g., a murine, rat, human or humanized antibody or any antibody comprising TGase recognition tag), can be characterized as comprising a TGase recognition tag comprising a functionalized acceptor glutamine residue (Q) having Formula II (e.g. an intermediate product).

In any of Formulas herein, q, q', r and r' may optionally be specified to represent degree of branching or polymerization.

In one embodiment, a multimeric polypeptide (e.g. antibody) may be characterized as comprising a first polypeptide and a second polypeptide each comprising a TGase recognition tag, wherein the first polypeptide (e.g. an antibody lacking an Fc domain, a single chain antibody) and a second polypeptide (e.g. an antibody lacking an Fc domain, single chain antibody) are linked to one another through a linkage between a functionalized acceptor glutamine residue ($Q_{pp1}$) of the first polypeptide and a functionalized acceptor glutamine residue ($Q_{pp2}$) of a second polypeptide, the linkage comprising a structure of Formula V, below,

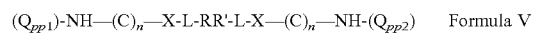
$(Q_{pp1})$-NH—$(C)_n$—X-L-RR'-L-X—$(C)_n$—NH-$(Q_{pp2})$     Formula V where:

$Q_{pp1}$ is a glutamine residue present in a TGase recognition tag of the first polypeptide;

$Q_{pp2}$ is a glutamine residue present in a TGase recognition tag of the second polypeptide, optionally wherein the first and/or second polypeptide is an antibody lacking an Fc domain, e.g., a single chain antibody;

each $(C)_n$ is independently a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

each X is independently NH, O, S, or absent;

each L is independently a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process; and RR' is an addition product between is a reactive group (R) and a complementary reactive group (R') that is complementary for forming at least one bond with reactive group R.

In one aspect of any of the embodiments, the reactive group (R) is selected from the group consisting of: an unprotected or protected thiol, maleimide, haloacetamide, o-phoshenearomatic ester, azide, fulminate, alkyne, cyanide, anthracene, 1,2,4,5-tetrazine, norbornene, and any other strained or otherwise electronically activated alkene. In one aspect of any of the embodiments, the complementary reactive group (R') is selected from the group consisting of: an unprotected or protected thiol, maleimide, haloacetamide, o-phoshenearomatic ester, azide, fulminate, alkyne, cyanide, anthracene, 1,2,4,5-tetrazine, norbornene, and any other strained or otherwise electronically activated alkene.

In one aspect the reactive group (R) is an azide. In one aspect the complementary reactive group (R') is a cycloalkyne.

In one aspect of any of the embodiments, RR' comprises a structure selected from the group consisting of:

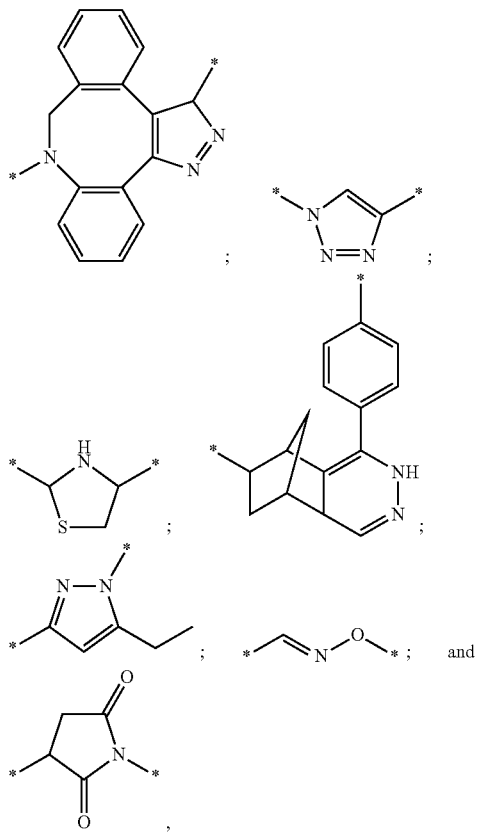

wherein (*) indicates the site of attachment of a linker reagent.

In one embodiment, the first polypeptide is an antibody lacking an Fc domain, e.g., a single chain antibody, having binding specificity for a first antigen and the second polypeptide is an antibody lacking an Fc domain, e.g., a single chain antibody, having binding specificity for a second antigen. In one embodiment, the first antigen is a cancer antigen, a viral antigen, a microbial antigen, or an antigen present on a pro-inflammatory immune cell, and the second antigen is a polypeptide present on the surface of an immune cell, optionally a cell surface receptor on an immune cell (e.g. T cell, an NK cell, a macrophage and/or a dendritic cell, etc.) that modulates that activity of such cell, optionally an activating receptor. Optionally the receptor on an immune cell is a CD3 polypeptide, optionally a Toll-like receptor (e.g. TLR2, TLR3, TLR4, TLR7, TLR9) or an Fc receptor, preferably one or more of the human FcR selected from the group consisting of FcγRI (CD64), FcγRIIA (CD32A), FcγRIIC (CD32C), FcγRIIIA (CD16A), FcγRIIB (CD32B), and FcγRIIIB (CD16B).

In one embodiment provided is a TGase recognition tag comprising the amino acid sequence $X_1QX_2$, wherein Q is glutamine and $X_1$ and $X_2$ may independently be any amino acid other than glutamine. In one embodiment, the methods, through use of a small lysine-based reagent, avoid intra-antibody polymerization reactions. Consequently, TGase recognition tags used herein may comprise a lysine (which lysine will not substantially react with acceptor glutamines to form polymers of antibodies in the presence of TGase). Thus, optionally, $X_1$ or $X_2$ is lysine. In another embodiment, $X_2$ is an amino acid other than lysine. Optionally, $X_1$ is glutamic acid. In one embodiment, the TGase recognition tag is appended to the C-terminus of a single chain antibody. In one embodiment, the TGase recognition tag is appended to the N-terminus of an antibody lacking an Fc domain, e.g., a single chain antibody.

In one embodiment, the TGase recognition tag comprises a sequence derived from the myc oncogene. In one embodiment, the TGase recognition tag comprises the amino acid sequence EQK, optionally the TGase recognition tag comprises the amino acid sequence EQKLISEEDL (SEQ ID NO: 1). In one embodiment, provided is a method for making a polypeptide conjugate, the method comprising reacting a polypeptide comprising a sequence of SEQ ID NO: 1, or a variant of SEQ ID NO: 1 comprising 1, 2, 3, 4, 5 or 6 amino acid modifications, with a lysine-based linker or polypeptide comprising a lysine residue, in the presence of a TGase and under conditions sufficient such that a polypeptide conjugated to a lysine-based linker or polypeptide comprising a lysine residue is obtained.

Any of the methods can further be characterized as comprising any step described in the application, including notably in the "Detailed Description of the Invention"). The invention further relates to a polypeptide obtainable by any of present methods. The invention further relates to pharmaceutical or diagnostic formulations of the polypeptides of the present invention. The invention further relates to methods of using a polypeptide in a method of treatment or diagnosis.

These and additional advantageous aspects and features of the invention may be further described elsewhere herein.

DETAILED DESCRIPTION OF THE INVENTION

Definitions

Figure 1:
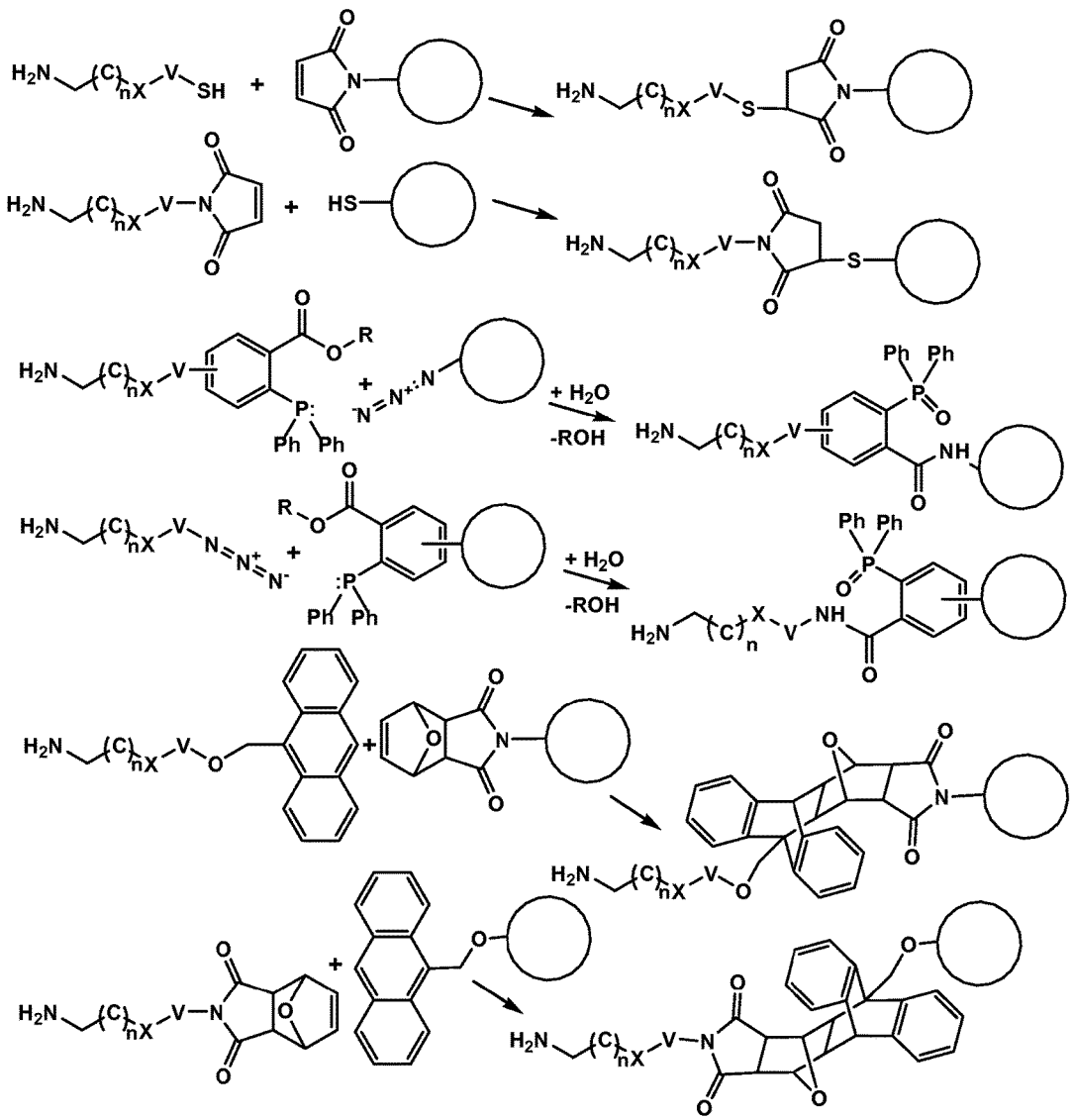
FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

As used in the specification, "a" or "an" may mean one or more. As used in the claim(s), when used in conjunction with the word "comprising", the words "a" or "an" may mean one or more than one.

Where "comprising" is used, this can be replaced by "consisting essentially of", or by "consisting of".

The term "transglutaminase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "TGase recognition tag", refers to a sequence of amino acids that when incorporated into (e.g. appended to) a polypeptide sequence, under suitable conditions, is recognized by a TGase and leads to cross-linking by the TGase through a reaction between an amino acid side chain within the sequence of amino acids and a reaction partner. The TGase recognition tag is a sequence that is not naturally present in the polypeptide comprising the TGase recognition tag. Cross-linking by the TGase may be through a reaction between a glutamine residue (an acceptor glutamine) within the TGase recognition tag and a lysine or a structurally related primary amine such as amino pentyl group.

The term "acceptor glutamine", when referring to an amino acid residue of a polypeptide, means a glutamine residue that, under suitable conditions, is recognized by a TGase and can be cross-linked by a TGase through a reaction between the glutamine and a lysine or a structurally related primary amine such as amino pentyl group. The acceptor glutamine can be a surface-exposed residue.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

An "antibody fragment" comprises a portion of a full-length antibody, preferably antigen-binding or variable regions thereof. Examples of antibody fragments include Fab, Fab', F(ab)₂, F(ab')₂, F(ab)₃, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

An "affibody" is one of a class of small highly robust protein with specific affinities to target proteins. An affibody can be designed and used, for example, like an aptamers. Affibody molecules may comprise a backbone derived from an IgG-binding domain of Staphlococcal Protein A (Protein A produced by *S. aureus*). The backbone can be derived from an IgG binding domain comprising the three alpha helices of the IgG-binding domain of Staphlococcal Protein A called (the "B domain"). The amino acid sequence of the B domain is described in Uhlen et al., J. Biol. Chem. 259: 1695-1702 (1984). Alternatively, the backbone can be derived from the three alpha helices of the synthetic IgG-binding domain known in the art as the "Z domain", which is described in Nilsson et al., Protein Eng. 1: 107-1 13 (1987). The backbone of an affibody comprises the amino acid sequences of the IgG binding domain with amino acid substitutions at one or more amino acid positions.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An antibody having a "biological characteristic" of a reference antibody, is one that possesses one or more of the biological characteristics of that antibody that distinguish it from other antibodies that bind to the same antigen.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

The term "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "reactive moiety" herein refers to a moiety that can be coupled with another moiety without prior activation or transformation.

The term "protecting group" refers to a group that temporarily protects or blocks, i e., intended to prevent from reacting, a functional group, e.g, an amino group, a hydroxyl group, or a carboxyl group, during the transformation of a first molecule to a second molecule.

The phrase "moiety that improves the pharmacokinetic properties", when referring to a compound (e.g. an antibody)

refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket. For example, A-(B)$_b$ with b being a number representing a degree of branching means that b units B are all directly attached to A This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_1$, with b being a number representing a degree of polymerization means that when b is 2, the formula reduces to A-B-B.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, N.J., 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Polypeptides and Antibodies

Any protein or peptide may be utilized as the starting polypeptide in the process described herein. The protein or peptide often is generally isolated when utilized in a cell-free system. The protein or peptide sometimes may optionally be a subregion of a protein, such as in the N-terminus, C-terminus, extracellular region, intracellular region, transmembrane region, active site (e.g., nucleotide binding region or a substrate binding region), a domain or a post-translationally modified region (e. g., phosphorylated, glycosylated or ubiquinated region), for example. Peptides often are 50 amino acids or fewer in length (e.g., 45, 40, 35, 30, 25, 20 or 15 amino acids or fewer in length) and proteins sometimes are 100 or fewer amino acids in length, or 200, 300, 400, 500, 600, 700 or 900 or fewer amino acids in length. The protein or peptide sometimes includes the modification moiety or a portion thereof (e. g., the glycosyl group or a portion thereof). In certain embodiments, the protein is a signal transduction factor, cell proliferation factor, cytokine (e.g., IL-1alpha IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma), apoptosis factor, angiogenesis factor, or cell interaction factor.

The protein or peptide can be an antibody or a non-antibody polypeptide. Antibodies may be produced by a variety of techniques known in the art. Typically, they are produced by immunization of a non-human animal, preferably a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For preferred monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Additionally, a wide range of antibodies are available in the scientific and patent literature, including DNA and/or amino acid sequences, or from commercial suppliers. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens. Other examples include antigens present on immune cells that are contributing to inflammatory or autoimmune disease, including rejection of transplanted tissue (e.g. antigens present on T cells (CD4 or CD8 T cells).

Antibodies will typically be directed to a pre-determined antigen. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In exemplary embodiments the bacterial antigen is derived from a bacterium selected from the group consisting of *Helicobacter* species, in particular *Helicobacter pyloris*; *Borelia* species, in particular *Borelia burgdorferi*; *Legionella* species, in particular *Legionella pneumophilia*; *Mycobacteria* s species, in particular *M. tuberculosis, M. avium, M. intracellulare, M. kansasii, M. gordonae*; *Staphylococcus* species, in particular *Staphylococcus aureus*; *Neisseria* species, in particular *N. gonorrhoeae, N. meningitidis*; *Listeria* species, in particular *Listeria monocytogenes*; *Streptococcus* species, in particular *S. pyogenes, S. agalactiae; S. faecalis; S. bovis, S. pneumonias*; anaerobic *Streptococcus* species; pathogenic *Campylobacter* species; *Enterococcus* species; *Haemophilus* species, in particular *Haemophilus influenzue*; *Bacillus* species, in particular *Bacillus anthracis*; *Corynebacterium* species, in particular *Corynebacterium diphtheriae*; *Erysipelothrix* species, in particular *Erysipelothrix rhusiopathiae*; *Clostridium* species, in particular *C. perfringens, C. tetani*; *Enterobacter* species, in particular *Enterobacter aerogenes*, *Klebsiella* species, in particular *Klebsiella 1S pneumoniae*, *Pasteurella* species, in particular *Pasteurella multocida*, *Bacteroides* species; *Fusobacterium* species, in particular *Fusobacterium nucleatum*; *Streptobacillus* species, in particular *Streptobacillus moniliformis*; *Treponema* species, in particular *Treponema pertenue*; *Leptospira*; pathogenic *Escherichia* species; and *Actinomyces* species, in particular *Actinomyces israelli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The cancer antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue. Antibodies have been raised to target specific tumour related antigens including: Cripto, CD4, CD20, CD30, CD19, CD33, Glycoprotein NMB, CanAg, Her2 (ErbB2/Neu), CD56 (NCAM), CD22 (Siglec2), CD33 (Siglec3), CD79, CD138, CD171, PSCA, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-0017-1A/GA733, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, BAGE, RAGE, LAGE-1, NAG, GnT-V, MUM-1, CDK4, MUC family, VEGF, VEGF receptors, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, $\alpha v \beta 3$ integrins, $\alpha 5 \beta 1$ integrins, $\alpha IIb\beta 3$-integrins, PDGF beta receptor, SVE-cadherin, IL-8, hCG, IL-6, IL-6 receptor, IL-15, $\alpha$-fetoprotein, E-cadherin, $\alpha$-catenin, $\beta$-catenin and $\gamma$-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

Human antibodies may also be produced by using, for immunization, transgenic animals that have been engineered to express a human antibody repertoire (Jakobovitz et Nature 362 (1993) 255), or by selection of antibody repertoires using phage display methods. For example, a XenoMouse (Abgenix, Fremont, Calif.) can be used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Antibodies (as well as other polypeptides) can be produced by selection from a phage display library. A phage display library refers to a collection of phage (e.g., filamentous phage) wherein the phage express an external (typically heterologous) protein (e.g. a protein produced from immunoglobulin $V_H$ and $V_L$ genes). The external protein is free to interact with (bind to) other moieties with which the phage are contacted. Each phage displaying an external protein is a "member" of the phage display library. An antibody library includes for example a phage display library that displays antibodies (binding proteins encoded by one or more antibody genes or cDNAs). The antibody library includes the population of phage or a collection of vectors encoding such a population of phage, or cell(s) harboring such a collection of phage or vectors. The library can be monovalent, displaying on average one single-chain antibody per phage particle or multivalent displaying, on average, two or more single chain antibodies per viral particle.

It will be appreciated that antibodies can also be provided in purified and/or modified form following immunization and/or identification of cells producing an antibody of interest. DNA encoding an antibody of interest can be placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

Humanized antibodies are typically specific chimeric immunoglobulins, immunoglobulin chains or fragments thereof (such as Fv, Fab, Fab', F (ab') 2, "dab", or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (the parent or donor antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536.

Antibodies may be chemically synthesized using known oligopeptide synthesis methodology or may be prepared and purified using recombinant technology. In vitro protein synthesis may be performed using manual techniques or by automation.

Fragments and derivatives of antibodies (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

The DNA of a hybridoma producing an antibody may be modified so as to encode a fragment and/or a single chain antibody. The modified DNA is then inserted into an expression vector and used to transform or transfect an appropriate cell, which then expresses the desired fragment.

TGase Recognition Tag

A TGase recognition tag can be introduced into a polypeptide at any desired position, for example at the C- or N-terminal ends, or at a non-terminal (internal) site in the polypeptide. The TGase recognition tag will thus typically be a sequence that is not naturally present in the polypeptide to which it is introduced. Accordingly, proteins and peptides utilized in the ligation processes described herein sometimes include or are modified with an appropriate TGase recognition motif One or more appropriate TGase recognition tags can be added to a protein or peptide not having one by known synthetic and recombinant techniques.

In one embodiment the TGase recognition tag is fused to the N-terminus of a polypeptide and comprises a minimal spacer amino acid between the N-terminus of the polypeptide and the acceptor glutamine of the TGase recognition tag. In one embodiment the TGase recognition tag is fused to the N- or C-terminus of a polypeptide and comprises a minimal spacer amino acid between the N- or C-terminus of the polypeptide and the acceptor glutamine of the TGase recognition tag. In one such embodiment the TGase recognition tag comprises the amino acid sequence $(X_1)_n Q$, wherein Q is glutamine and each $X_1$ is independently any amino acid (preferably other than glutamine), and n is an integer between 1 and 10, preferably n is less than 8, less than 6, preferably between 1 and 5, preferably 1, 2, 3 or 4. Most preferably, n is 1. Optionally, $X_1$ is glutamic acid or a conservative substitution. In any of the above embodiments, the specified sequence may optionally comprise any amino acids $(X_2)_r$ adjacent to glutamine (Q) such that TGase recognition tag comprises the amino acid sequence $(X_1)_n$-$Q$-$(X_2)_r$, wherein, $X_2$ is absent or each $X_2$ is independently any amino acid, r is an integer between 0 and 300, preferably between 0 and 200, 0 and 100, 0 and 20, preferably between 0 and 10 (e.g. 0, 1, 2, 3, 4, 5, 6, 7, 8, 9 or 10). $X_2$ may represent a sequence of amino acids introduced into a polypeptide (e.g. nor naturally present in such polypeptide) or may represent amino acids naturally present in the polypeptide of interest. Optionally, $X_2$ is lysine.

A polypeptide may optionally further comprise a sequence of amino acids between the C-terminus or N-terminus of a polypeptide and the TGase recognition tag that enhance efficiency of the TGase tag. A polypeptide may therefore comprise a sequence PP1-Z—$(X_1)_n$-Q (or PP1-Z—$(X_1)_n$-Q-$(X_2)_r$), or $(X_1)_n$-Q-$(X_2)_r$—Z-PP1, wherein PP1 is a polypeptide of interest, Q is glutamine, $X_1$ is an amino acid other than glutamine, $X_2$ is absent or each $X_2$ is independently any amino acid other than glutamine, and Z is an amino acid residue or sequence of two or more amino acid residue sequence (e.g. 2, 3, 4, 5, 6, 7, 8 or more residues) that enhances the ability of a TGase to functionalize a glutamine acceptor within a TGase recognition tag. In one embodiment, Z is a sequence of residues that acts as a spacer and/or enhances flexibility of a polypeptide, e.g., is fused to the C- or N-terminal sequences of a polypeptide and enhances flexibility of the respective C- or N-terminal sequences of a polypeptide. Optionally, $(X_2)_r$ comprises a sequence (Z), e.g., to generate a polypeptide comprising a sequence Z—$(X_1)_n$-Q-Z—$(X_2)_r$. Optionally, $X_2$ is an amino acid other than glutamine or lysine.

In one example Z comprises a glycine-serine flexible linker (e.g., $G_4S$).

In one example, a sequence of single amino acid repeats is introduced between the C-terminus or N-terminus of a polypeptide and the TGase recognition tag. For example, Z may be a $W_r$, wherein W is any amino acid and r is an integer between 1 and 10, preferably 1, 2, 3, 4 or 5. In one embodiment, W is an alanine (e.g. W is an alanine and r=3).

Antibodies may optionally comprise one an A (alanine) or S (serine), or a conservative substitution thereof, at the −2 position relative to the acceptor glutamine in the TGase recognition tag. In another embodiment, antibodies may optionally comprise one an A (alanine) or N (asparagine), or a conservative substitution thereof, at the −3 position, relative to the acceptor glutamine in the TGase recognition tag.

Thus, in one embodiment, an antibody chain (e.g. a heavy chain, a single chain antibody, an scFv, an affibody, a $V_H$ domain, a $V_L$ domain, a V-NAR domain or a $V_HH$ domain) comprises, e.g. at its C-terminus, a TGase recognition tag comprising a sequence $W_1$—$W_2$—$(X_1)_n$-Q (or $W_1$—$W_2$—$(X_1)_n$-Q-$(X_2)_r$), wherein Q is glutamine, $X_1$ is an amino acid other than glutamine, and $W_1$ is alanine or serine and $W_2$ is any amino acid residue. In one embodiment, an antibody comprises a sequence $W_1$—$W_2$—$(X_1)_n$-Q (or $W_1$—$W_2$—$(X_1)_n$-Q-$(X_2)_r$), wherein $W_2$ is alanine or asparagine and $W_1$ is any amino acid residue. Optionally $W_2$ is asparagine and $W_1$ is serine. Optionally $W_2$ and $W_1$ are alanine. Optionally, the —$(X_1)_n$-Q-$(X_2)_r$ elements collectively comprise a c-myc tag, e.g., an amino acid sequence EQKLISEEDL (SEQ ID NO: 1) or a fragment or variant thereof.

A polypeptide comprising a TGase recognition tag may optionally further comprise any desired sequence of amino acids not naturally present in the polypeptide inserted upstream or downstream of the TGase recognition tag, for example between the C-terminus or N-terminus of a polypeptide and the TGase recognition tag.

In one embodiment the TGase recognition tag comprises the amino acid sequence $X_1 Q X_2 X_3$, wherein Q is glutamine and $X_1$ and $X_2$ and $X_3$ may independently be any amino acid, preferably an amino acid other than glutamine (optionally an amino acid other than glutamine and other than lysine), or a deletion or insertion. Optionally, $X_1$ is glutamic acid; optionally, $X_2$ is lysine; optionally $X_3$ is leucine. Optionally, $X_2$ is an amino acid other than lysine and other than glutamine. Optionally any one or more of $X_1$ to $X_3$ may be glycine or serine. Optionally any one or more of $X_1$ to $X_3$ may optionally comprise a conservative or non-conservative substitution.

In one embodiment, the TGase recognition tag comprises the amino acid sequence EQKLISEEDL (SEQ ID NO: 1) or a sequence comprising an acceptor glutamine and having at least 50%, 60%, 70%, 80% or 90% amino acid identity to the amino acid sequence of SEQ ID NO: 1. A wide range of polypeptides comprising such tags, typically used as "myc" or "c-myc" tags, are commercially available. Optionally, a TGase recognition tag may comprise an amino acid sequence EQKLISEEDL (SEQ ID NO: 1) or a variant having one or more (e.g., 2, 3, 4, 5, 6, 7, 8 or 9) sequence modifications. Examples of modifications include conservative amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. In other embodiments, the TGase may be derived froma non-myc sequence. Examples of TGase recognition tags include the amino acid sequences: LLQ, LLQG, LSQG, GLLQ, SLLQG (SEQ ID NO: 5), GGGQGGL (SEQ ID NO: 6), LLQGG (SEQ ID NO: 7), LLQGA (SEQ ID NO: 8), LLQGG (SEQ ID NO: 9) and LLQGA (SEQ ID NO: 10).

In one example, an antibody may comprise a sequence: (Ab)-(Z)-(c-myc tag), wherein (Ab) represents an antibody linked (e.g. fused) at its C-terminus to (—(Z)-(c-myc tag)), wherein (Z) may be present or absent and represents any one or more amino acids (e.g. a spacer), and wherein the c-myc tag comprises the amino acid sequence EQKLISEEDL (SEQ ID NO: 1) or a fragment or variant thereof.

Where the polypeptide to be conjugated is an antibody (e.g. an antibody fragment), the antibody will generally comprise a variable region domain that will be linked to (e.g. fused to, with or without intervening amino acid residues) a TGase recognition tag, wherein the acceptor glutamine in the TGase recognicition tag is covalently linked through a lysine based linker (e.g. comprising a —NH—(C)$_n$—X-L moiety or functional equivalent, and optionally further a V and/or Y moiety, optionally further an R or RR' moiety) to a moiety-of-interest Z, e.g. a polymer molecule, a polypeptide, a drug, a detectable or radioactive moiety. The variable region will comprise hypervariable region or CDR sequences, and FR sequences.

Preferably, the antibody, polypeptide or polypeptide of interest (e.g. $PP_1$ in the formula above) that comprises, or into which is introduced, the TGase recognition tag is an antibody chain, for example a heavy chain, a single chain antibody, an scFv, an affibody, a $V_H$ domain, a $V_L$ domain, a V-NAR domain or a $V_HH$ domain.

The location of the TGase recognition tag within a polypeptide may be varied according to the size and nature required. Thus, in one example a TGase recognition tag may be fused directly to a C-terminal or N-terminal amino acid of a polypeptide, e.g. the C terminal amino acid of a variable domain. Optionally, intervening amino acids that are heterologous to the polypeptide (e.g. antibody) may be introduced (e.g. spacer amino acids). For example a TGase recognition tag may be fused to the C-terminus of a VH or VL chain as described above. If desired, further amino acids may be fused at the C-terminal end of the TGase recognition tag.

In other examples, a variable region domain is covalently attached at its C-terminal to at least one other antibody domain or a fragment thereof (e.g. an Fc domain or portion thereof), to which is fused at the C-terminal a TGase recognition tag. In one embodiment, the antibody lacks an acceptor glutamine at position 295 (Kabat EU numbering) in its heavy chain constant region. In one embodiment, the antibody has a glutamine at position 295 (Kabat EU numbering) in its heavy chain constant region and comprises N297-linked glycosylation such that the Q295 is not recognized by TGase (is not conjugated to a lysine based linker). In another embodiment, the antibody comprises an acceptor glutamine at position 295 (Kabat EU numbering) in its heavy chain constant region (e.g. the antibody lacks N297-linked glycosylation). In one example a VH domain may be linked to an immunoglobulin CH1 domain or a fragment thereof. Similarly a VL domain may be linked to a CK domain or a fragment thereof. The CH1 domain may be extended with further amino acids, for example to provide a hinge region domain as found in a Fab' fragment, or to provide further domains, such as antibody CH2 and CH3 domains. In one example, a TGase recognition tag is attached directly to a C-terminal amino acid of a full or truncated CH1, CH2 or CH3 domain, or to a C-terminal amino acid of a full or truncated CK domain. The variable region domain can thus be monomeric and comprise an immunoglobulin heavy (VH) or light (VL) chain variable domain, or it can be dimeric and contain VH-VH, VH-VL or VL-VL dimers in which the VH and VL chains are non-covalently associated or covalently coupled.

A plurality of polypeptides that contain TGase recognition tags (or samples comprising such polypeptides) are thus provided thus and can then be conjugated to a moiety of interest (Z) and screened for a characteristic of interest. Advantageously, the same tag, for example a myc tag, can be incorporated into each polypeptide. The phrase "a plurality of samples" refers to two or more samples. Because the methods provided herein are ideally suited for high throughput screening, in one aspect, the methods are performed simultaneously on at least tens or at least hundreds of samples. One of the strengths of the methods provided herein is that conjugation will be limited to acceptor glutamine(s) in TGase recognition tag(s) which can be readily defined. For example, antibodies libraries can be provided in a format (e.g. in phage display), where antibodies are engineered to contain the TGase recognition tag.

In one embodiment, provided is a library that includes a population of phage or a collection of vectors encoding such a population of phage, or cell(s) harboring such a collection of phage or vectors, wherein the vectors encode different polypeptides or samples (e.g. antibodies) comprising a TGase recognition tag (e.g. a myc tag). The library can be monovalent, displaying on average one single-chain polypeptide (e.g., antibody) per phage particle or multivalent displaying, on average, two or more single chain polypeptides (e.g., antibodies) per viral particle, wherein the polypeptides comprise a TGase recognition tag (e.g. a myc tag).

A library will thus comprise a plurality of polypeptides (e.g. antibodies) or samples. In one aspect, the plurality of polypeptides or samples vary with respect to polypeptide sequence. For example, in one aspect, a first sample will comprise a first antibody having a first amino acid sequence and a second sample will comprise a second antibody having a second amino acid sequence. In embodiments wherein it is desirable to compare antibodies that target the same antigen, the antibodies will immunospecifically bind to the same antigen. For purpose of clarification, the phrase "wherein the plurality of polypeptides or samples vary with respect to sequence" does not require that all of the polypeptides or samples within a plurality of polypeptides or samples vary with respect to amino acid sequence, only that there is certain level of heterogeneity between polypeptides or samples. Although there is a variance in antibody sequence (e.g., a first sample will contain a different antibody than a second sample), it is preferable that a single sample contain one antibody, i.e., that the antibody present in a single sample is of the same sequence. The phrase "substantially all of the polypeptide present in a single sample is of the same sequence" reflects the preference that a single sample contain one polypeptide (e.g. antibody) with the recognition that, in some samples, there may be some contamination with another polypeptide. Preferably, in those samples that have some contamination with another antibody, there is less than 30%, preferably less than 20%, preferably less than 15%, more preferably less than 10%, and even more preferably less than 5%, less than 4%, or less than 3% of contamination with another antibody. In preferred embodiments, the majority of antibody-containing samples (greater that 50% of samples and even more preferably greater than 60%, greater than 70%, greater than 75%, or even greater than 80% of the samples) in a plurality of antibody-containing samples contain one antibody with no or minor amounts of contamination with another antibody (e.g., less than 15%, preferably even less than 10% or less than 5% contamination with another antibody). In some preferred embodiments, a majority of the antibody-containing samples will comprise antibodies that immunospecifically bind to the same antigen.

Lysine-Based Linkers

The polypeptides and samples will be conjugated to a moiety-of-interest via a linking reagent that can be attached, by the action of a TGase, at an acceptor glutamine residue (Q) within the TGase recognition tag which is in turn in part of the primary sequence of the polypeptide. The polypeptides in the polypeptide samples will typically be conjugated to a moiety of interest (Z) such as a drug or diagnostic compound, however the polypeptides may also be retained as intermediates which are conjugated to a reactive group (R), preferably a protected reactive group. Such antibodies can be used for further reactions subsequently. Thus, the linking reagent used will depend on the particular screening strategy used.

In one embodiment the linking reagent comprises a lysine derivative (Lys), or a functional equivalent thereof, that is connected to at least one moiety of interest (Z). In another embodiment, a two-step (or multi-step) strategy is used to attach moieties of interest in a stoichiometric fashion, in which the linking reagent comprises a lysine derivative (Lys), or a functional equivalent thereof, that is connected to a reactive group (R). In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent.

The functional equivalent of a lysine derivative comprises a 2 to 20 carbon chain, or a functional equivalent thereof, with an $H_2N$ or $H_2NCH_2$ (aminomethylene) group or a protected $H_2N$ or $H_2NCH_2$ group that can be derived from the aminomethylene positioned at one or more ends of the carbon chain. The functional equivalent of the carbon chain is a chain of 3 to 20 atoms where one or more atoms (preferably one or more non-terminal atoms) can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

One exemplary functional equivalent of the carbon chain is an oligo (ethylene oxide) chain. The functionality within the carbon chain can be included to couple the reactive group to the $H_2N$ or $H_2NCH_2$ group or protected $H_2N$ or $H_2NCH_2$ group. The carbon chain, or its functional equivalent, can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The aminomethylene end of a carbon chain is necessarily included in the linking reagent.

Starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverine).

A linking reagent comprising a reactive group (R or R') group can be used for a multi-step method. Such linking reagent can have the general Formula Ia or Ib.

Formula Ia (having an R group) is shown below:

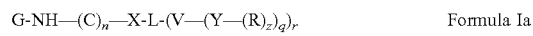

G—NH—(C)$_n$—X-L-(V—(Y—(R)$_z$)$_q$)$_r$  Formula Ia where: G is an H, amine protecting group, or upon conjugation, a polypeptide (e.g., a single chain antibody) attached via an amide bond;

(C)$_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra- or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among the range of 1 to 4;
q is an integer selected from among the range of 1 to 4; and
z is an integer selected from among the range of 1 to 4;

V is independently absent, a bond or a continuation of a bond or a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond, or a spacer system (e.g., a self-eliminating spacer system or a non-self-elimination spacer system) which is comprised of 1 or more spacers; and R is a reactive moiety, preferably a moiety comprising an unprotected or protected thiol, maleimide, a halo-acetamide, a halo-acetamide (e.g. bromo-acetamide, iodo-acetamide, cloro-acetamide), o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L is other than a bond or a continuation of a bond. In an alternative embodiment R is a reactive moiety, preferably a moiety comprising an unprotected or protected thiol, an unprotected or protected amine, maleimide, halo-acetamide, o-phoshenearomatic ester, azide, fulminate, alkyne, cyanide, anthracene, 1,2,4,5-tetrazine, norbornene, other stained or otherwise electronically activated alkene.

Also encompassed are pharmaceutically acceptable salts or solvate thereof, or a protein conjugated linking reagent.

When more than one R group is present in a compound of the formula, the R groups will preferably be compatible such that no R group is a complementary reagent to any other R group. The L group can be a carbon comprising framework, where L is a linear hydrocarbon, a symmetrically or asymmetrically branched hydrocarbon, monosaccharide, disaccharide, linear or branched oligosaccharide (asymmetrically branched or symmetrically branched), other natural oligomer, dimer, trimer, or higher oligomer (linear asymmetrically branched or symmetrically branched) resulting from any chain-growth or step-growth polymerization process, wherein L has r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The linkers of Formula Ia can be reacted with a polypeptide in the presence of a TGase, to produce a polypeptide comprising a TGase recognition tag having functionalized acceptor glutamine residue (Q) of Formula II, below:

(Q)-NH—(C)$_n$—X-L-(V—(Y—(R)$_z$)$_q$)$_r$  Formula II where:

Q is glutamine residue present in the TGase recognition tag; and (C)$_n$, X, L, V, Y, R, z, q and r is defined as in Formula Ia.

In Formula I and II, the linking group L links an aminopeptidyl moiety —NH—(C)$_n$—X or the like to the reactive group R, optionally through one or more V and/or Y moieties where present. L may be a bond connecting V, Y or R directly to the aminopeptidyl moiety. In another aspect, however, L is a linking group that functionally links or spaces the one or more moieties V and/or Y reactive moiety R. In Formula I and II, spacing may make the reactive moiety R more accessible to the reaction partner, for example when the reactive moiety is present on a lysine-based linker and coupled to the antibody and then brought into contact with a reaction partner. In antibodies comprising a functionalized acceptor glutamine of Formula IV spacing may provide for a better accessibility of V, which in the case of enzymatic cleavage or transformation of V, may improve the rate at which V is transformed and/or cleaved.

The polypeptide having a functionalized acceptor glutamine of Formula Ia can optionally be reacted with a reaction partner (e.g a compound of Formula Ib) to create multimeric polypeptides. A polypeptide having a functionalized acceptor glutamine of Formula Ib, below, can be conjugated to a polypeptide of Formula Ia:

G-NH—(C)$_n$—X-L-R'  Formula Ib wherein each of G, C, n, X, and L are as defined in Formula Ia, and R' is a reactive group, e.g. a reactive group complementary for forming at least one bond with reactive group R of Formula Ia or II.

The linkers of Formula Ib can be reacted with a compound (e.g. polypeptide) of Formula Ia, in the presence of a TGase and under suitable conditions, to produce a polypeptide comprising a functionalized acceptor glutamine of Formula V.

In the simplest form, however, a compound comprising the structure of Formula Ic, below, can be reacted with a polypeptide:

G-NH—(C)$_n$—X-L-(V—(Y—(Z)$_z$)$_q$)$_r$  Formula Ic wherein each of G, C, n, X, L, V, Y, z, q, and r are as defined in Formula Ia, and Z is a moiety-of-interest as described herein.

A compound may contain more than one L moiety. Any L' moiety can be defined in the same way as a L moiety. The L moieties may or may not be the same. The linking group L may be a water-soluble moiety or contain one or more water-soluble moieties, such that L contributes to the water solubility of a compound of formula (I)-(VI). An L may also be a moiety or contain one or more moieties that reduce(s) aggregation, which may or may not be a moiety/moieties that also increase(s) the water solubility.

L may be for example a linear linker or a branched linker. In one aspect, the L moiety is branched, optionally further a dendritic structure, so that it can be connected to at least two, three, four or more V, Y or R moieties (or Z where applicable). Each V—Y moiety is however only attached once to an L moiety. Branching can occur at one or more branching atoms that may for example be carbon, nitrogen, silicon, or phosphorus.

When the lysine-based linker comprises branching in L, the number of branches in L that are connected to V and/or Y will generally be prepared so as to equal the total number of branches available for reaction. That is, in preparing the lysine-based linker, chemical conversion will preferably be carried to completion, thereby maintaining the controlled stoichiometry offered by the site-specific TGase-mediated conjugation approach. Thus, preferably, when L is branched, compounds will be functionalized such that each L, V or Y is connected to a R moiety, such that the components of the mixture of antibodies (or the lysine-based linker during preparation) substantially all have the same r value. For example, it can be specified that 90%, 95%, 98% of the antibodies or the lysine-based linker have the same r value. In one embodiment, L is a linear linker. In another embodiment, L is a branched linker.

L and (C)$_n$ groups can be configured based on the overall structure of the linker that is to be used. The linker moiety can be configured to free of or not comprise a large, charged or hydrophobic moiety (e.g. a cyclic, polycyclic or macrocyclic moiety), and the L group may be a bond or a shorter carbon framework. Such linkers can benefit from improved TGase-mediated coupling onto CH2 domains. For example, L may represent or comprise a carbon framework of 1, 2, 3, 4, 5, or 6 linear carbon atoms, unsubstituted or optionally substituted at one or more atoms. Preferably, where L additionally comprises other groups, the 5-20 linear carbon atoms will be adjacent to the (C)$_n$ group, or where present, the X group.

The (C)$_n$ group may for example be a straight, branched and/or cyclic C$_{2-30}$ alkyl, C$_{2-30}$ alkenyl, C$_{2-30}$ alkynyl, C$_{2-30}$ heteroalkyl, C$_{2-30}$ heteroalkenyl, C$_{2-30}$ heteroalkynyl, optionally wherein one or more homocyclic aromatic compound radical or heterocyclic compound radical may be inserted; notably, any straight or branched C$_{2-5}$ alkyl, C$_{5-10}$ alkyl, C$_{11-20}$ alkyl, —O—C$_{1-5}$ alkyl, —O—C$_{5-10}$ alkyl, —O—C$_{11-20}$ alkyl, CH$_2$—(CH$_2$—O—CH$_2$)$_{1-12}$—CH$_2$ or (CH$_2$—CH$_2$—O—)$_{1-12}$, an amino acid, an oligopeptide, glycan, sulfate, phosphate or carboxylate.

In one example the (C)$_n$ group is a carbon comprising framework substituted with one or more O atoms. In one embodiment, the carbon adjacent to the nitrogen is substituted with an O atom. In one embodiment, the carbon adjacent to the nitrogen is unsubstituted. In one embodiment, the (C) group is or comprises an ethylene oxide group, e.g. a CH$_2$—(CH$_2$—O—CH$_2$)$_n$—CH$_2$ group or an (CH$_2$—CH$_2$—O—)$_n$, where n is an integer from 1 to 10.

When a linker comprises a large, charged or hydrophobic moiety (e.g. a cyclic, polycyclic or macrocyclic moiety), for example, wherein R or R' comprise a large, charged or hydrophobic moiety (e.g. a cyclic, polycyclic or macrocyclic moiety such as a cycloalkyne), the L group may be longer carbon framework. Such linkers can benefit from improved TGase-mediated coupling onto CH2 domains. For example, L may represent or comprise a carbon framework of:

a) 2-30 linear carbon atoms optionally substituted at one or more atoms;
b) 2-15 linear carbon atoms optionally substituted at one or more atoms;
c) 5-20 linear carbon atoms optionally substituted at one or more atoms;
d) 5-30 linear carbon atoms optionally substituted at one or more atoms;
e) 5-15 linear carbon atoms optionally substituted at one or more atoms; or
f) 4, 5 or 6 linear carbon atoms optionally substituted at one or more atoms.

Preferably, the 5-20 linear carbon atoms will be adjacent to (the continuation of) the (C) group, or where present, the X group.

For example, L may comprise or be a straight, branched and/or cyclic C$_{2-30}$ alkyl, C$_{2-30}$ alkenyl, C$_{2-30}$ alkynyl, C$_{2-30}$ heteroalkyl, C$_{2-30}$ heteroalkenyl, C$_{2-30}$ heteroalkynyl, optionally wherein one or more homocyclic aromatic compound radical or heterocyclic compound radical may be inserted; notably, any straight or branched C$_{2-5}$ alkyl, C$_{5-10}$ alkyl, C$_{11-20}$ alkyl, —O—C$_{1-5}$ alkyl, —O—C$_{5-10}$ alkyl, —O—C$_{11-20}$ alkyl, CH$_2$—(CH$_2$—O—CH$_2$)$_{1-30}$—CH$_2$ or (CH$_2$—CH$_2$—O—)$_{1-30}$, e.g., (CH$_2$—CH$_2$—O—)$_{1-12}$, (CH$_2$—CH$_2$—O—)$_{1-24}$, an amino acid, an oligopeptide, glycan, sulfate, phosphate, carboxylate. Optionally, L is absent.

In some embodiments, L is a —(C═O)—C$_{1-6}$ alkyl group. In some embodiments, L is a C$_{1-6}$ alkoxy-C$_{1-6}$ alkyl group. In some embodiments, L is a —(C═O)—C$_{1-6}$ alkoxy-C$_{1-6}$ alkyl group. In some embodiments, L is a —(C═O)—C$_{10-20}$ alkyl group. In some embodiments, L is a C$_{1-6}$ alkyl group. In some embodiments, L is a C$_{10-20}$ alkyl group. In some embodiments, L is a —(C═O)—O—C$_{1-6}$ alkyl group. In some embodiments, L is a —(C═O)—O—C$_{2-20}$ alkyl group. In some embodiments, L is a —(C═O)— group. In some embodiments, L is selected from among —(C═O)—CH$_2$—S—

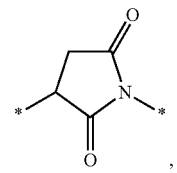 [SMILES: *C1CC(=O)N(*)C1=O]

—(C═O)—CH$_5$—S—

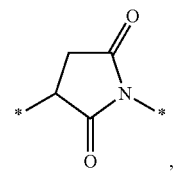 [SMILES: *C1CC(=O)N(*)C1=O]

and —CH$_2$—(CH$_2$—O—CH$_2$)$_4$—CH$_2$—S—

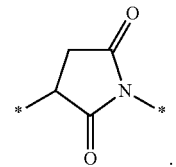 [SMILES: *C1CC(=O)N(*)C1=O]

.

In some embodiments, L is or comprises an amino acid or a di-, tri- tetra- or oligopeptide. In some embodiments, L is selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and citrulline.

The Reactive Moiety R (and Reaction Partners R)

A linker comprising a reactive moiety (R) can be used so as to create a polypeptide having a glutamine functionalized with a reactive compound. The conjugate can then subsequently be reacted with a reaction partner to create a desired end-product (e.g., having a moiety-of-interest (Z)).

R (or its reaction partner R') can be, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2, 4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

When more than one R group is present in a compound of the formula, the R groups will preferably be compatible such that no R group is a complementary reagent to any other R group. The L, V and/or Y groups of formulae I-IV can have r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The reactive group of the linking reagent can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function.

Optionally, two or more compatible reactive groups can be attached to the linking reagent.

In one embodiment, the reactive group is a haloacetamide, (e.g. bromo-acetamide, iodo-acetamide, cloro-acetamide). Such reactive groups will be more stable in vivo (and in serum) compared with maleimide groups.

In one embodiment, the reactive group is a reagent capable of undergoing a "click" reaction. For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including heterocyclic compounds, will preferably be used in linking reagents in which an L group is present, preferably wherein L is an alkyl or heteroalkyl chain of 3-30, optionally 5-30 or 5-15 linear carbon atoms, optionally substituted at one or more atoms. Optionally, L is a $(CH_2-CH_2-O)_{1-24}$ group or a $(CH_2)_{x1}-(CH_2-O-CH_2)_{1-24}-(CH_2)_{x2}-$, wherein x1 and x2 are independently an integer selected among the range of 0 to 20. As shown herein, presence of an L group enables high TGase-mediated coupling when cycloalkynes are used.

Cycloalkynes, including specific compounds, are described for example in U.S. Pat. No. 7,807,619, the disclosure of which is incorporated herein by reference.

In some embodiments, a cycloalkyne may be a compound of Formula A:

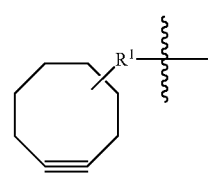

Formula A where:

$R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

$R^1$ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

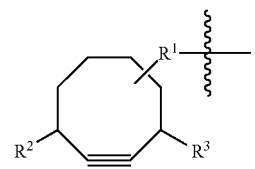

Formula B where:

each of $R^2$ and $R^3$ is independently: (a) H; (b) a halogen atom (e.g., bromo, chloro, fluoro, iodo); (c) $-W-(CH_2)_n-Z$ (where: n is an integer from 1-4 (e.g., n=1, 2, 3, or 4); W, if present, is O, N, or S; and Z is nitro, cyano, sulfonic acid, or a halogen); (d) $-(CH_2)_m-W-(CH_2)_m-R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) $-(CH_2)_n-R^4$ (where: n is an integer from 1-4 (e.g., n=1, 2, 3, or 4); and $R^4$ is nitro, cyano, sulfonic acid, or a halogen); and $R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. $R^1$ can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

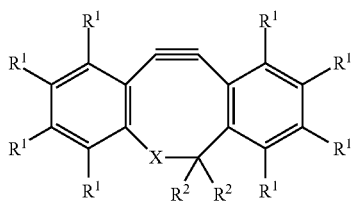

Formula C wherein:

each $R^1$ is independently selected from the group consisting of hydrogen, halogen, hydroxy, alkoxy, nitrate, nitrite, sulfate, and a $C_1$-$C_{10}$ alkyl or heteroalkyl;

each $R^2$ is independently selected from the group consisting of hydrogen, halogen, hydroxy, alkoxy, nitrate, nitrite, sulfate, and a $C_1$-$C_{10}$ organic group; X represents N—$R^3R^4$, NH—$R^4$, CH—N—$OR^4$, C—N—$NR^3R^4$, $CHOR_4$, or $CHNHR_4$; and each $R^3$ represents hydrogen or an organic group and $R^4$ represents linking moiety C (or $(C)_n$) of a linker. In one embodiment, R or R' is a DBCO (dibenzycyclooctyl) group below:

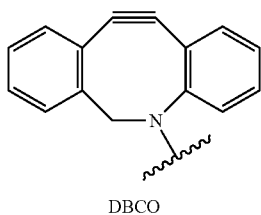 [SMILES: *N1Cc2ccccc2C#Cc2ccccc21 ; "DBCO"]

DBCO

Alkynes such as those described herein above can be reacted with at least one 1,3-dipole-functional compound (e.g., embodied as an R' moiety in a compound of Formula III) in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

The reactive moiety R is connected to L, or when present, V or Y, and is able to react with a suitable functional group (R') on a reaction partner, e.g. a complementary reagent of Formula III which undergoes a high conversion addition reaction when brought into contact with a reactive moiety R. When reactive moiety R is present in an antibody of Formula II, the reaction results in formation of an antibody of Formula IV. In this reaction, the moieties R and R' are transformed into the moiety (RR'). Any R' moiety can be defined in the same way as a R moiety, so long as R and R' are complementary when used in moieties that are to be reacted together.

Exemplary linkers of formulae Ia, or Ib include but are not limited to compounds 1-15:

Compound 1

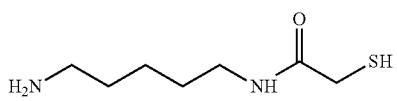

Compound 2

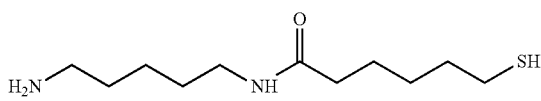

Compound 3

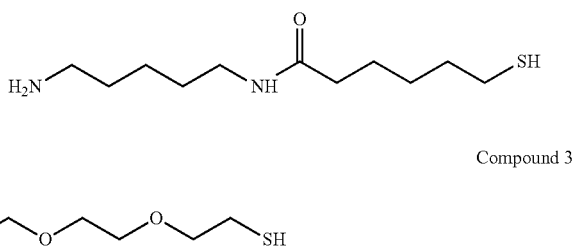

Compound 4

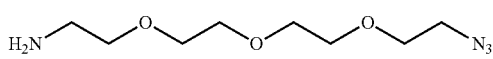

Compound 5

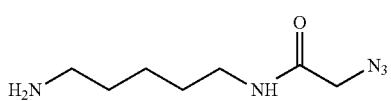

Compound 6

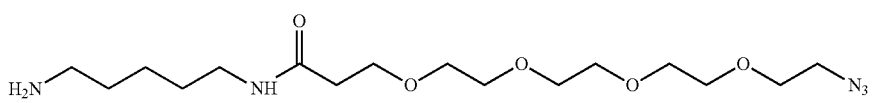

Compound 7

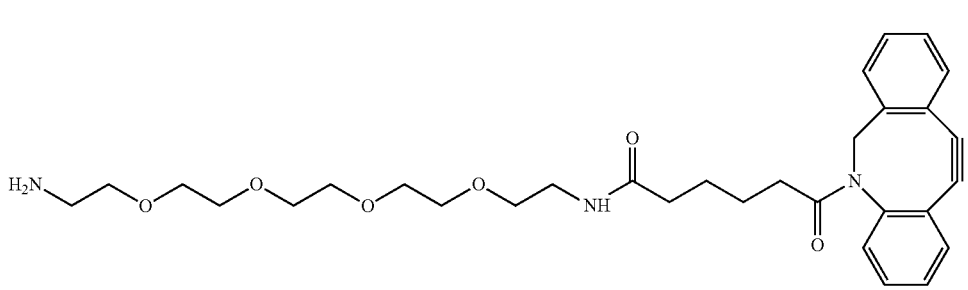

-continued

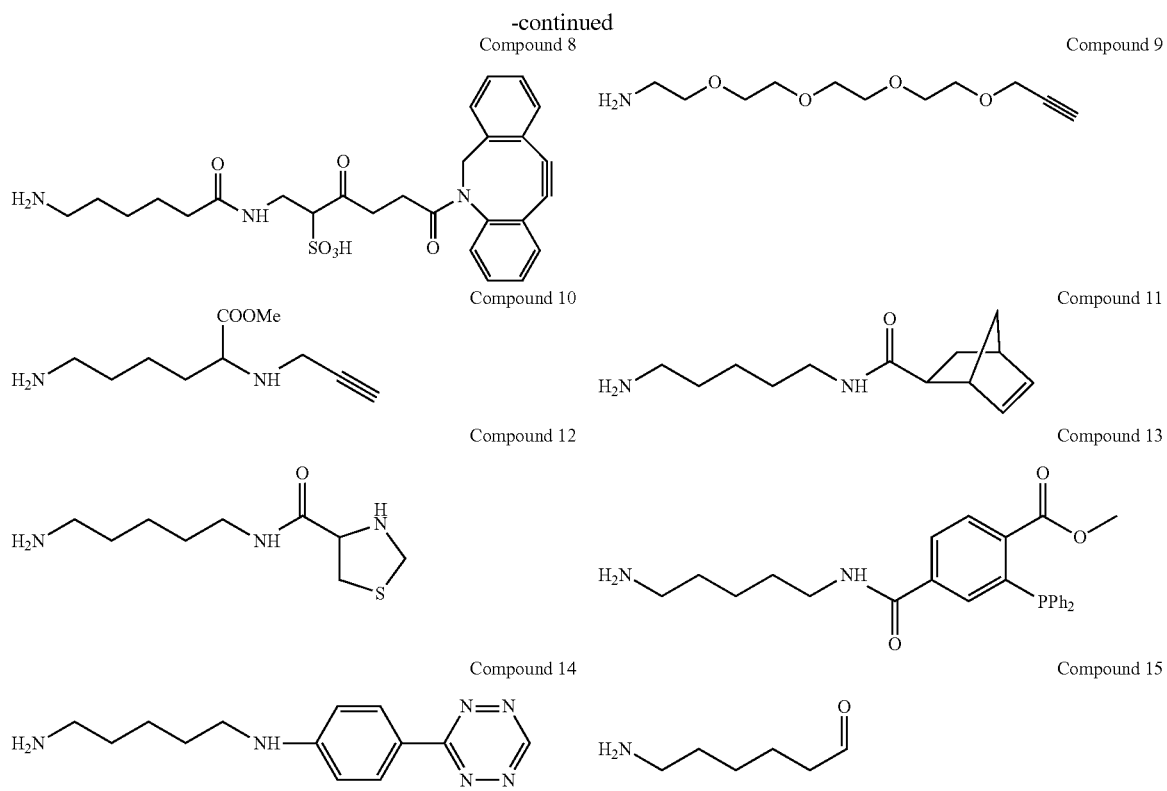

A compound may contain more than one reactive moiety R. The R moieties may or may not be the same. Any one of the R moieties disclosed herein can be utilized in Formula Ib and II. Any one of the R moieties described herein can be used in combination with any of the $(C)_n$, X, L, V, Y, z, q, and r groups described herein. Any one of the R' moieties disclosed herein can be utilized in Formula III. Any one of the R' moieties described herein can be used in combination with any of the L', V', Y', Z, z', q', and r' groups described herein.

The selective and very high conversion addition reactions that can be carried out with the linking reagents can be uncatalyzed or catalyzed reactions. For example, the 2+4 Diels-Alder cycloadditions, thio-maleimide (or haloacetamide) additions, and Staudinger ligations can be carried out without a catalyst. Other very high conversion addition reactions, for example any of the click reactions, can be catalyzed with metal salts, such as Cu, Ru, Ni, Pd, and Pt salts.

R' moieties can be defined in the same way as R, so long as they are reactive with R under suitable conditions. The linking group (RR') in M of compounds of Formula IV represents the remainder of R when the reactive moiety R of Formula II has reacted with a reactive moiety R' in a compound of Formula III. This group (RR') then links the moiety Z (e.g. comprised in the compound of formula IV) with L, V or Y. The group that remains may be a bond.

Figure 9A:
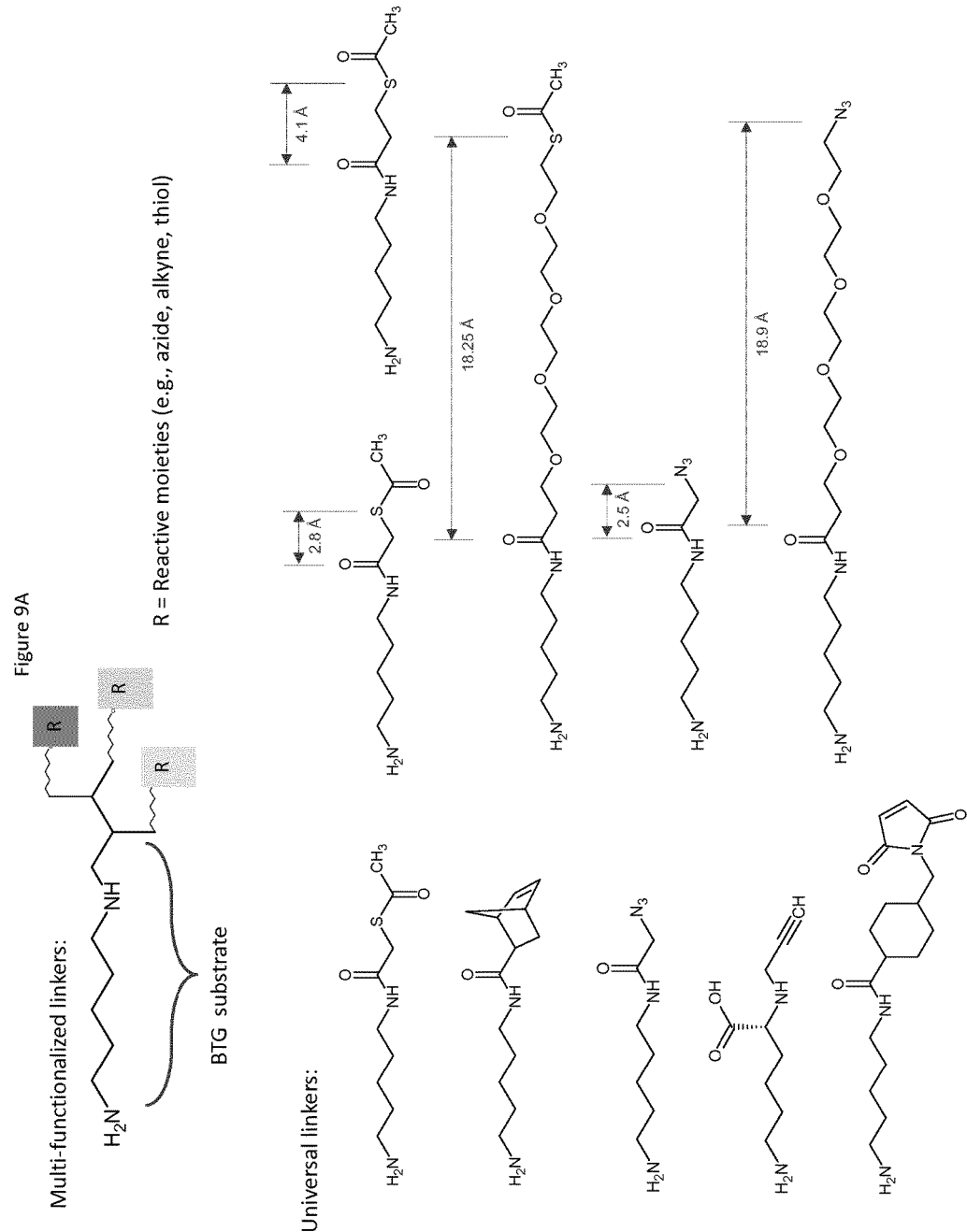
FIG. 9A shows various examples of linking reagents.
Figure 9B:
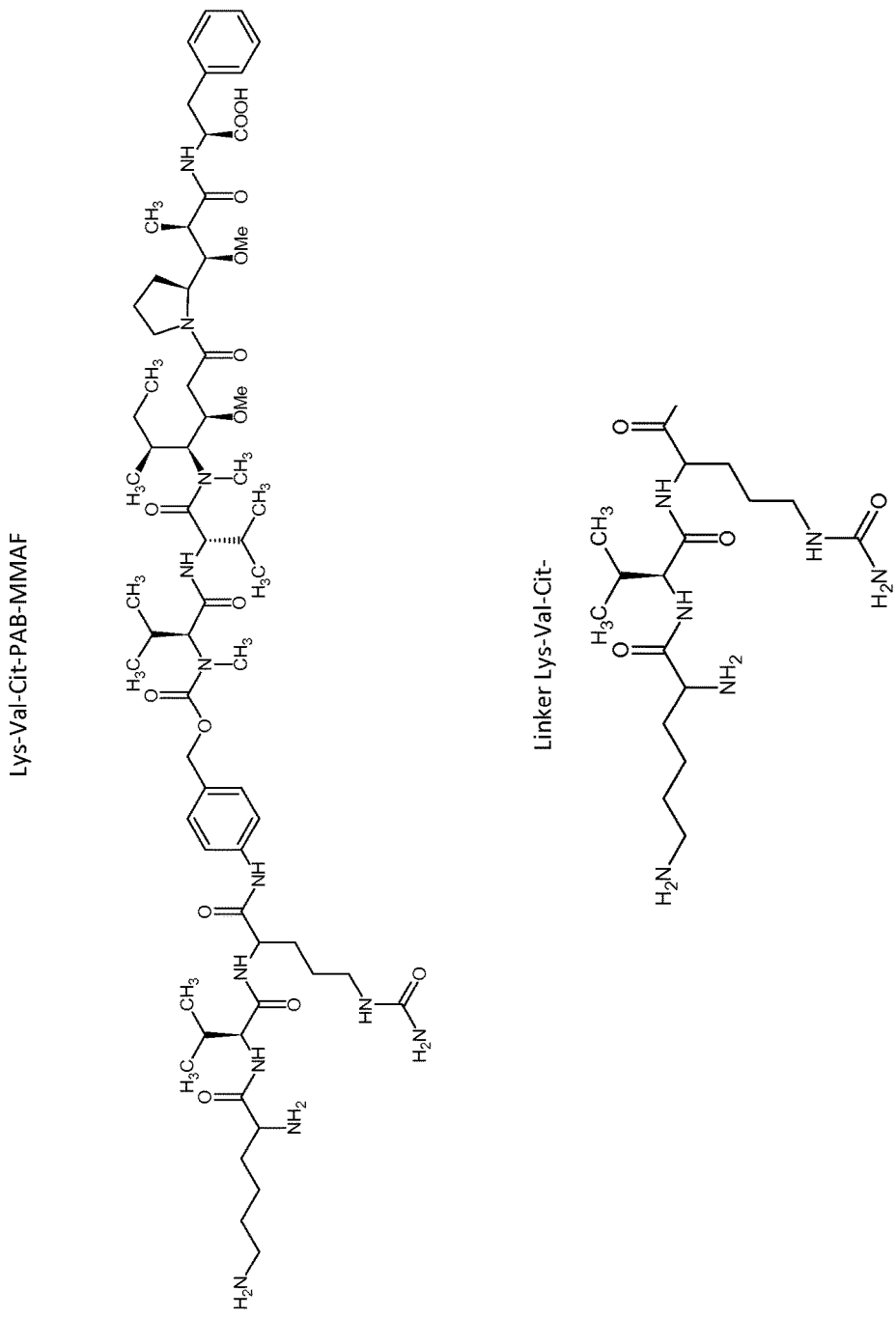
FIG. 9B shows a cleavable val-citrulline moiety-containing linker ("Linker Lys-Val-Cit") and a linker containing a cleavable val-citrulline moiety and a cytotoxic agent MMAF (("Linker Lys-Val-Cit-PAB-MMAF").
Figure 10:
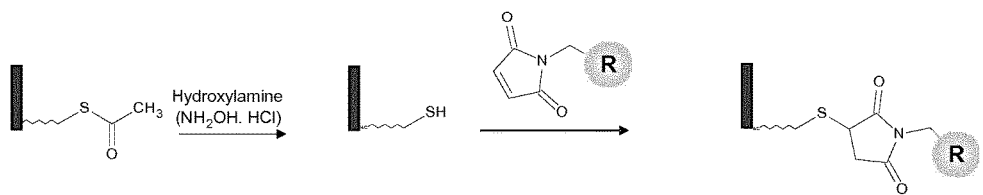
FIG. 10 shows a scheme for preparing a polypeptide conjugate from a S-acetyl-cadaverine linker of FIG. 3, where "R" in the figure is any group, e.g. a moiety-of-interest Z.
Figure 11:
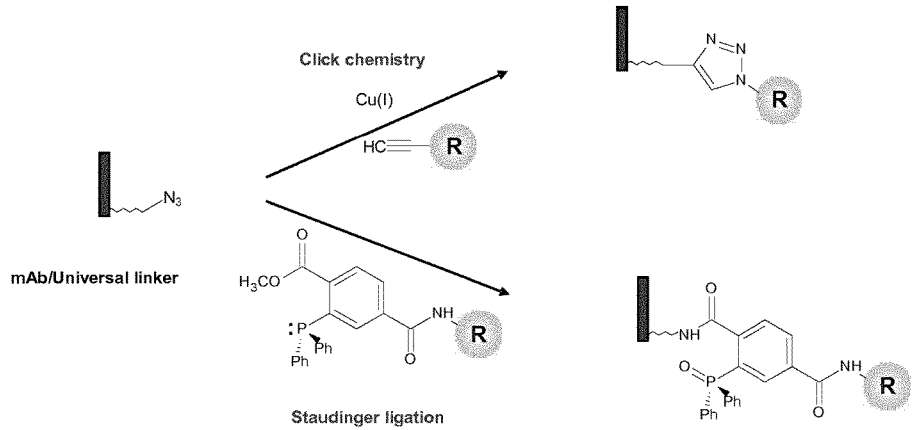
FIG. 11 shows a scheme for preparing a polypeptide conjugate from an azide-cadaverine linker of FIG. 5, where "R" in the figure is any group, e.g. a moiety-of-interest Z.
Figure 12:
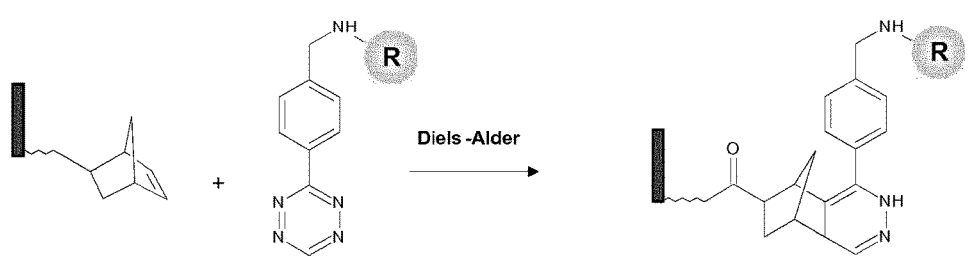
FIG. 12 shows a scheme for preparing a polypeptide conjugate from a norbornyl-cadaverine linker of FIG. 8, where "R" in the figure is any group, e.g. a moiety-of-interest Z.
Figure 13:
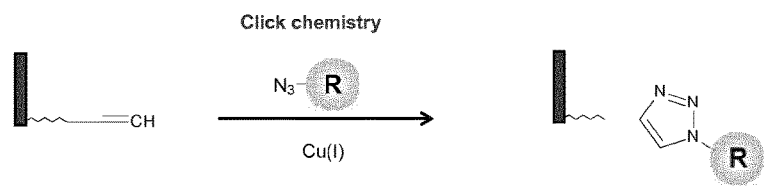
FIG. 13 shows a scheme for preparing a polypeptide conjugate from a glycan-lysine derivative linker of FIG. 7, where "R" in the figure is any group, e.g. a moiety-of-interest Z.

Examples of lysine-based linkers are shown in FIGS. 9A and 9B.

The V Moiety

The V moiety may be incorporated in the lysine-based linker (e.g. connected to L, optionally through Y). However, the V moiety may instead or in addition be incorporated in a compound comprising a moiety-of-interest Z (e.g., a compound R'—V—Y—Z of formula III) that will be reacted with a polypeptide conjugated with a lysine-based linker to form a polypeptide conjugated to the moiety-of-interest Z. Any V' moiety can be defined in the same way as a V moiety. The V moiety is particularly preferred when the polypeptide is an antibody.

The V moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process, e.g. in certain conditions. This condition may for example comprise bringing a compound in an aqueous environment, which leads to hydrolysis of V, or bringing a compound in an environment that contains an enzyme that recognizes and cleaves V, or bringing a compound under reducing conditions, which leads to reduction of V, or bringing a compound in contact with radiation, e.g., UV light, which leads to transformation and/or cleavage, or bringing a compound in contact with heat, which leads to transformation and/or cleavage, or bringing a compound under reduced pressure or bringing a compound under elevated or high pressure, which leads to transformation and/or cleavage. This condition may further be met after administrating a compound to an animal, e.g., a mammal: the condition may be met when the compound localizes to for example a specific organ, tissue, cell, subcellular target, or microbial target, for example by the presence of internal factors (e.g., target-specific enzymes or hypoxia) or application of external factors (e.g., radiation, magnetic fields) or the condition may already be met directly upon administration (e.g., enzymes). In general, transformation of V will directly or indirectly lead to cleavage of V from Y, or Z when Y is absent. It may occur that two or more separate transformations and/or cleavages, requiring the same or different conditions, are required in order to cleave V completely from Y or Z. In this way, increased selectivity may be obtained. A compound may contain more than one V moiety. These V moieties may or may not be the same and may or may not require the same conditions for transformation and/or cleavage.

In one aspect, a compound is used to target one or more therapeutic and/or diagnostic moieties Z to target cells. In this instance, V may for example contain a substrate molecule that is cleaved by an enzyme present in the vicinity of the target cells or inside the target cells, for example tumor cells. V can for example contain a substrate that is cleaved by an enzyme present at elevated levels in the vicinity of or inside the target cells as compared to other parts of the body, or by an enzyme that is present only in the vicinity of or inside the target cells.

If target cell specificity is achieved solely based upon the selective transformation and/or cleavage of V at the target site, the condition (eventually) causing the cleavage should preferably, at least to a certain degree, be target cell-specific, whereas the presence of another target-specific moiety in the compound, for instance when the antibody recognizes an antigen present on a target cell with a degree of specificity, reduces or takes away this requirement. For example, when an antibody causes specific internalization into a target cell, an enzyme also present in other cells may transform and/or cleave V. In one embodiment, transformation and/or cleavage of V occurs intracellularly. In another embodiment, transformation and/or cleavage of V occurs extracellularly.

In one embodiment, the V moiety is a conditionally cleavable moiety.

In one embodiment, V contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment V is a dipeptide, tripeptide, tetrapeptide, or oligopeptide moiety comprised of natural L amino acids, unnatural D amino acids, or synthetic amino acids, or a peptidomimetic, or any combination thereof. In one embodiment, V is a peptide. In another embodiment, V is a dipeptide. In another embodiment, V is a tripeptide. In another embodiment, V is a tetrapeptide. In yet another embodiment, V is a peptidomimetic.

In one embodiment, V contains a substrate for an enzyme.

In another embodiment, V contains a beta-glucuronide that is recognized by beta-glucuronidase present in the vicinity of or inside tumor cells.

In one embodiment, V contains a substrate for an extracellular enzyme. In another embodiment, V contains a substrate for an intracellular enzyme.

In yet another embodiment, V contains a substrate for a lysosomal enzyme.

In yet another embodiment, V contains a substrate for the serine protease plasmin.

In yet another embodiment, V contains a substrate for one or more of the cathepsins, for example cathepsin B. When V is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

In one embodiment V comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from any natural or unnatural amino acid.

In another embodiment V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanyllysine and valylcitrulline.

In another aspect, a compound is used to improve the pharmacokinetic properties of Z. V may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or V may for example be or contain a disulfide. V may therefore, optionally together with the connecting atom of L and/or Y (or Z if Y is absent), for example form a carbonate, carbamate, ureum, ester, amide, imine, hydrazone, oxime, disulfide, acetal, or ketal group. It is understood that V can also be or contain such a moiety and/or be transformed and/or cleaved in the same or a similar way when a compound herein is used for other purposes than solely improving the pharmacokinetic properties of Z.

When the compounds are used for other purposes, e.g., an ex vivo diagnostic assay, V may be or contain any of the moieties mentioned above and transformation and/or cleavage of V may occur by any one of the processes mentioned above or by any other functional transformation or cleavage process known to a person skilled in the art. For example, in a diagnostic assay, V may be cleaved or transformed by an enzyme, by reduction, or below, above, or at a certain pH.

When V is conditionally cleavable, the compounds are designed to eventually release at least one Z after cleavage and optional prior transformation of V. Release of Z from a compound via another mechanism is however not excluded.

In any embodiment, V may contain a blocking group to prevent premature transformation and/or cleavage of V before the condition is met under which V is designed to be transformed and/or cleaved.

In another aspect, V is a moiety that is non-cleavable. This means that V cannot be cleaved from Y, or Z when Y is absent, under the conditions the compound containing such a V moiety is designed to be applied, meaning that Z cannot be released in this way. Release of Z from a compound via another mechanism is however not excluded. When V is a non-cleavable moiety, Y may optionally be absent. A non-cleavable V moiety may be any moiety that cannot be cleaved, or that can be cleaved only very slowly, under the conditions the compound containing such a V moiety is designed to be applied, e.g. in vivo or in vitro. For example, when applied in vivo, V will not or only very slowly be cleaved by enzymes present in the in vivo model used or by hydrolysis or as a consequence of other biological processes that may occur in said model. Such V may therefore, optionally together with the connecting atom of L and/or Z, for example, be a carbonyl group, an amide group, an ureum group, an ester group, a carbonate group, a carbamate group, or an optionally substituted methyleneoxy or methyleneamino group V may be preferred to be non-cleavable when it is not required that the one or more moieties Z are released. This may for example be the case when Z does not require to become released before it can exert its therapeutic or diagnostic properties.

In one embodiment V is connected to L via a functional group in the side chain of one of the natural or unnatural amino acids. In another embodiment, the N-terminal amino acid of V is connected via its alpha amino group to L.

The Spacer System Y

The spacer system Y, when present, links V and optionally L to one or more moieties R, and following reaction with a compound of Formula III, a moiety-of-interest Z. In one embodiment, Y is absent. In another embodiment, Y is a self-elimination spacer system. A spacer system Y may be incorporated in a compound to for example improve the properties of Z or the compound in general, to provide suitable coupling chemistries, or to create space between V and Z. Any Y' moiety can be defined in the same way as a Y moiety.

A compound may contain more than one spacer system Y. These moieties Y may or may not be the same. When a self-elimination spacer is connected to one or more other self-elimination spacers via a direct bond, this combination of spacers is referred to as 'spacer system'. Herein, a single self-elimination spacer may also be referred to as a spacer system. A spacer system may be branched or unbranched and contain one or more attachment sites for Z as well as V. Self-elimination spacers that are able to release only a single moiety are called 'single release spacers'. Self-elimination spacers that are able to release two or more moieties are called 'multiple release spacers'. Spacers, may be either branched or unbranched and self-eliminating through a 1,2+2n-elimination (n>/=1), referred to as "electronic cascade spacers". Spacers may eliminate through a cyclization process under formation of a cyclic ureum derivative, referred to as "w-amino aminocarbonyl cyclization spacers".

The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g. US 2005/0256030 A1), such as 2-aminoimidazol-5-methanoi derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al. Chemistry Biology, 1995, 2, 223) and 2-aminophenyl-propionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers.

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an antibody-moiety-of-interest conjugate containing a glycine-glycine spacer unit by a tumor-cell associated protease would result in release of a glycine-glycine-drug moiety from the remainder of the antibody-moiety-of-interest conjugate. In one such embodiment, the glycine-glycine-drug moiety is then subjected to a separate hydrolysis step in the tumor cell, thus cleaving the glycine-glycine spacer unit from the drug moiety.

A spacer system Y may be connected to more than one V moiety. In this case, transformation and/or cleavage of one of these V moieties may trigger the release of one or more Z moieties. When V moieties that are transformed or cleaved under different conditions are connected to the same Y, release of one or more Z moieties may occur when a compound is brought under one of several different conditions.

Conjugation of Lysine-Based Linkers to an Antibody

TGases' transamidating activity was first observed in guinea-pig liver, and later in micro-organisms, plants, invertebrates, fish, amphibians, and mammals. All TGs, except plant and bacterial TGs (referred to as BTG), require Ca2+ for activation. The Ca2+ concentrations required by mammalian TGases are normally in the supraphysiological range associated with most intracellular processes and Ca2+ activation is also modulated by further regulatory processes, such that TGases are inactive under normal conditions and only activated following major disruptions in physiological homoeostatic mechanisms. Transglutaminases play an important role in biological processes which are dependent on the rapid covalent crosslinking of proteins, e.g. blood coagulation, skin-barrier formation and extracellular-matrix assembly. TGase-mediated reactions result in supramolecular protein structures with high rigidity and stability.

Enzymes of the TG-family catalyze covalent protein crosslinking by forming proteinase resistant isopeptide bonds between a lysine donor residue of one protein and an acceptor glutamine residue of another protein, and is accompanied by the release of ammonia. The catalytic mechanism of transglutaminases has been proposed as follows. After the Glycine-containing first substrate (acceptor or Q-substrate) binds to the enzyme, it forms a γ-glutamylthioester with the cysteine residue in the active center of TGase, known as the acylenzyme intermediate, accompanied by the release of ammonia. The second substrate (donor or K-substrate) then binds to the acylenzyme intermediate and attacks the thioester bond. The product (two proteins crosslinked by an Nε(γ-glutamyl)lysine isopetide bridge) is formed and released. This re-establishes the active-centre Cys residue of the enzyme in its original form and allows it to participate in another cycle of catalysis. The formation of the covalent acylenzyme intermediate is thought to be the rate-limiting step in these reactions. The catalytic triad of many transglutaminases is papain-like, containing Cys-His-Asp (where His is histidine and Asp is aspartic acid) and, crucially, a tryptophan (Trp) residue located 36 residues away from the active-centre Cys. In contrast, bacterial TG isolated from *Streptoverticillium* sp (vide supra) has an atypical catalytic triad and shows no sequence homology with the papain-like catalytic triad of other TGases.

TGases display strict specificity in recognition of glutamine protein substrates. However, TGases display poor specificity for recognition of the acyl-acceptor amine group, which can either be the ε-amino group of peptidyl lysine or a low-molecular mass primary amine (frequently a polyamine) (see, e.g. Folk, et al. (1980) J. Biol. Chem. 255, 3695-3700. For example, in addition to lysine, the small lysine-mimicking primary amines 5-pentylamine (cadaverine) can efficiently bind to the acylenzyme intermediate, and a pseudo-isopeptide bond with the glutamine-containing protein is formed. See, e.g., Lorand, L. et al. (1979) Biochemistry 18, 1756-1765 (1979); Murthy, S. N. et al. (1994). J. Biol. Chem. 269, 22907-22911 (1994); Murthy, P. et al. (2009) Biochemistry (2009).

Bacterial, archaeal and eukaryotic TGases have been characterized and differ in several ways from mammalian TGases (Lorand, L. & Graham, R. M. (2003) Nat. Rev. Mol. Cell Biol. 4, 140-156). BTG and more generally microbial TGases (EC 2.3.2.13, protein-glutamine-γ-glutamyltransferase) such as *Streptomyces mobaraensis* are calcium-independent and have an amino acid sequence of) very different from those of mammalian TGs (Ando et al. (1989) Agric. Biol. Chem. 53, 2613-2617). BTG is furthermore much smaller (37.8 kDa versus 76.6 kDa for guinea pig liver TG). Additionally, BTG shows broader substrate specificity for the amine acceptor glutamine substrates in proteins than do mammalian TGases. These characteristics, together with a higher reaction rate, low cost of production, and a decreased tendency to catalyze deamidation make BTG a preferred enzyme for use in industrial applications.

Any suitable type of transglutaminase (TGase) can be used as long as it is capable of catalyzing the conjugation of the lysine-based linkers. Several types of transglutaminases have been reported in various living organisms including microbials. Examples are TGase from guinea pig liver (GTGase), fish liver (FTGase) and microorganisms (MT-Gase) and any recombinant TGase (rTGase). Other TGases than the ones listed here may be used. Examples of useful TGases include microbial transglutaminases, such as e.g. from *Streptomyces mobaraense, Streptomyces cinnamoneum* and *Streptomyces griseocarneum* fall disclosed in U.S. Pat. No. 5,156,956, which is incorporated herein by reference), and *Streptomyces lavendulae* (disclosed in U.S. Pat. No. 5,252,469, which is incorporated herein by reference) and *Streptomyces ladakanum* (JP2003199569, which is incorporated herein by reference). It should be noted that members of the former genus *Streptoverticillium* are now included in the genus *Streptomyces* (Kaempfer, J Gen Microbiol, 137, 1831-1892, 1991). Other useful microbial transglutaminases have been isolated from *Bacillus subtilis* (disclosed in U.S. Pat. No. 5,731,183, which is incorporated herein by reference) and from various Myxomycetes. Other examples of useful microbial transglutaminases are those disclosed in WO 96/06931 (e.g. transglutaminase from *Bacilus lydicus*) and WO 96/22366, both of which are incorporated herein by reference. Useful non-microbial transglutaminases include guinea-pig liver transglutaminase, and transglutaminases from various marine sources like the flat fish Pagrus major (disclosed in EP-0555649, which is incorporated herein by reference), and the Japanese oyster *Crassostrea gigas* (disclosed in U.S. Pat. No. 5,736,356, which is incorporated herein by reference). A preferred TGase is bacterial transglutaminase (BTG) (see, e.g. EC 2.3.2.13, protein-glutamine-γ-glutamyltransferase). In a more preferred embodiment, the TGase is from *S. mobaraense*. In another embodiment, the TGase is a mutant TGase having at least 80% sequence homology with native TGase. A preferred example is recombinant bacterial transglutaminase derived from *streptomyces mobaraensis* (available from Zedira, Darmstadt, Germany), see also e.g., U.S. Pat. No. 5,156,956.

The TGase-catalyzed reaction can be carried out under mild conditions, from several hours to a day (e.g. overnight). Recombinant BTG (EC 2.3.2.13) from *streptomyces mobaraensis* (Zedira, Darmstadt, Germany) can be used at a concentration of between 1 and 20 U/mL. The lysine-based linker substrates are reacted with polypeptide (e.g., antibody) (1 mg/mL) at ligand concentrations between 400 and 600 mol/L, providing a 60 to 90-fold excess of the substrates over the antibody, or optionally at lower excess of substrates, e.g. 1- to 40-fold, or 10-20 fold. The reactions are performed in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland). Reactions are monitored by LC/MS. Higher amounts of TGase can be used as a function of different lysine-derivatives and substrates.

An acceptor glutamine present in a TGase recognition tag will under suitable conditions, be recognized by a TGase and covalently bound to a lysine-based linker (e.g., compound of Formula I). The result is a polypeptide of Formula II (the acceptor glutamine is functionalized with the compound of Formula I). Resulting polypeptide conjugates can be analyzed using any suitable method. Preferably, the stoichiometry of the conjugated polypeptides can be characterized by liquid chromatography mass spectrometry (LC/MS) using a top-down approach in order to assess the number of lysine-based linker and/or where applicable moieties-of-interest conjugated to polypeptides, and in particular the homogeneity of the composition. Conjugates can be reduced before LC/MS analysis and light chains and heavy chains are measured separately.

Reaction Partners Comprising a Moiety-of-Interest Z and Reactive Group R'

Once a lysine-based linker (e.g., compound of Formula I) comprising a reactive moiety R is conjugated to a polypeptide (e.g., resulting in a polypeptide of Formula II) the polypeptide can be reacted with a compound comprising a moiety Z and a reactive group R', thereby forming a polypeptide-moiety-of-interest conjugate. Optionally, the conjugated polypeptide (e.g. the polypeptide of Formula II) is subjected to a deprotection step to provide an unprotected reactive group (R) and the antibody is then reacted with a compound comprising a reaction partner R'.

R' can be, for example, a moiety comprising an unprotected or protected thiol, maleimide, halo-acetamide (e.g. bromo-acetamide, iodo-acetamide, cloro-acetamide), o-phoshenearomatic ester, azide, fulminate, alkyne, cyanide, anthracene, 1,2,4,5-tetrazine, norbornene, other stained or otherwise electronically activated alkene or, optionally, a protected or unprotected amine, so long as such group when unprotected is reactive with R (when R is unprotected).

The compounds of (e.g. Formula III or Formula Ib) can be reacted with a polypeptide (e.g., 1 mg/mL) at ligand concentrations between 2 and 20 (or between 4 and 20) molar equivalents to the polypeptide, optionally between 2 and 10 (or between 4 and 10) molar equivalents to the antibody, optionally at a less than, or about, 20, 10, 5, 4 or 2 molar equivalents to the antibody. However it will be appreciated that higher excess (equivalents of reaction partner (e.g. Formula III) to antibody (40 to 80 fold, 60 to 90-fold) can also be used.

The compounds of Formula III to be used in reaction with a polypeptide conjugated to a lysine-based linker (but without a moiety-of-interest), e.g, a polypeptide of Formula II, as well as the resulting polypeptide conjugates therefore comprise one or more moieties-of-interest Z. The compounds of Formula III may additionally comprise a moiety V and/or Y, typically depending on which elements are included in the lysine-based linker.

The compounds of Formula III to be used in reaction with a polypeptide conjugated to a lysine-based linker (e.g. an antibody of Formula II) will comprise moieties Z connected to linker L' when Y' and V' are absent, connected to the spacer system Y' or, when Y' is absent, connected to V'. Consequently, a compound of Formula III may comprise a moiety Z connected to or comprising a reactive group R', optionally the moiety Z connected to a reactive group R' via a spacer system Y' or, when Y' is absent, to a reactive group R' via V', or to a reactive group R' via a V'—Y', wherein Z is preferably connected to Y' and V' is connected to R' and Y'.

A compound of Formula III may contain one, two or more Z moieties that are the same or that differ from one another, e.g. different therapeutic moieties, and/or diagnostic moieties.

In one embodiment, the polypeptide of Formula II is reacted with a compound of Formula Ib or III comprising a moiety of interest Z comprising and a reactive group R' capable of forming a bond with reactive group R of Formula Ia or II, optionally wherein the compound further comprises a V' and/or Y' group.

The compound comprising a moiety of interest Z comprising and a reactive group R' can have a structure of Formula III, below,

 Formula III where:

R' is a reactive group, e.g. a reactive group complementary for forming at least one bond with reactive group R of Formula Ia or II;

L' is a bond or a carbon comprising framework of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a bond or a continuation of a bond or a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety", Y' is independently absent, a bond or a continuation of a bond, or a spacer system (e.g., a self-eliminating spacer system or a non-self-elimination spacer system) which is comprised of 1 or more spacers;

Z is a moiety-of-interest, optionally a moiety that improves the pharmacokinetic properties, or a therapeutic moiety or a diagnostic moiety, and each Z is directly coupled to either Y or V when Y is absent, or L when both Y and V are absent;

q' and r' are an integer preferably from 1 to 4, representing degree of branching; and z' is an integer, preferably from 1 to 4.

Where Z is a reactive group, it can be a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment Z can be a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene.

Alternatively, in one of the embodiments of constructing multimeric polypeptides, the polypeptide having a functionalized acceptor glutamine of Formula Ib and a reactive group R' can have a structure of Formula Ib, below

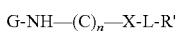 Formula Ib

The moiety R' is able to react with a suitable functional group R on a reaction partner, e.g. group R on the lysine-based linker of formula Ia or II. As discussed above, when the reactive moiety R' is designed to react with a reactive group R, a compound of Formula IV or V is formed.

The L group can be a carbon comprising framework of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process, wherein L' has r', q', and/or z' sites of attachment for the respective V', Y', and R' groups, where r' and q' represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

Also disclosed in one embodiment is a method comprising reacting a compound of Formula II with a compound for Formula III to obtain a compound of Formula IV. The method also includes reacting a compound (polypeptide) of Formula Ia with a compound (polypeptide) of Formula Ib to obtain a multimeric polypeptide of Formula V.

The Moiety Z

The moiety Z can be connected to Y or Y' or, when absent, to V or V', optionally via R or RR', with any suitable atom. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group). In one embodiment, Z is coupled in the compounds via a group such that its therapeutic abilities or diagnostic characteristics are, at least partly, blocked or masked. In case a compound is to be used for treating or preventing disease in an animal, e.g., a mammal, the Z moieties are generally therapeutic moieties. Where a compound is used to make a diagnosis or used in an ex vivo or in vivo diagnostic assay, the Z moieties are generally diagnostic moieties, for example chromogenic, fluorogenic, phosphorogenic, chemiluminescent, or bio luminescent compounds.

In one embodiment, the Z moiety is compound, preferably an organic compound, having a molecular weight of at least 300 g/mol, 400 g/mol, 500 g/mol, 600 g/mol, 700 g/mol, 800 g/mol, 900 g/mol, 1000 g/mol or 2000 g/mol.

In one embodiment, the Z moiety is a chemical compound displaying hydrophobic properties, optionally additionally having a molecular weight of at least 300 g/mol, 400 g/mol, 500 g/mol, 600 g/mol, 700 g/mol, 800 g/mol, 900 g/mol, 1000 g/mol or 2000 g/mol. Hydrophobic character may be determined, for example, by decreased water solubility, decreased polarity, decreased potential for hydrogen bonding, and/or an increased oil/water partition coefficient. The presently disclosed methods can be used to produce antibody conjugates where moiety of interest (Z) comprises a hydrophobic drug. As used herein, the term "hydrophobic" is a physical property of a molecule that is repelled from a mass of water. Hydrophobic compounds can be solubilized in nonpolar solvents, including but not limited to, organic solvents. Hydrophobicity can be conferred by the inclusion of apolar or nonpolar chemical groups that include, but are not limited to, saturated and unsaturated aliphatic hydrocarbon groups and such groups substituted by one or more aromatic, cycloaliphatic or heterocyclic group(s). Conversely, "hydrophilic" molecules are capable of hydrogen bonding with a water molecule and are therefore soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Hydrophobic molecules are poorly water soluble, for example, having a solubility of less than about 10 mg/ml. In some embodiments, the hydrophobic compound can have a solubility of less than about 1 mg/ml in water. In other embodiments, the hydrophobic compound has solubility in water of less than about 50, µg/ml, 10 µg/ml, and in particular embodiments, about 1 µg/ml or 2.5 µg/ml. In other embodiments, the hydrophobic compound can have a solubility of about 0.001 µg/ml to about 10 mg/ml, including but not limited to 0.001 µg/ml, 0.01 µg/ml, 0.1 µg/ml, 1 µg/ml, 2 µg/ml, 5 µg/ml, 10 µg/ml, 50 µg/ml, 100 µg/ml, 500 µg/ml, 1 mg/ml, 5 mg/ml, and 10 mg/ml, and any other concentration between 0.001 µg/ml and 10 mg/ml.

Representative, non-limiting examples of hydrophobic drugs that can be formulated using the presently disclosed methods include taxanes, e.g. paclitaxel (PTX), and camptothecin (CPT), maytansanoids, duocarmycins, pyrrolobenzodiazepines, dolastatins and auristatins. Such drugs are poorly soluble in water, e.g. PTX has a solubility in water of less than about 1 µg/ml, CPT has a water solubility of about 2.5 µg/ml. Linkers and modified antibodies can advantageously link hydrophobic drugs to antibodies.

In other embodiments, in view of hydrophobic drugs being poor substrates for TGase (in the absence of improved linkers or modified antibodies), the Z mioety may advantageously be a hydrophilic drug. Examples of hydrophilic drugs include amatoxins. Amatoxins are cyclic peptides composed of 8 amino acids as isolated from the genus Amanita. Amatoxins also include a range of chemical derivatives, semisynthetic analogs and synthetic analogs built from building blocks according to the master structure of the −5 natural compounds (cyclic, 8 aminoacids), synthetic or semisynthetic analogs containing non-hydroxylated amino acids instead of the hydroxylated amino acids, synthetic or semisynthetic analogs, in which the thioether sulfoxide moiety is replaced by a sulfide, sulfone, or by atoms different from sulfur, e.g. a carbon atom as in a carbaanalog of amanitin. Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or proteins. Amatoxins are described for example in European Patent publication no. 1859811, PCT publication nos. WO2010/115630 and WO2012/041504).

In one embodiment, the Z moiety is a large compound (e.g., molecular weight of at least 300 g/mol, 400 g/mol, 500 g/mol, 600 g/mol or 700 g/mol) comprising a polycyclic group, tricycle or one or more macrocycles. Such groups are often typical of hydrophobic and/or rigid structures. Examples of cytotoxic drugs that comprise a macrocycle (e.g. a ring of nine or more atoms) include maytansinoids, amatoxins, epothilones and taxanes. In one embodiment, the Z moiety comprises a ring of 9, 10, 11, 12, 13, 14, 15, 16, 17 or 18 atoms, or between 9 and 200 atoms. In one embodiment, the Z moiety is a chemical compound having a negative charge, optionally additionally displaying hydrophobic properties and/or having a molecular weight of at least 300 g/mol, 400 g/mol, 500 g/mol, 600 g/mol, 700 g/mol, 800 g/mol, 900 g/mol, 1000 g/mol or 2000 g/mol.

When more than one Z moiety is connected to a self-elimination spacer system Y or Y', at least one Z should be released upon self-elimination of Y or Y'. The moiety Z initially released may be a moiety that is not a fully active moiety itself. In other words, Z may be a moiety that has limited diagnostic or therapeutic abilities, e.g. a moiety that acts as a prodrug. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

In one aspect, a Z moiety may be a backbone (e.g. polymer) to which a plurality of drugs or diagnostic moieties are linked. For example, Z may be a polyacetal- or polyacetal derivative-based polymer comprising a plurality of drug molecules, see, e.g., Yurkovetskiy et al. (2004) Mol. Pharm. 1(5): 375-382 and WO 2011/120053, the disclosures of which are incorporated herein by reference; for example Z may be a polymer compound of Formula I of WO 2011/120053 comprising a plurality of cytotoxic anti-cancer agents.

In one aspect, one or more moieties Z are each selected from a therapeutic or diagnostic agent. In another embodiment, one or more moieties Z are each a therapeutic agent. In yet another embodiment, the moieties Z each are the same therapeutic moiety. In yet another embodiment, the moieties Z comprise at least two different therapeutic moieties.

The moiety Z includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In one embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent, preferably a cytotoxic anti-cancer agent.

In another embodiment, the one or more moieties Z are each an anticancer agent. In a further embodiment, the one or more moieties Z are each a hydroxyl-containing anticancer agent.

In one embodiment, Z is an alkylating agent, preferably a DNA alkylating agent. An alkylation agent is a compound that can replace a hydrogen atom with an alkyl group under physiological conditions (e.g. pH 7.4, 37 C, aqueous solution). Alkylation reactions are typically described in terms of substitution reactions by N, O and S heteroatomic nucleophiles with the electrophilic alkylating agent, although Michael addition reactions are also important. Examples of alkylating agents include nitrogen and sulfur mustards, ethylenimines, methanosulfonates, CC-1065 and duocarmycins, nitrosoureas, platinum-containing agents, agents that effectuate Topoisomerase II-mediated site dependent alkylation of DNA (e.g. psorospermin and related bisfuranoxanthones), ecteinascidin and other or related DNA minor groove alkylation agents.

In one embodiment, Z is a DNA minor groove binding and/or alkylating agent, e.g., a pyrrolobenzodiazepine, a duocarmycin, or derivatives thereof.

In a further embodiment, the one or more moieties Z are each independently selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)amino)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetyl-spermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, tubulysin A, tubulysin D, carminomycin, streptonigrin, elliptmium acetate, maytansine, maytansinol, calicheamycin, mertansine (DM1), N-acetyl-$\gamma_1{}^I$-calicheamycin, calicheamycin-$\gamma_1{}^I$, calicheamycin-$\alpha_2{}^I$, calicheamycin-$\alpha_3{}^I$, duocarmycin SA, duocarmycin A, CC-1065, CBI-TMI, duocarmycin C2, duocarmycin B2, centanamycin, dolastatin, auristatin E, monomethylauristatin E (MMAE), monomethylauristatin F (MMAF), α-amanitin, β-amanitin, γ-amanitin, ε-amanitin, amanin, amaninamide, amanullin, and amanullinic acid and derivatives thereof.

Exemplary auristatin embodiments include the N-terminus linked monomethylauristatin drug moieties comprising a structure of any of Formulas V and VI below:

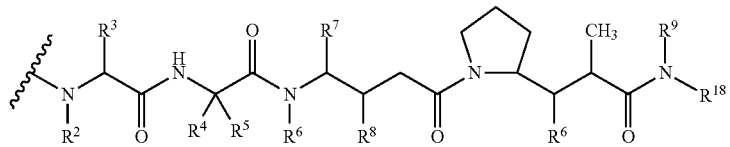

Formula V

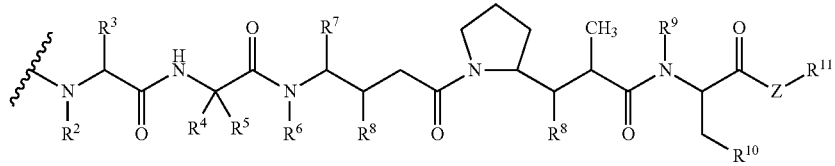

Formula VI wherein the wavy line of V and VI indicates the covalent attachment site to a L, L', V, V', Y, Y', (RR'), R' or $(C)_n$ group of a compound (e.g. a compound of Formula I, II or IV), and independently at each location:

$R^2$ is selected from H and $C_1$-$C_8$ alkyl;

$R^3$ is selected from H, $C_1$-$C_8$ alkyl, $C_1$-$C_8$ carbocycle, aryl, $C_1$-$C_8$ alkyl-aryl, $C_1$-$C_8$ alkyl-($C_3$-$C_8$carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle. aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula $-(CR^aR^b)_n-$ wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$ wherein $R^{12}$ is $C_1$-$C_8$ alkyl;

$R^{11}$ is selected from H, $C_1$-$C_{20}$ alkyl, aryl, C3-C8 heterocycle, $-(R^{13}O)_m-R^{14}$, or $-(R^{13}O)_m-CH(R^{15})_2$; m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, $-(CH_2)_n-N(R^{16})_2$, $-(CH_2)_n-SO_3-C_1$-$C_8$ alkyl;

each occurrence of $R^{16}$ is independently H, $C_1$-$C_8$ alkyl, or $-(CH_2)_n-COOH$;

$R^{18}$ is selected from —C($R^8$)$_2$—C($R^8$)$_2$-aryl, —C($R^8$)$_2$—C($R^8$)$_2$—(C$_3$-C$_8$ heterocycle), and —C($R^8$)$_2$—C($R^8$)$_2$—(C$_3$-C$_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment. $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —CH($R^{15}$)$_2$, wherein $R^{15}$ is —(CH$_2$)$_n$—N($R^{16}$)$_2$, and $R^{16}$ is —C$_1$-C$_8$ alkyl or —(CH$_2$)$_n$—COOH.

In another embodiment, when Z is —NH, $R^{11}$ is —CH($R^{15}$)$_2$, wherein $R^{15}$ is —(CH$_2$)$_n$—SO$_3$H.

One exemplary auristatin embodiment of formula V is MMAE, wherein the wavy line indicates the covalent attachment to a L, L', V, V', Y, Y', (RR'), R' or (C)$_n$ group of a (e.g. a compound of Formula I, II or IV):

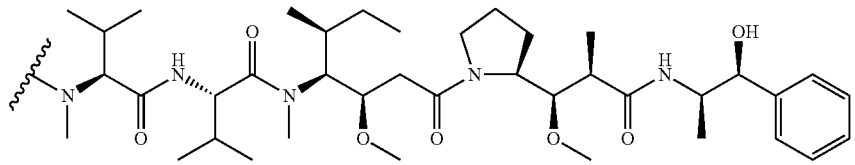

MMAE

An exemplary auristatin embodiment of formula VI is MMAF, wherein the wavy line indicates the covalent attachment to a linker (L) of an antibody-drug conjugate (see US 2005/0238649 and Doronina et al. (2006) Bioconjugate Cfiem. 17: 1 14-124):

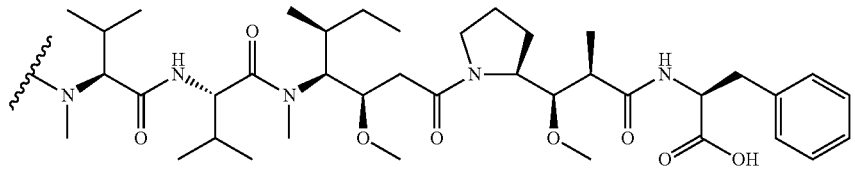

MMAF

Other exemplary Z embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a L, L', V, V', Y, Y', (RR'), R' or (C)$_n$ group of a compound (e.g. a compound of Formula I, II or IV):

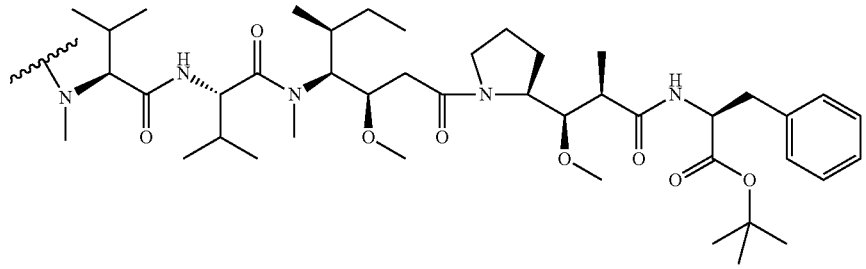

-continued
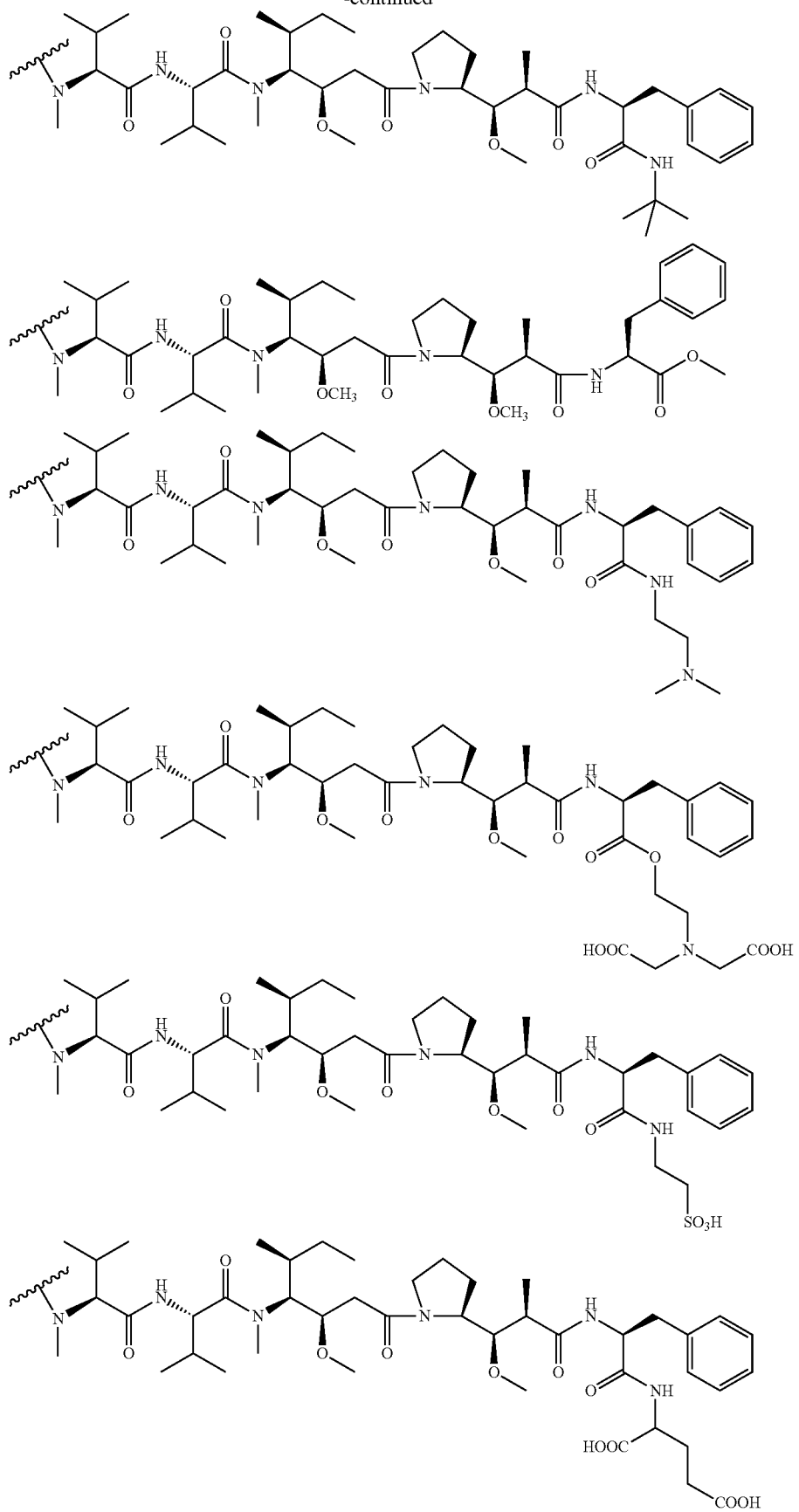

-continued

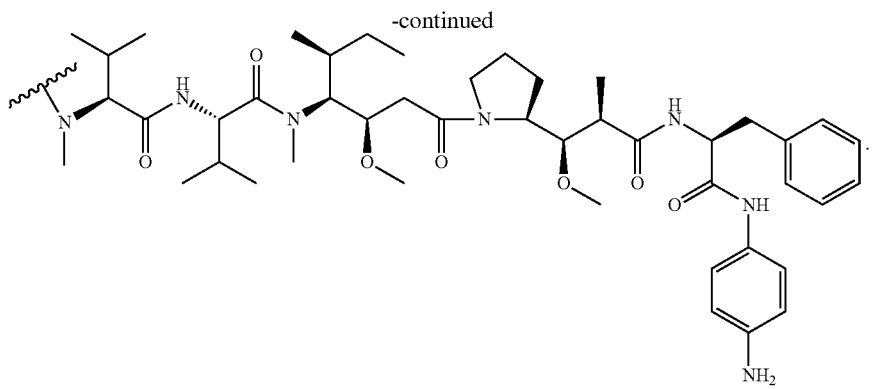

An example of a linker comprising a lysine residue as $(C)_n$ moiety, a valine-citrulline as the (V) moiety, a PAB as the (Y) moiety together with a MMAF as the (Z) moiety is shown below (corresponding to compound Ia-1):

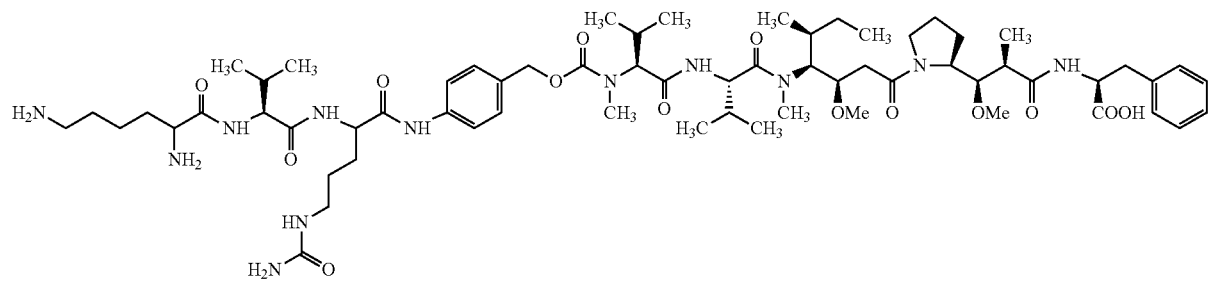 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)C(N)CCCCN)C(C)C)cc1)C(C)C]

In one embodiment, the Z moiety is an epothilone or epothilone derivative. An epothilone is a cyclic molecule with a 16-membered ring and variable substituents and pharmaceutical activity as a cytostatic agent that binds to tubulin. Various epothilone derivatives are known, including variants with 14-, 15- or 18-membered rings have also been developed (e.g. WO2011085523; WO2009105969). Examples of epothilones or epothilone analogs or derivatives include epothilone A, epothilone B, epothilone C, 13-alkyl-epothilone C derivatives, epothilone D, trans-epothilone D, epothilone E, epothilone F, an effector conjugate of epothilone, Sagopilone, or any of the epothilones referred to in the literature as ixabepilone (BMS-247550), BMS-310705, EPO-906, Patupilone, Kos-862, Kos-1584, Kos-1803 and ABJ 879, and pharmaceutically active salts thereof. The production of epothilones, their precursors and derivatives is generally carried out according to the methods known to one skilled in the art. Suitable methods are, for example, described in DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. No. 6,204,388, U.S. Pat. No. 6,387,927, U.S. Pat. No. 6,380,394, US 02/52028, US 02/58286, US 02/62030, WO 02/32844, WO 02/30356, WO 02/32844, WO 02/14323, and WO 02/8440. Further epothilones are described in WO 93/10102, WO 98/25929, WO 99/02514, WO 99/07692, WO 99/02514, WO 99/67252, WO 00/49021, WO 00/66589, WO 00/71521, WO 01/027308, WO 02/080846, WO 03/074053, WO 2004/014919.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$AU, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in PCT publication no. WO 92/22583); and polyamides, especially desferriox-amine and derivatives thereof.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerytbrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof. Such compounds, when used as a moiety Z can be employed as a moiety that improves the pharmacokinetic properties of the antibody.

The size of the polymer may be varied as desired, but will generally be in an average molecular weight range from 500 Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

In another embodiment, z' equals 1, each V, Y or V—Y (including whether any V and Y is a V' or Y') moiety contains a single attachment site for a functional group of Z.

In another embodiment, a one V (or V'), Y, (or Y') or V—Y (or V'—Y', V—Y') moiety is attached to more than one Z moiety via multiple functional groups R on the said V, Y or V—Y moiety. Optionally, the one or more V (or V') moieties comprise a polymer, optionally an oligoethylene glycol or a polyethylene glycol or a derivative thereof.

In one embodiment, Z is any suitable polypeptide. The protein or peptide sometimes may optionally be a subregion of a protein, such as in the N-terminus, C-terminus, extracellular region, intracellular region, transmembrane region, active site (e. g., nucleotide binding region or a substrate binding region), a domain or a post-translationally modified region (e. g., phosphorylated, glycosylated or ubiquinated region), for example. Peptides often are 50 amino acids or fewer in length (e. g., 45, 40, 35, 30, 25, 20, or 15 amino acids or fewer in length) and proteins sometimes are 100 or fewer amino acids in length, or 200, 300, 400, 500, 600, 700, or 900 or fewer amino acids in length. The protein or peptide sometimes includes the modification moiety or a portion thereof (e. g., the glycosyl group or a portion thereof). In certain embodiments, the protein is a signal transduction factor, cell proliferation factor, apoptosis factor, angiogenesis factor, or cell interaction factor. In one embodiment, the polypeptide is an antibody, e.g., a dimeric or tetrameric antibody, a full-length antibody, a single chain antibody (e.g. an scFv, an affibody, a $V_H$ domain, a $V_L$ domain, a V-NAR domain or a $V_HH$ domain).

Polypeptide Conjugates

The polypeptide conjugates resulting from the reaction of the compounds of Formula Ia, Ib or Ic will yield a polypeptide conjugate in which a moiety Z is connected to linker L (or L') when Y (or Y') and V (or V') are absent, to the spacer system Y (or Y') or, when Y (or Y') is absent, to V (or V'). Optionally said connections are via linking group (RR') of M.

The conjugates resulting from the reaction yield a polypeptide which is conjugated (i.e., covalently attached) via an acceptor glutamine residue (Q) present within a TGase recognition tag in (e.g., introduced to) the polypeptide to a NH group of a lysine-based linker, and one or more moieties (Z) through optional linking group (RR'), optional linker (V or V') and/or optional spacer (Y or Y').

In one embodiment, the (RR') remain present in a conjugated polypeptide, in which case a Formula IV will comprise an M moiety. Such a polypeptide comprises a TGase recognition tag comprising a functionalized glutamine residue (Q) of Formula IV, below,

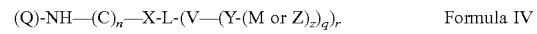

$$(Q)\text{-NH}-(C)_n-X-L-(V-(Y-(M \text{ or } Z)_z)_q)_r \quad \text{Formula IV}$$

where:

Q is glutamine residue TGase recognition tag present in (e.g. introduced to) an antibody;

$(C)_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide (e.g. a O, N or S atom of an ether, ester, thioether, thioester, amine, alkylamine, amide, or alkylamide);

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;

q is an integer selected among 1, 2, 3 or 4;

z is an integer selected among 1, 2, 3 or 4; and

V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and M is independently: R or (RR')-L'-(V'—(Y'—(Z)$_z$)$_{q'}$)$_{r'}$, wherein each of L', V', Y', z', q', and r' are as defined in Formula III (or are defined as L, V, Y, z, q and r, respectively, Z is a moiety-of-interest, optionally a moiety that improves the pharmacokinetic properties, or a therapeutic moiety or a diagnostic moiety. Optionally where the compound of formula IV is a multimeric polypeptide, Z is a polypeptide. Optionally Z is an antibody (e.g. a single chain antibody, an scFv, an affibody, a V$_H$ domain, a V$_L$ domain, a V-NAR domain or a V$_H$H domain). Optionally both Z and the polypeptide comprising the TGase recognition tag are antibodies (e.g. a single chain antibody, an scFv, an affibody, a V$_H$ domain, a V$_L$ domain, a V-NAR domain or a V$_H$H domain).

Figure 2:
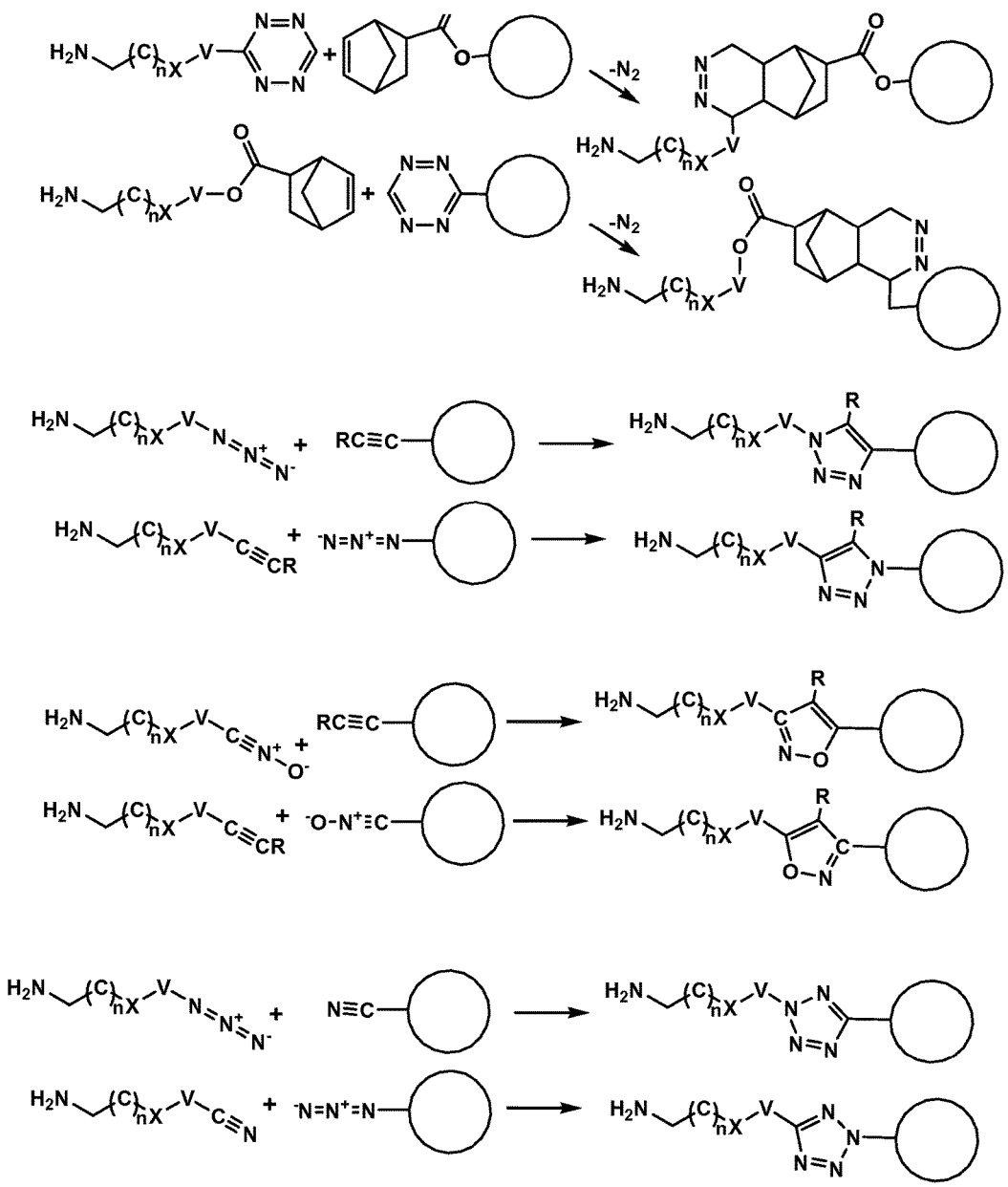
FIG. 2 shows reaction schemes for Diels-Alder cycloadditions and click reactions where the reactive groups of linking reagents combine with complementary reactive group attached to an agent including a therapeutic, diagnostic, or other moiety.
Figure 3:
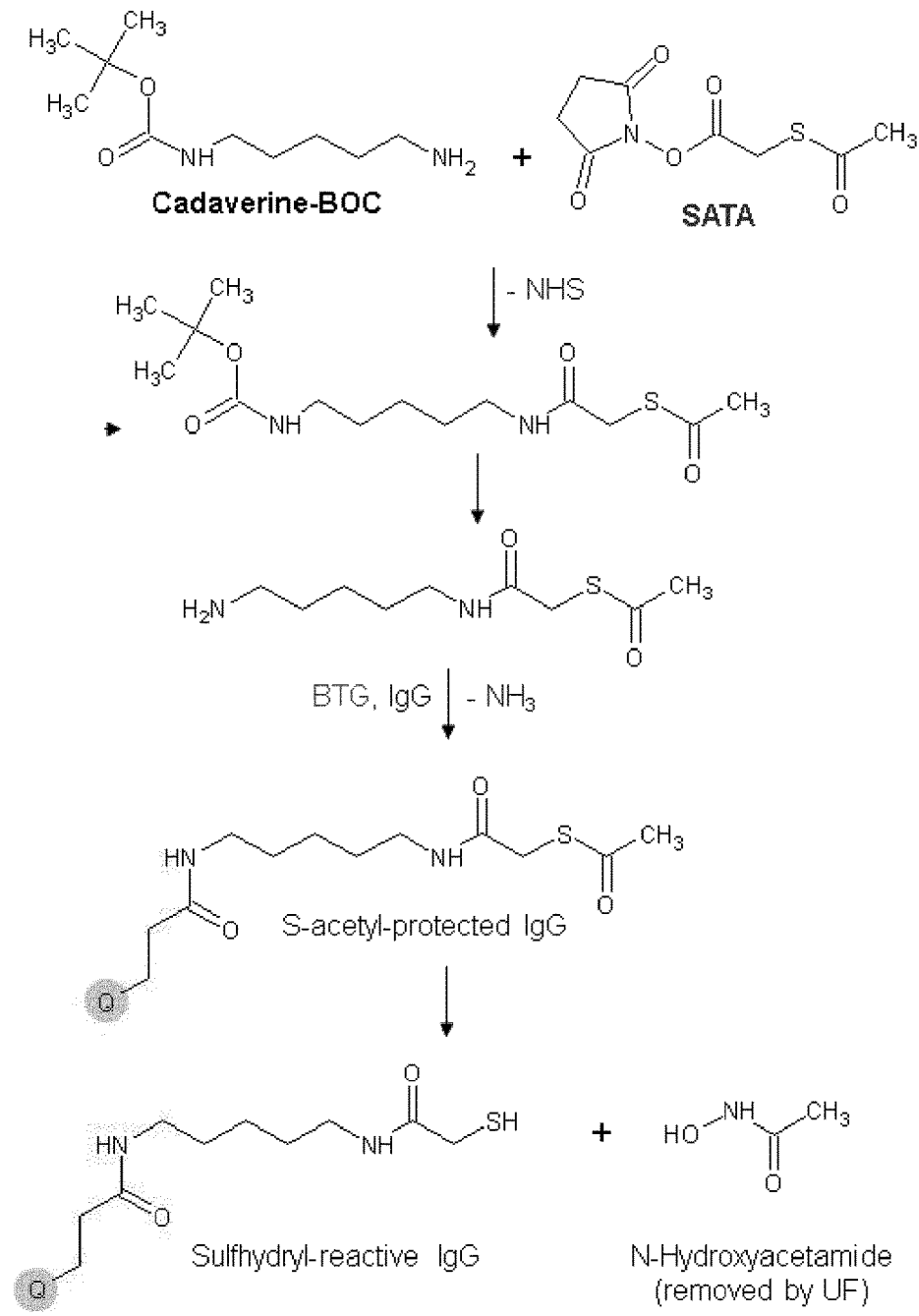
FIG. 3 shows the preparation of an exemplary linking reagent, according to an embodiment, and its conjugation with a protein, where: V and Y are absent, R is a thiol (sulfhydryl) reactive group that is ultimately generated from the S-acetyl protected thiol, $SC(O)CH_3$; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 4:
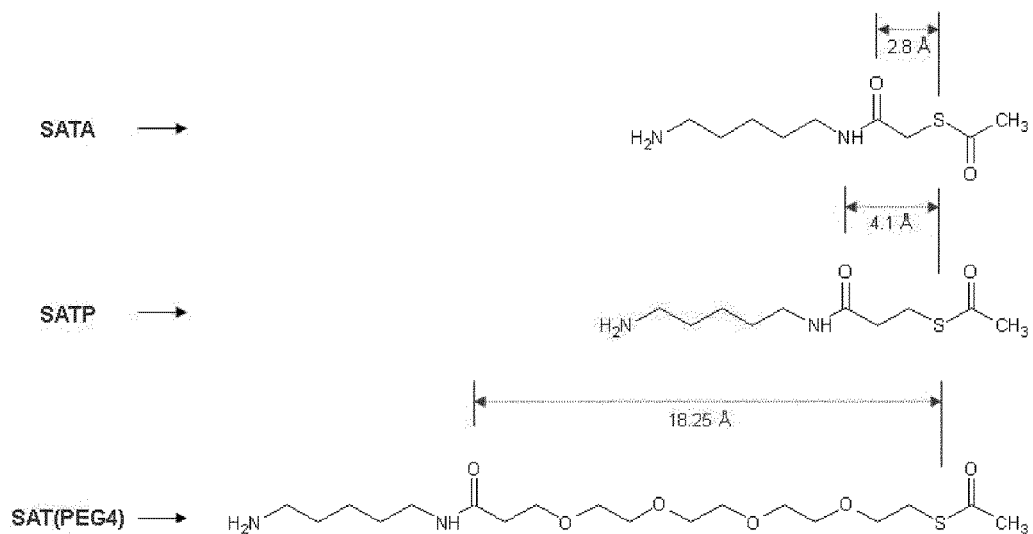
FIG. 4 illustrates the preparation of various exemplary linking reagents, according to various embodiments, with a single S-acetyl protected thiol reactive group that can be prepared from an N-succinimidyl-S-acetylthioester reagent.
Figure 5:
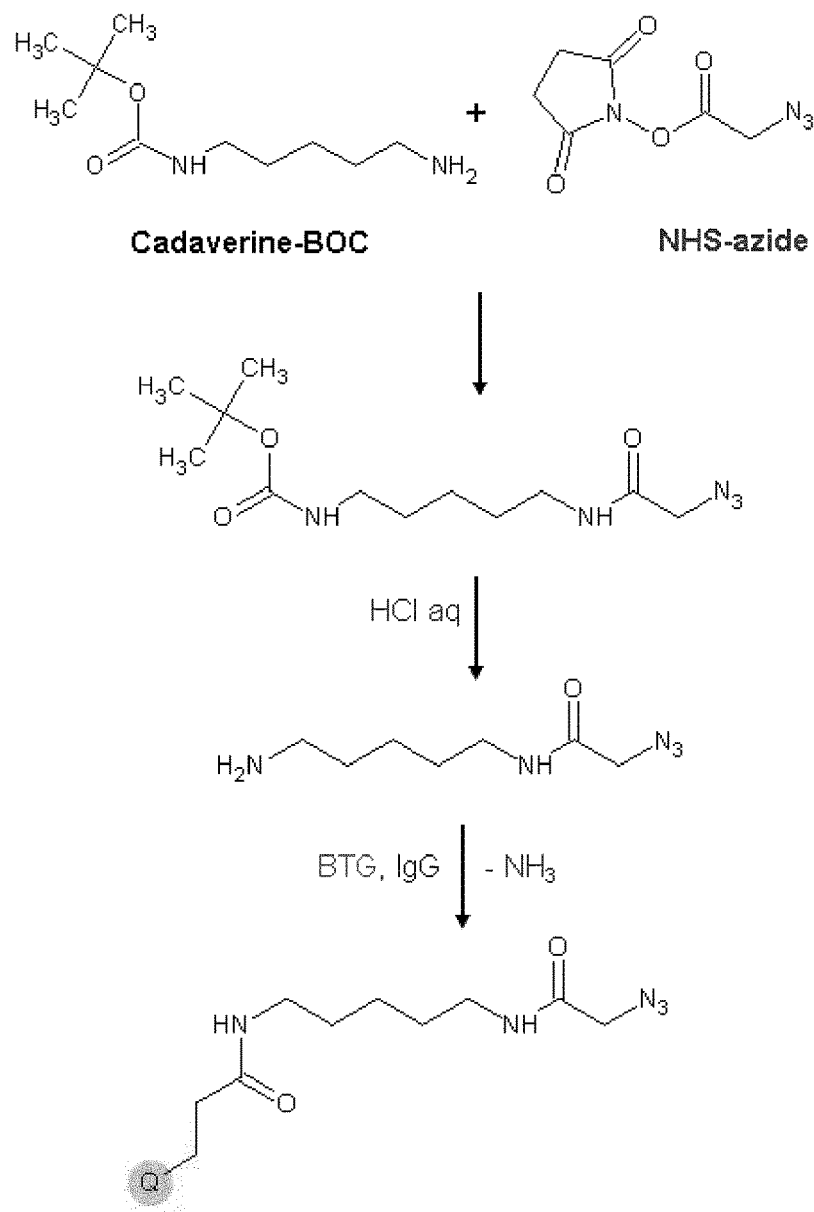
FIG. 5 illustrates the preparation of an exemplary linking reagent, according to an embodiment, and its conjugation with a protein, where: V and Y are absent, R is an azide reactive group; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 6:
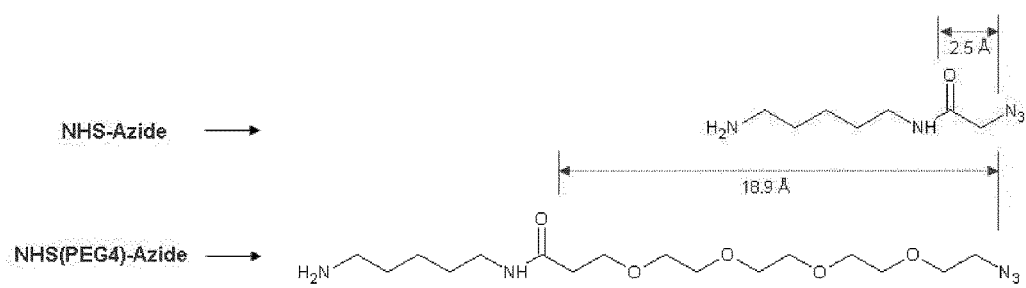
FIG. 6 illustrates the preparation of various exemplary linking reagents, according to embodiments, with a single azide reactive group that can be prepared from an N-succinimidyl-azide reagent.
Figure 7:
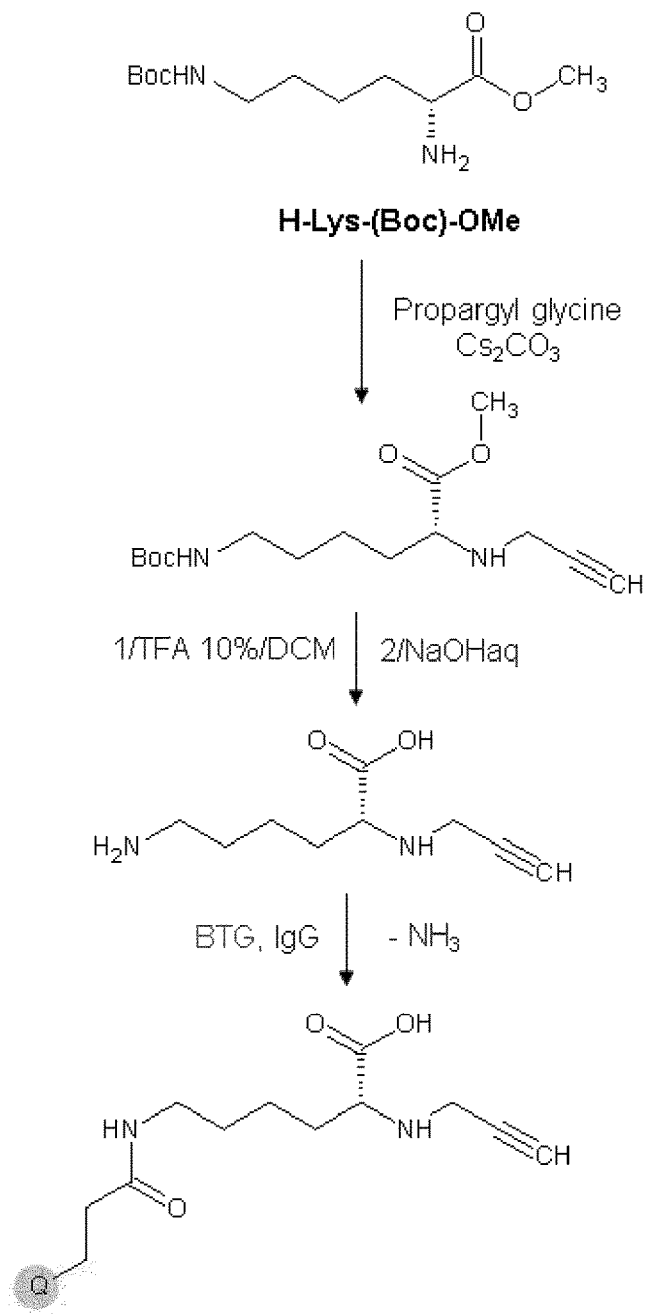
FIG. 7 depicts the preparation of an exemplary linking reagent, according to an embodiment, and its conjugation with a protein, where: V and Y are absent, R is an alkyne reactive group; r is 0; q is 0; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 8:
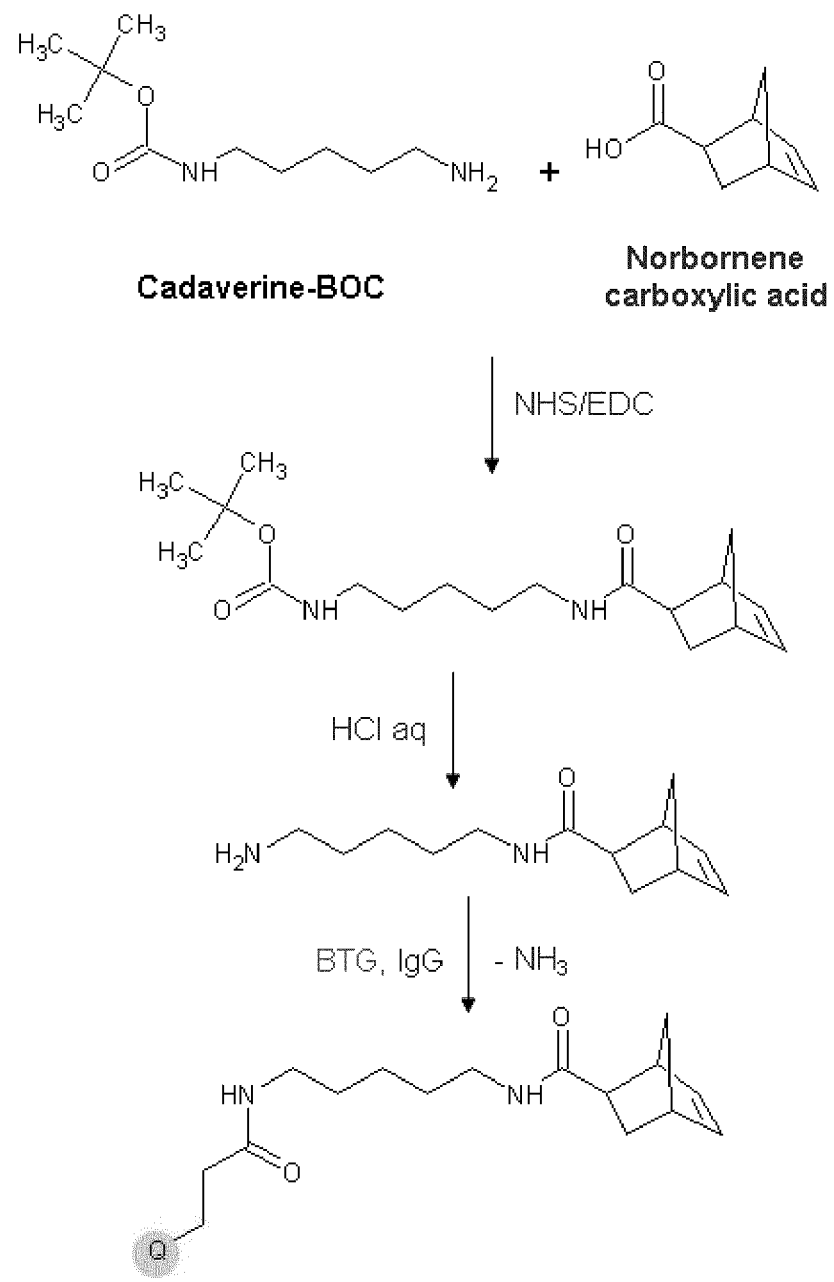
FIG. 8 shows the preparation of an exemplary linking reagent, according to an embodiment, and its conjugation with a protein, where: R is a norbornene reactive group; r is 0; q is 0; z is 1; L is the one carbon comprising framework C(O); X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.

R is as defined in Formula I and wherein each (RR') is an addition product between an R of Formula I and its complementary R' of Formula III (see, for example, FIG. 1 and FIG. 2).

Thus, RR' can be for example an addition product of a thio-maleimide (or haloacetamide) addition, for example, a N,S-disubstituted-3-thio-pyrrolidine-2,5-dione; Staudinger ligation, for example, a N,3- or N,4-substitued-5-dipenyl-phosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, 0 or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Optionally, the antibody conjugate comprises a group (RR') representing the remainder of a reactive moiety R when R has reacted with a reactive moiety R', wherein the group (RR') connects (a) an L to a Z, a V or a Y, (b) a V to a Z or a Y, or (c) a Y to a Z. For example, any V, Y and/or Z may be characterized as comprising a (RR') group. Any L, V, Y may be an L', V' or Y', respectively.

It will be appreciated that Formula IV can for convenience also be expressed as (Ab)-NH—(C)$_n$—X-L-(V—(Y-(M)$_z$)$_q$)$_r$, where (Ab) is an immunoglobulin (Ab) is conjugated via a glutamine (Q) residue to an NH of the linking reagent (e.g the compound of Formula Ia).

FIG. 9B shows exemplary lysine based linking compounds, for coupling to lysine-based linker-vc-PAB-MMAF (MMAF with a cleavable linker) and mAb coupled to lysine-based linker -MMAF (MMAF with a non cleavable linker).

In one embodiment, a multimeric polypeptide is formed by reacting two polypeptides each functionalized with a lysine based linker within a TGase recognition tag. The multimeric polypeptide can be described as comprising a first polypeptide and a second polypeptide each comprising a TGase recognition tag, wherein the first polypeptide and a second polypeptide are linked to one another through a functionalized acceptor glutamine residue (Q) of Formula V, below, $$(Q_{pp1})\text{-NH}-(C)_n-\text{X-L-RR'-L-X}-(C)_n-\text{NH-}(Q_{pp2}) \quad \text{Formula V}$$

where:

$Q_{pp1}$ is a glutamine residue present in a TGase recognition tag of the first polypeptide (e.g. single chain antibody);

$Q_{pp2}$ is a glutamine residue present in a TGase recognition tag of the first polypeptide (e.g. single chain antibody); and (C)$_n$, n, X, L and RR' are defined as in Formula IV.

Evaluating the Polypeptides

Once polypeptide conjugates (e.g., as antibody samples comprising antibody conjugates) have been obtained, they will generally be assessed for a characteristic of interest. In some embodiments, activity assays and/or other assays will be performed in order to characterize the conjugates. In some embodiments, cell binding, affinity, and/or cytotoxicity assays will be performed. The characteristic that is assessed can be a property mediated by the polypeptide(s), e.g., variable region(s) of the antibody(ies), and/or by the moiety-of-interest (Z).

In one example, the antibody conjugates can be assessed (e.g. compared) for their ability to bind to, inhibit the proliferation of, or, preferably, kill, target cells, e.g. using a cytotoxicity assay. Particularly, where moiety Z is a cytotoxic drug, the efficacy of the antibody as antibody-drug conjugates can be evaluated, e.g. as the ability of the antibodies to cause the death of tumor cells, infected cells, or generally any suitable target cells that express the antigen for which the antibody is specific.

In other example, moiety Z is a moiety that improves the pharmacokinetic properties of the antibody, and the pharmacokinetic properties of the antibody can be evaluated. In one embodiment, the pharmacokinetic property evaluated is stability of the antibody in a suitable environment, e.g. blood, pharmaceutical formulation, etc.

In one example, multimeric polypeptides can be evaluated for the ability of a first and second polypeptide (e.g. antibody) in the multimer to bind to a predetermined binding partner. For example, the respective antibodies in a bi- or multi-specific antibody can be evaluated for their binding to a predetermined antigen of interest. Likewise bi- or multi-specific antibodies can be assessed (e.g. compared) for their ability to inhibit the proliferation of, or, preferably, kill, target cells, e.g. using a cytotoxicity assay, or to induce or block any desired biological function or antigen-ligand interaction.

In general, well-known assays for detecting polypeptide binding (e.g antibody binding to antigens), including competition-based assays, ELISAs, radioimmunoassays, Western blotting, BIACORE-based assays, and flow cytometry assays, can be equally applied to detect the interaction of antibodies, such as cytotoxic antibodies, with their target cells. Typically, target cells will be tumor or cancer cells.

Also provided are methods for screening polypeptides (e.g. antibodies). In one embodiment, provided is a method for making, evaluating and/or screening polypeptides, comprising the steps of:

a) providing a first and second polypeptide (e.g., antibody) sample each comprising a plurality of polypeptides comprising a TGase recognition tag, wherein the first and second polypeptide-containing samples differ from one another with respect to antibody quantity and/or polypeptide sequence (e.g. variable region sequence, CDR sequence(s)), wherein substantially all of the polypeptide present in the first sample is of the same sequence and substantially all of the polypeptide present in the second sample is of the same sequence; and b) reacting each of said first and second polypeptide sample with a lysine-based linker, in the presence of a TGase, under conditions sufficient such that antibodies in such first and second polypeptide samples are conjugated to a lysine-based linker.

Optionally, the first and second polypeptide samples in step b) are reacted in separate containers.

Optionally, the first and second polypeptide samples are specific for the same antigen.

Optionally, the conjugated polypeptides obtained in step b) are conjugated to a moiety-of-interest (Z) via said lysine-based linker.

In one embodiment, step b) comprises: generating a library (e.g. from a phage display library) comprising a plurality of polypeptides, which plurality comprises a first and a second polypeptide sample (or 5, 10, 100 or more further samples), wherein said first and second (or further) samples each comprise a different polypeptide comprising a TGase recognition tag, optionally wherein the tag is a myc tag or an amino acid sequence derived from a myc tag, optionally wherein the polypeptides are antibodies (e.g. antibody fragments, an affibody, an scFv, a $V_H$ domain, a $V_L$ domain, a V-NAR domain or a $V_HH$ domain), optionally antibodies comprising a myc tag or an amino acid sequence derived from a myc tag fused to their N- or C-terminus.

In one embodiment, step b) comprises: reacting each of said first and second polypeptide sample with a lysine-based linker comprising a moiety-of-interest (Z) (e.g. a linker of Formula Ic), in the presence of a TGase, under conditions sufficient such that polypeptides in such first and second polypeptide samples are conjugated to a lysine-based linker comprising a moiety-of-interest (Z).

In one embodiment, step b) comprises:

(i) reacting each of said first and second polypeptide sample with a lysine-based linker comprising a reactive group (R) (e.g. a compound of Formula Ia) such that polypeptides in such first and second polypeptide samples are conjugated to such lysine-based linker comprising a reactive group (R) (e.g. an antibody of Formula II), and (ii) further reacting the resulting first and second polypeptide samples of step (i) (e.g. an antibody of Formula II) with a compound comprising: (a) a reactive group (R') that reacts with reactive group (R) on the lysine based linker, and (b) a moiety-of-interest (Z) (e.g., a compound of Formula III), whereby the resulting antibodies in such first and second polypeptide samples are conjugated to a lysine-based linker comprising a moiety-of-interest (Z) is obtained (e.g. an antibody of Formula IV).

The antibodies and polypeptide-conjugates identified using the evaluation methods can then be used for the manufacture of a pharmaceutical preparation and/or for the treatment or diagnosis of a mammal being in need thereof. One embodiment relates to the use of any of the compounds defined above for the manufacture of a pharmaceutical composition and/or for the treatment of a tumor or cancer in a mammal.

Any of the compounds defined above can be used as a medicament or an active component or active substance in a medicament. One aspect relates to a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

One aspect relates to a method to affect or prevent a predefined condition by exerting a certain effect, or detect a certain condition using a compound of the disclosure, or a (pharmaceutical) composition comprising a compound of the disclosure.

One aspect relates to a method of treating a mammal being in need thereof, whereby the method comprises the administration of a pharmaceutical composition to the mammal in a therapeutically effective dose.

One aspect relates to a method of treating a mammal having an illness characterized by undesired (cell) proliferation with a compound of the disclosure. In another embodiment this disclosure relates to a method of treating a mammal carrying a tumor with a compound disclosed herein. In yet another embodiment this disclosure relates to a method of treating a mammal having an inflammatory disease with a compound disclosed herein. In yet another embodiment this disclosure relates to a method of treating a mammal having an autoimmune disease with a compound disclosed herein. In yet another embodiment this disclosure relates to a method of treating a mammal having a bacterial or viral infection with a compound disclosed herein.

In one embodiment, the disclosure relates to a method of treating cancer in a mammal, whereby the method comprises the administration of a pharmaceutical composition to the mammal in a therapeutically effective dose.

In one embodiment, the compound of the disclosure is capable of being internalized into cells that express an antigen to which the antibody binds (e.g. a tumor or viral antigen) and/or induces internalization of the antigen on said antigen-expressing cells. In one embodiment, the compound of the disclosure is toxic to a cell upon internalization (i.e. the compound comprises a moiety Z that is toxic to a cell). Preferably such compounds can be used in methods of killing or eliminating cells, preferably wherein said cells are tumor cells.

The disclosure also relates to pharmaceutical compositions comprising the compounds of the disclosure as defined above. A compound may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

EXAMPLES

Example 1: BTG-Mediated Coupling of Substrates to Single Chain Antibodies Via MYC Tags Materials and Methods
  Materials:
  Recombinant proteins: scFv (myc-tagged); affibody (dimeric, myc-tagged); nanobody (myc-tagged; non-tagged). Ligands: biotin-cadaverine (Zedira); desferrioxamine (Sigma Aldrich). Enzyme: MTGase (Zedira). Myc-Tag sequence: EQKLISEEDL (SEQ ID NO: 1)

Enzymatic Modification of Recombinant Protein 1 mg/mL recombinant protein in PBS was incubated with 80 equivalents of ligand and 1 U/mL or >1 U/mL bacterial transglutaminase (BTGase, Zedira, Darmstadt, Germany) overnight at 37° C. Excess of ligand and the BTGase were removed by centrifugation-dialysis (Vivaspin MWCO 50 kDa, Vivascience, Winkel, Switzerland).

LC-MS Analysis

LC-MS analysis was performed on a Waters LCT Premier mass spectrometer. Samples were chromatographed on an Uptisphere 5BP1#15QS C18, 150×2 mm column heated to 40° C. using a linear gradient from 20 to 80% A in 20 min plus 5% solvent C (solvent A: acetonitrile+0.1% formic acid, solvent B: water+0.1% formic acid, solvent C: 2-propanol) at a flow rate of 0.5 mL/min. The eluent was ionized using an electrospray source. Data were collected with MassLynx 4.1 and deconvolution was performed using MaxEnt1. Before the LC-MS analysis, 10 μg of antibody were mixed with DTT (final concentration should be 20 mM). Guan-buffer (7.5M Guan-HCl, 0.1M Tris-HCl, 1 mM EDTA buffer pH 8.5 (adjusted by addition of concentrated $NH_4OH$ (28% aqueous solution) was added to a final volume of 50 μL. Finally, 5 μL of the mixture were injected.

Western Blot Analysis

Western blot analysis: Enzymatically modified antibodies were subjected to SDS-PAGE (12.5%) and were transferred to polyvinylidene difluoride (PVDF) membranes (Immobilon P, Millipore). After blocking with 2% bovine serum albumin (BSA) in TBST (20 mM Tris-HCl, pH 7.5, 140 mM NaCl, 0.05% Tween-20) for 2 hours at room temperature (RT), membrane was incubated with Streptavidin-horseradish peroxidase conjugate (High Sensitivity Streptavidin-HRP diluted 1:20000; Beckman Coulter) for 30 min. Membrane was washed three times with TBST for 15 min and antibodies were detected with Immune-Star Western C Kit chemiluminescence substrate from Biorad.

Tryptic Digest $6.67*10^{-9}$ mol protein was incubated in 100 μl 50 mM ammonium bicarbonate pH 8.0 containing 0.1% Rapidgest SF (Waters) and 0.96 μl 1M DTT at 55° C. for 30 min. After the sample was cooled to RT. 1.92 μl 1M iodoacetamide was added and the samples were incubated for 40 min at RT. The samples were then digested with 5 μg trypsin over night at 37° C. and diluted (1:1 v/v) with 1% formic acid in 10% acetonitrile and analysed by ESI-TOF LC-MS using a ACE 3 C18, 150×3 mm column.

Results

1. Modification of a Nanobody with Biotin-Cadaverin.

Figure 14:
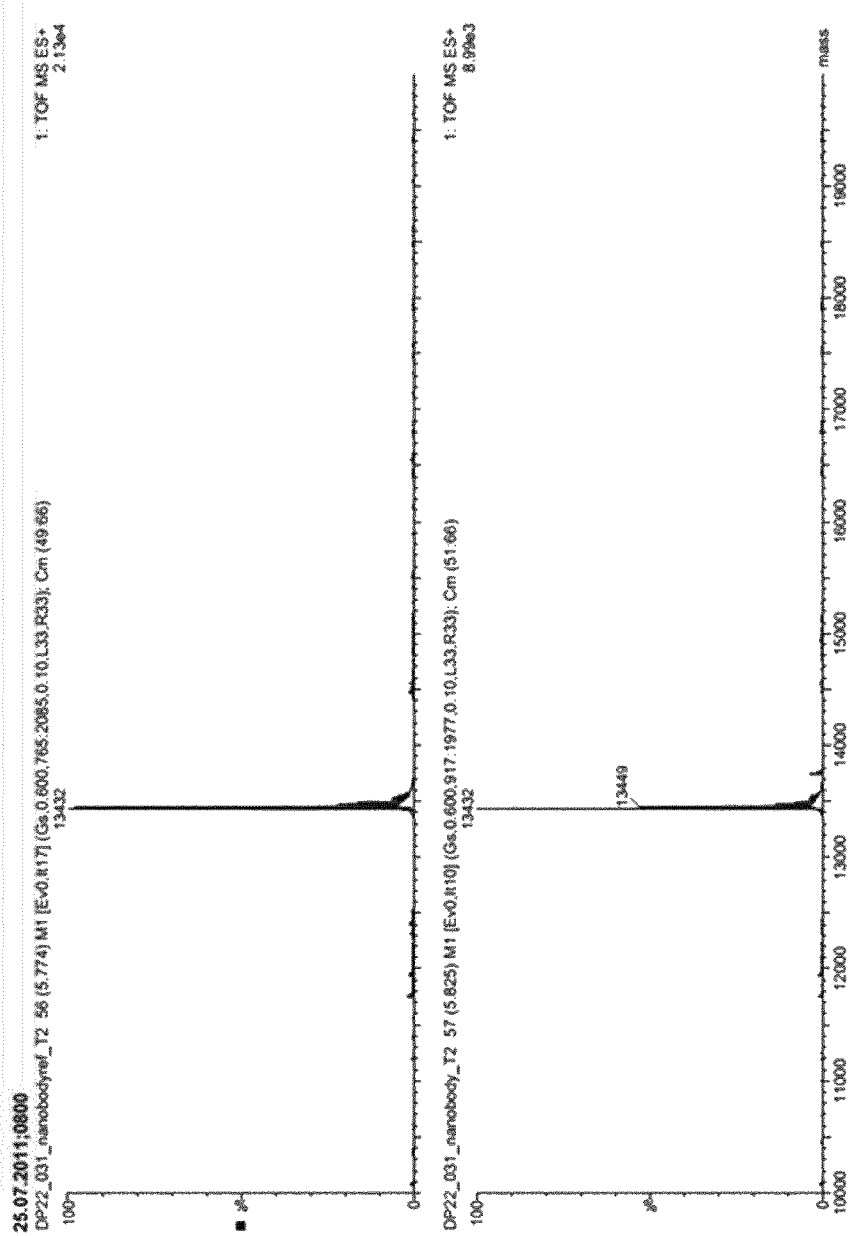
FIG. 14 shows LC-MS analysis of untagged nanobody incubated with MTGase (top) or MTGase and biotin-cadaverine (bottom).

In order to assess potential acceptor glutamines, a recombinant nanobody (camelid-derived single VH domain) was incubated with MTGase and biotin-cadaverin, and results were analysed by LC-MS. Analysis of the conjugates revealed lack of substantial labeling of the untagged nanobody (FIG. 14). Thus, MTG does not functionalize glutamines present within the backbone of the nanobody.

Figure 15:
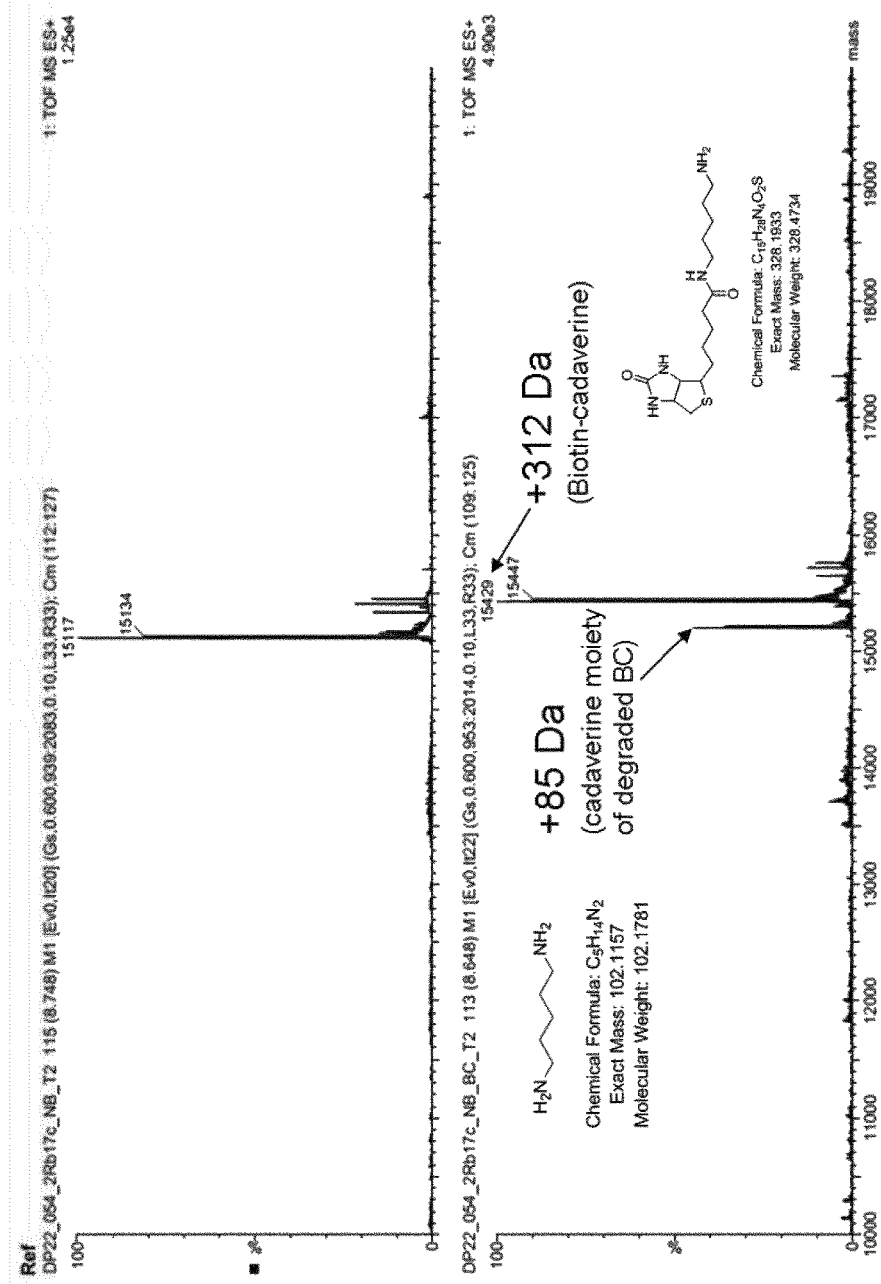
FIG. 15 shows LC-MS analysis of myc-tagged nanobody incubated with MTGase (top) or MTGase and biotin-cadaverine (bottom).

In contrast, LC-MS analysis revealed that the enzymatic reaction resulted in modification of the same nanobody carrying a C-terminal myc-tag (FIG. 15). The mass peak at 15429 has the correct mass shift of 312 Da. Thus, MTG functionalizes the unique glutamine present within the myc-tag sequence. After tryptic digest, a peptide with the correct mass including the biotin-modified glutamine could be identified (Table 1).

2. Modification of a Single Chain Variable Fragment (scFv) with Biotin-Cadaverin.

A myc-tagged scFv was incubated with MTGase and biotin-cadaverin, and results were analysed by SDS-PAGE/western blotting. The biotinylated scFv could be detected with streptavidin-HRP (MW 28 kDa). A degradation product with lower molecular weight was also detected. The modified peptide could be identified after tryptic digest (Table 1).

3. Modification of a Dimeric, Myc-Tagged Affibody with Biotin-Cadaverine and Dansyl-Cadaverin.

Figure 16:
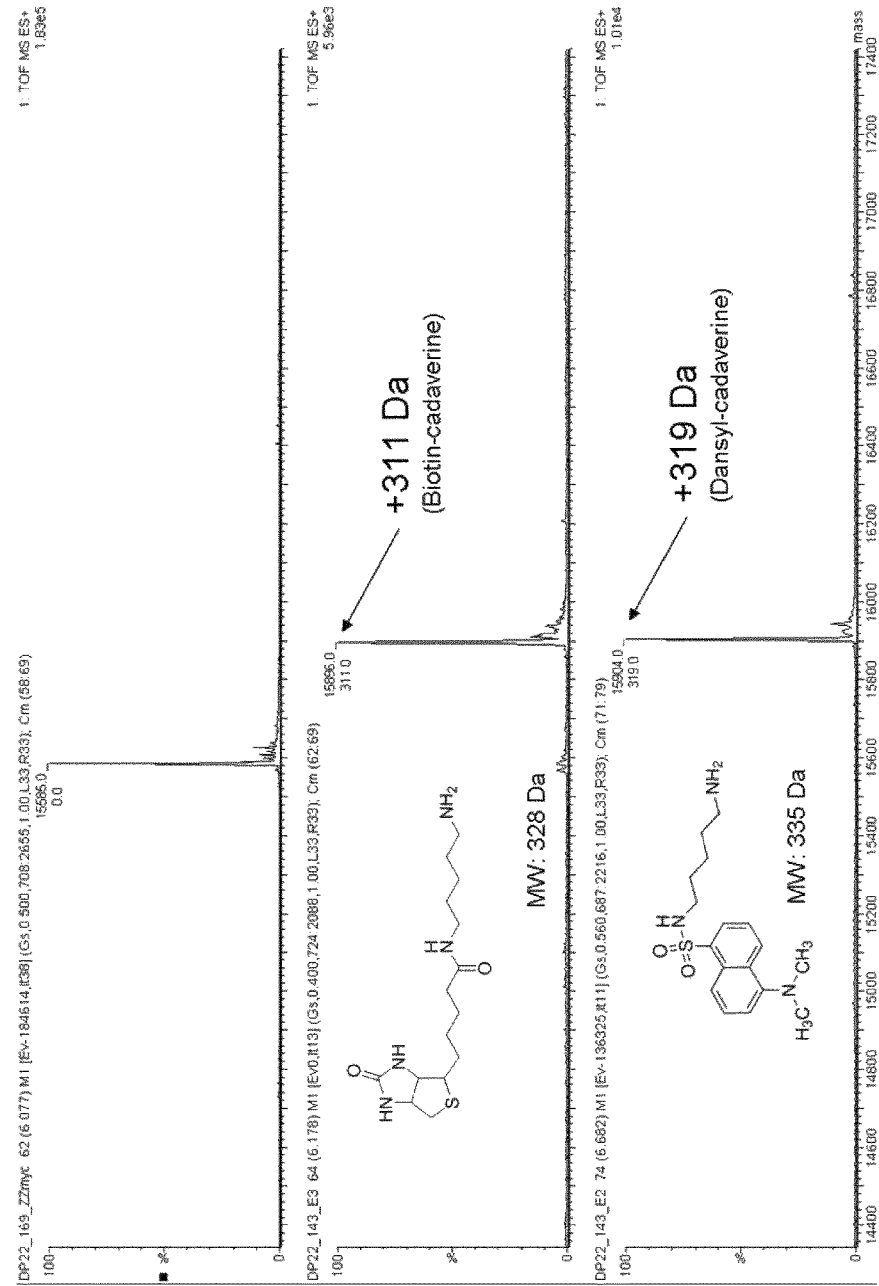
FIG. 16 shows LC-MS analysis of myc-tagged dimeric affibody incubated with MTGase only (top) or MTGase and biotin-cadaverine (middle) or MTGase and dansyl-cadaverine (bottom).

LC-MS analysis showed quantitative modification of myc-tagged dimeric affibody with the substrates biotine-cadaverin and dansyl-cadaverin (FIG. 16). The modified biotinylated peptide was identified by mass spectrometry after tryptic digest (Table 1).

TABLE 1

| Protein | Peptide | Mass (calc) | Mass (found) |
|---|---|---|---|
| scFv | LTVLGAAAEQ*K (SEQ ID NO: 2 | 1410.7904 | 1410.7996 |
| Nano-body | TPTGQGTQVTVSSAAAEQ*K (SEQ ID NO: 3) | 2171.0891 | 2171.0613 |
| Affi-body | VDANSEQ*K (SEQ ID NO: 4) | 1200.5808 | 1200.5671 |

Table 1: identified peptides of scFv, Nanobody and Affibody. Biotin-cadaverinemodified Q residues are indicated by asterisks.

Example 2: Synthesis of Bacterial Transglutaminase Substrates for Two-Step Reactions with and without Spacer Groups Materials and Methods All solvents used for reactions were purchased as anhydrous grade from Acros Organics (puriss., dried over molecular sieves, $H_2O<0.005\%$) and were used without further purification unless otherwise stated. Solvents for extractions, column chromatography and thin layer chromatography (TLC) were purchased as commercial grade. All non aqueous reactions were performed under an argon atmosphere using flame-dried glassware and standard syringe/septa techniques. Commercially available reagents were used without further purification. In general, reactions were magnetically stirred and monitored by TLC performed on Merck TLC glass sheets (silica gel 60 $F_{254}$). Spots were visualized with UV light (λ=254 nm) or by staining with anisaldehyde solution or $KMnO_4$ solution and subsequent heating. Chromatographic purification of products was performed using Fluka silica gel 60 for preparative column chromatography.

Nuclear magnetic resonance (NMR) spectra were recorded in $CDCl_3$, $CD_3OD$ or $D_2O$ either on a Bruker Av-400 or a Bruker Av-500 spectrometer at room temperature. The measured chemical shifts are reported in δ (ppm) and the residual signal of the solvent was used as the internal standard ($CDCl_3$ $^1H$: δ=7.26 ppm, $^{13}C$: δ=77.0 ppm, $CD_3OD$ $^1H$: δ=3.31 ppm, $^{13}C$: δ=49.1 ppm, $D_2O$ $^1H$: δ=4.81 ppm). All $^{13}C$ NMR spectra were measured with complete proton decoupling. Data of NMR spectra are reported as follows: s=singlet, d=doublet, t=triplet, m=multiplet, dd=doublet of doublets, dt=doublet of triplets, br=broad signal. The coupling constant J is reported in Hertz (Hz). High resolution mass spectrometry (HRMS) was performed on a Bruker Daltonics maxis ESI-QTOF or a Varian HiResMALDI instrument.

The analytical and preparative HPLC system used was a Merck-Hitachi D-7000 system. The columns used for chromatography were either an Ultimate XB-C18 (4.6×150 mm, 3 µm) or an Xbridge C18 (4.6×150 mm, 5 µm) for analytical separations operated with a flow of 1 ml/min. For preparative purifications, either an Ultimate XB-C18 (21.2×150 mm, 5 µm) or an Xbridge C18 (10×150 mm, 5 µm) column was used operated with a flow of 15 ml/min and 4 ml/min respectively.

Figure 17:
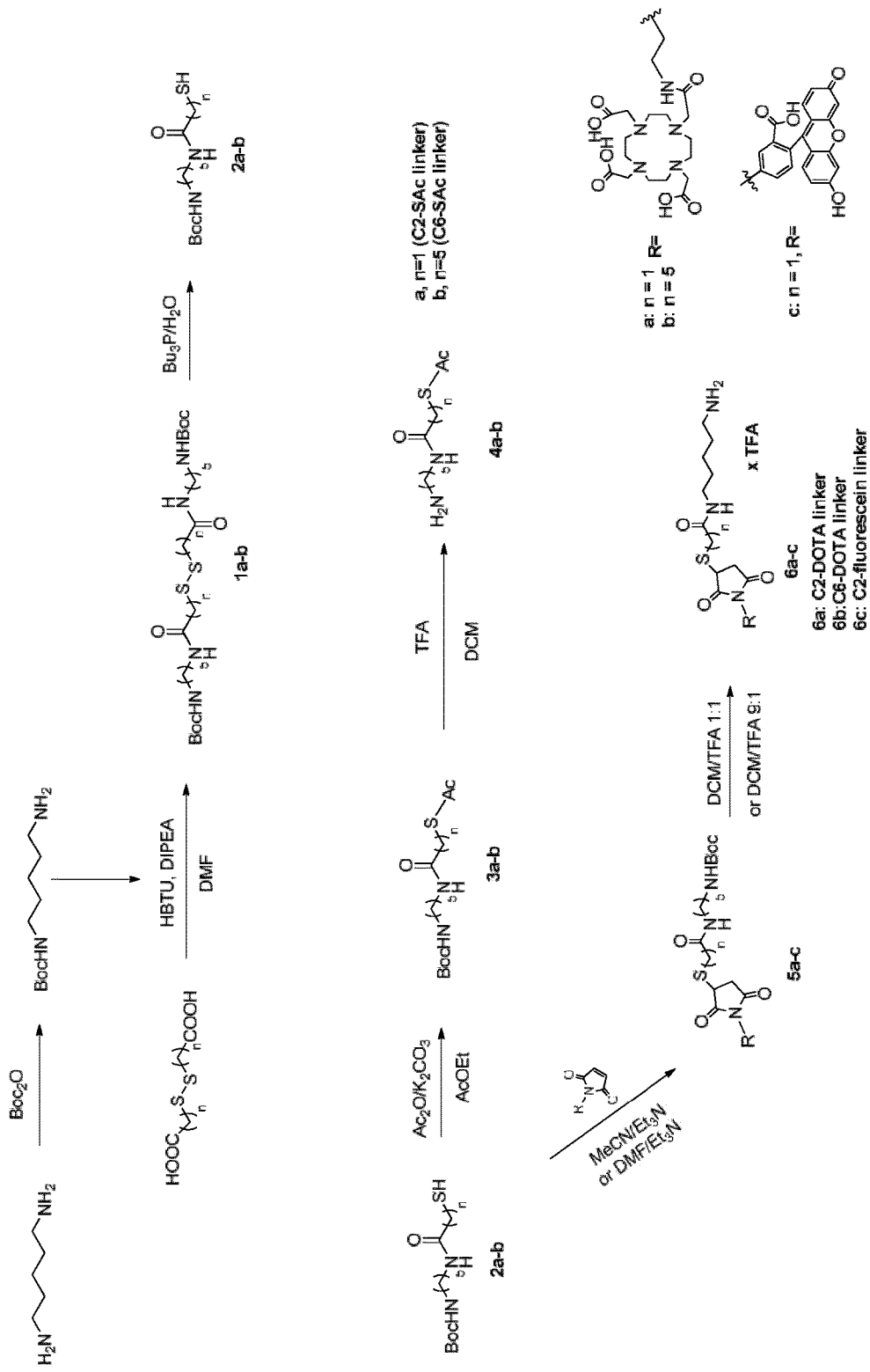
FIG. 17 shows a scheme for preparing S-acetyl-protected cadaverin linkers of different lengths (either n=1 or 5 carbons) as well as a short thiol linker coupled to maleimide-DOTA.
Figure 18A:
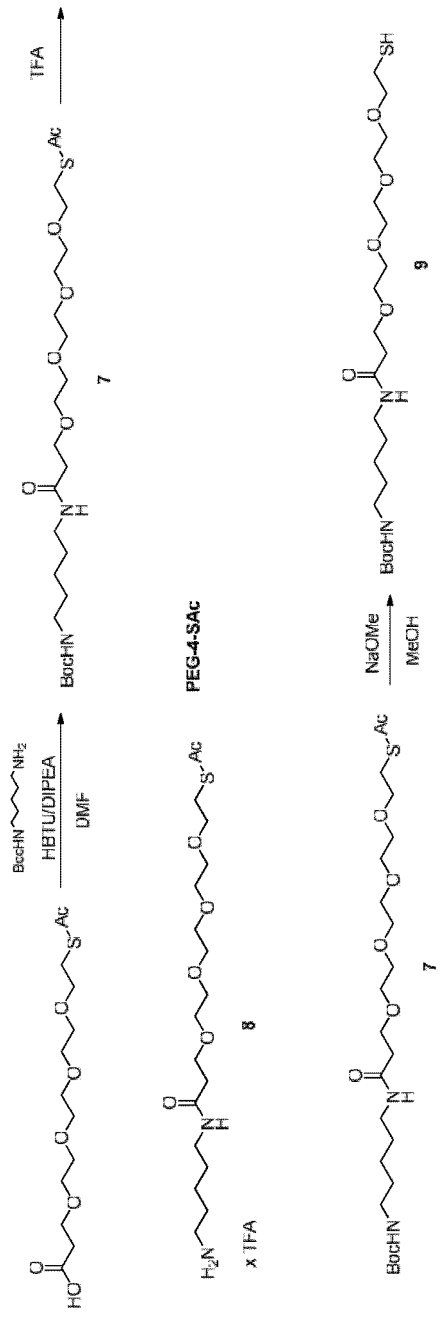
FIGS. 18A, 18B and 18C show schemes for preparing linkers.

Compounds 1-6 and reaction schemes are shown in FIG. 17. Compounds 7-9 and reaction schemes are shown in FIG. 18A. For Compounds 10-13 and reaction schemes, see FIG. 18B.

di-tert-butyl (((2,2'-disulfanediylbis(acetyl))bis (azanediyl))bis(pentane-5,1-diyl))dicarbamate (1a)

In a solution of 2,2'-disulfanediyldiacetic acid (160 mg, 0.878 mmol), tert-butyl (5-amino-pentyl)carbamate (391 mg, 1.932 mmol) and DIPEA (920 µl, 5.27 mmol) in DMF (4.9 ml), HBTU (1.33 g, 3.51 mmol) was added portionwise at room temperature. After stirring for 5 hours, the brownish solution was diluted with ethyl acetate (80 ml) and washed with water (3×30 ml) and brine (1×30 ml). The organic layer was dried under sodium sulfate, filtered and evaporated to dryness. The crude was purified by flash column chromatography on silica using CHCl$_3$/EtOH 95:5 to yield 420 mg (87%) of a yellow oil which solidified upon standing at room temperature. $^1$H NMR (400 MHz, CDCl$_3$): δ 6.91 (br, 2H), 4.68 (br, 2H), 3.44 (s, 4H), 3.29 (dt, J$_1$=7.2 Hz, J$_2$=6.8 Hz, 4H), 3.10 (dt, J$_1$=7.7 Hz, J$_2$=6.3 Hz, 4H), 1.64-1.31 (m, 30H). $^{13}$C NMR (100 MHz, CDCl$_3$): δ 168.5, 156.1, 79.1, 42.6, 40.2, 39.8, 29.7, 28.8, 28.4, 23.9. ESI-QTOF MS m/z calculated for C$_{24}$H$_{46}$N$_4$O$_6$S$_2$ [M+H]$^+$ 551.2932, measured 551.2921 di-tert-butyl(((6,6'-disulfanediylbis(hexanoyl))bis (azanediyl))bis(pentane-5,1-diyl))dicarbamate (1b)

In a solution of 6,6'-disulfanediyldihexanoic acid (250 mg, 0.849 mmol), tert-butyl (5-amino-pentyl)carbamate (412 mg, 2.038 mmol) and DIPEA (0.890 ml, 5.09 mmol) in DMF (4.7 ml), HBTU (1.29 g, 3.40 mmol) was added portionwise at room temperature. After stirring for 20 hours, the yellowish reaction mixture was diluted with ethyl acetate (70 ml) and washed with cold HCl 0.1N (3×50 ml), NaHCO$_3$ (sat) (1×50 ml) water (1×50 ml) and brine (1×50 ml). The organic layer was dried under sodium sulfate, filtered and evaporated to dryness. The crude was purified by flash column chromatography on silica using CHCl$_3$/EtOH 95:5 to yield 525 mg (93%) of compound as a yellow sticky solid. $^1$H NMR (400 MHz, CDCl$_3$): δ 5.87 (br, 2H), 4.64 (br, 2H), 3.22 (dt, J$_1$=7.3 Hz, J$_2$=6.8 Hz, 4H), 3.09 (dt, J$_1$=8.1 Hz, J$_2$=6.7 Hz, 4H), 2.65 (t, J=7.2 Hz, 4H), 2.16 (t, J=7.2 Hz, 4H), 1.73-1.59 (m, 8H), 1.55-1.45 (m, 8H), 1.42 (s, 18H), 1.37-1.28 (m, 4H). $^{13}$C NMR (100 MHz, CDCl$_3$): δ 172.9, 156.1, 79.0, 40.2, 39.2, 38.8, 36.5, 29.7, 29.1, 28.8, 28.4, 28.0, 25.3, 23.9. ESI-QTOF MS m/z calculated for C$_{32}$H$_{62}$N$_4$O$_6$S$_2$ [M+H]$^+$ 663.4184, measured 663.4185.

tert-butyl (5-(2-mercaptoacetamido)pentyl)carbamate (2a)

To a solution of Di-tert-butyl(((2,2'-disulfanediylbis (acetyl))bis(azanediyl))bis(pentane-5,1-diyl))di-carbamate (390 mg, 0.478 mmol) in a mixture of tetrahydrofuran (7 ml) and water (0.74 ml), tributylphosphine (528 mg, 2.48 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with CHCl$_3$/EtOH 95:5 to yield a slightly yellow clear oil. The product was re-purified with flash column chromatography with hexane/ethyl acetate 2:8 to remove oxidized tributylphosphine byproducts. Final yield was 180 mg (91%) of product as a colorless oil which solidified to a white solid after storage at −25° C. $^1$H NMR (400 MHz, CDCl$_3$): δ 6.73 (br, 1H), 4.57 (br, 1H), 3.28 (dt, J$_1$=7.6 Hz, J$_2$=6.9 Hz, 2H), 3.23 (d, J=9.0 Hz, 2H), 3.11 (dt, J$_1$=8.1 Hz, J$_2$=6.6 Hz, 2H), 1.87 (t, $^3$J=9.0 Hz, 1H), 1.61-1.47 (m, 4H), 1.43 (s, 9H), 1.40-1.30 (m, 2H). $^{13}$C NMR (100 MHz, CDCl$_3$): δ 169.1, 156.1, 79.1, 40.2, 39.7, 29.7, 29.0, 28.4, 28.3, 23.9. ESI-QTOF MS m/z calculated for C$_{12}$H$_{24}$N$_2$O$_3$S [M+Na]$^+$299.1400, measured 299.1408.

tert-butyl (5-(6-mercaptohexanamido)pentyl)carbamate (2b)

To a solution of di-tert-butyl((((6,6'-disulfanediylbis (hexanoyl))bis(azanediyl))bis(pentane-5,1-diyl))di-carbamate (196 mg, 0.296 mmol) in a mixture of tetrahydrofuran (3 ml) and water (0.31 ml, 17.21 mmol), tributylphosphine (272 µl, 1.035 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with chloroform/ ethanol 95:5 to yield a slightly yellow clear oil. NMR revealed that the compound was contaminated with tributylphosphine oxidized byproducts so the crude was purified again with flash column chromatography with hexane/ethyl acetate 2:8 to yield 180 mg (91%) of product as a colorless oil which solidified after storage at −25° C. $^1$H NMR (400 MHz, CDCl$_3$): δ 5.88 (br, 1H), 4.57 (br, 1H), 3.23 (dt, J$_1$=7.3 Hz, J$_2$=6.9 Hz, 2H), 3.09 (dt, J$_1$=7.8 Hz, J$_2$=6.5 Hz, 2H), 2.52 (dt, J$_1$=8.0 Hz, J$_2$=7.6 Hz, 2H), 2.16 (t, J=7.5 Hz, 4H), 1.69-1.57 (m, 4H), 1.56-1.46 (m, 4H), 1.43 (s, 9H), 1.36-1.28 (m, 3H). $^{13}$C NMR (100 MHz, CDCl$_3$): δ 172.8, 156.1, 79.1, 40.2, 39.2, 36.5, 33.6, 29.7, 29.1, 28.4, 27.9, 25.1, 24.4, 23.9. ESI-QTOF MS m/z calculated for C$_{16}$H$_{32}$N$_2$O$_3$S [M+H]$^+$ 333.2206, measured 333.2198.

S-(2-((5-((tert-butoxycarbonyl)amino)pentyl)amino)-2-oxoethyl) ethanethioate (3a)

To a mixture of tert-butyl (5-(2-mercaptoacetamido)pentyl)carbamate (189 mg, 0.684 mmol) and dry potassium carbonate (189 mg, 1.368 mmol) in degassed (freeze-pump-thaw) ethyl acetate (2.7 ml), acetic anhydride (77 mg, 0.821 mmol) was added and the reaction was stirred for 16 h. The reaction was then diluted with ethyl acetate (30 ml), filtered and washed with cold water (1×15 ml) and brine (1×15 ml), dried under sodium sulfate and evaporated to dryness. The crude was purified by flash column chromatography on silica with CHC$_3$/EtOH 96:4 to yield 192 mg (88%) of product as a white solid. $^1$H NMR (400 MHz, CDCl$_3$): δ 6.22 (br, 1H), 4.56 (br, 1H), 3.51 (s, 2H), 3.21 (dt, J$_1$=7.1 Hz, J$_2$=6.9 Hz, 2H), 3.09 (dt, J$_1$=7.6 Hz, J$_2$=6.6 Hz, 2H), 2.40 (s, 3H), 1.54-1.45 (m, 4H), 1.43 (s, 9H), 1.35-1.26 (m, 2H). $^{13}$C NMR (100 MHz, CDCl$_3$): δ 190.5, 168.0, 156.0, 79.1, 40.3, 39.6, 33.1, 30.3, 29.6, 29.0, 28.4, 23.8. ESI-QTOF MS m/z calculated for C$_{14}$H$_{26}$N$_2$O$_4$S [M+Na]$^+$341.1505, measured 341.1506.

S-(6-((5-((tert-butoxycarbonyl)amino)pentyl)amino)-6-oxohexyl) ethanethioate (3b)

To a solution of tert-butyl (5-(6-mercaptohexanamido)pentyl)carbamate (180 mg, 0.541 mmol) and dry potassium carbonate (150 mg, 1.083 mmol) in degassed (freeze-pump-thaw) ethyl acetate (2.2 ml), acetic anhydride (61 µl, 0.650 mmol) was added and the reaction was stirred for 16 h. The reaction was then diluted with ethyl acetate (20 ml), filtered and washed with cold water (1×10 ml) and brine (1×10 ml), dried under sodium sulfate and evaporated to dryness. The crude was purified by flash column chromatography using chloroform/ethanol 96:4 to yield 182 mg (90%) of a white solid. $^1$H NMR (400 MHz, CDCl$_3$): δ 5.68 (br, 1H), 4.61 (br, 1H), 3.21 (dt, J$_1$=7.3 Hz, J$_2$=6.9 Hz, 2H), 3.09 (dt, J$_1$=7.7 Hz, J$_2$=6.4 Hz, 2H), 2.83 (t, J=7.2 Hz, 2H), 2.30 (s, 1H), 2.14 (t, J=7.2 Hz, 2H), 1.67-1.44 (m, 8H), 1.42 (s, 9H), 1.40-1.27 (m, 4H). $^{13}$C NMR (100 MHz, CDCl$_3$): δ 196.0, 172.8, 156.1, 79.3, 40.2, 39.2, 36.4, 30.6, 29.7, 29.2, 29.1, 28.8, 28.4, 28.3, 25.1, 23.9. ESI-QTOF MS m/z calculated for C$_{18}$H$_{34}$N$_2$O$_4$S [M+H]$^+$ 375.2312, measured 375.2312

S-(2-((5-aminopentyl)amino)-2-oxoethyl) ethanethioate (4a) (C2-SAc linker)

To a solution of S-(2-((5-((tert-butoxycarbonyl)amino)pentyl)amino)-2-oxoethyl)ethanethioate (189 mg, 0.594 mmol) in dichloromethane (7.9 ml), trifluoroacetic acid (0.92 ml, 11.87 mmol) was added dropwise at 0° C. After stirring for 10 min, the reaction mixture was allowed to reach room temperature where it was stirred for 1 h. Toluene was then added (20 ml), volatiles were removed under reduced pressure and the residue was dried under high vacuum for 30 min to yield quantitatively a slightly yellow oil which was sufficiently pure when analyzed by NMR. The oil was dissolved in water and lyophilized to give a white solid. $^1$H NMR (400 MHz, CD$_3$OD): 3.60 (s, 2H), 3.20 (t, J=6.9 Hz, 2H), 2.91 (t, J=7.6 Hz, 2H), 2.37 (s, 3H), 1.72-1.61 (m, 2H), 1.59-1.50 (m, 2H), 1.45-1.35 (m, 2H). $^{13}$C NMR (100 MHz, CDCl$_3$): δ 196.3, 170.8, 40.7, 40.4, 33.9, 30.1, 29.9, 28.2, 24.6. ESI-QTOF MS m/z calculated for C$_9$H$_{18}$N$_2$O$_2$S [M+H]$^+$ 219.1162, measured 219.1171.

S-(6-((5-aminopentyl)amino)-6-oxohexyl) ethanethioate (4b) (C6-SAc linker)

To a solution of S-(6-((5-((tert-butoxycarbonyl)amino)pentyl)amino)-6-oxohexyl) ethanethioate (187 mg, 0.5 mmol) in dichloromethane (6.6 ml), trifluoroacetic acid (0.77 ml, 5.34 mmol) was added dropwise at 0° C. After stirring for 10 min, the reaction mixture was allowed to reach room temperature where it was stirred for 1 h. The volatiles were removed under reduced pressure at 30° C. and the residue was azeotroped with toluene and dried under high vacuum for 30 min. Lyophilization yielded a white solid (185 mg) which was sufficiently pure by NMR. $^1$H NMR (400 MHz, CD$_3$OD): δ 3.18 (t, J=7.0 Hz, 2H), 2.92 (t, J=7.8 Hz, 2H), 2.86 (t, J=7.3 Hz, 2H), 2.30 (s, 3H), 2.17 (t, J=7.3 Hz, 2H), 1.72-1.50 (m, 8H), 1.45-1.33 (m, 4H). $^{13}$C NMR (100 MHz, CD$_3$OD): 197.7, 176.2, 40.7, 40.0, 37.0, 30.64, 30.61, 30.0, 29.8, 29.4, 28.3, 26.6, 24.8. ESI-QTOF MS m/z calculated for C$_{13}$H$_{26}$N$_2$O$_2$S [M+H]$^+$ 275.1788, measured 275.1785.

2,2',2''-(10-(2-((2-(3-((2-((5-((tert-butoxycarbonyl)amino)pentyl)amino)-2-oxoethyl)thio)-2,5-dioxopyrrolidin-1-yl)ethyl)amino)-2-oxoethyl)-1,4,7,10-tetraazacyclododecane-1,4,7-triyl)triacetic acid (5a)

DOTA-maleimide (25 mg, 0.032 mmol) was suspended in acetonitrile (1 ml) and triethylamine was added (22.59 µl, 0.162 mmol) and after 5 min of stirring, a clear colorless solution was formed. A solution of tert-butyl (5-(2-mercaptoacetamido)pentyl)-carbamate (10.54 mg, 0.038 mmol) in 0.5 ml acetonitrile was then added and the reaction was stirred for 1 h at which point HPLC confirmed complete consumption of starting material. The solvent system used for reaction monitoring is as follows: water/0.1% TFA (solvent A), acetonitrile (solvent B); 0-5 min: 0% B, 5-20 min: 0-50% B, 20-25 min: 50% B, 25-30 min 50-0% B; UV=214 nm; t$_R$=18.3 min. The reaction was then diluted with 3 ml water and was purified by preparative HPLC with the following solvent system: water/0.1% TFA (solvent A), acetonitrile (solvent B); 0-5 min: 0% B, 5-20 min: 0-50% B. The product eluted approximately at 17 min; XB-C18 column; UV=214 nm. The product was obtained as a white solid after lyophilization (19.7 mg, 77% yield). ESI-MS m/z calculated for C$_{34}$H$_{58}$N$_8$O$_{12}$S [M+H]$^+$ 803.39, measured 803.40.

2,2',2''-(1-(2-((2-(3-((6-((5-((tert-butoxycarbonyl)amino)pentyl)amino)-6-oxohexyl)thio)-2,5-dioxopyrrolidin-1-yl)ethyl)amino)-2-oxoethyl)-1,4,7,10-tetraazacyclododecane-1,4,7-triyl)triacetic acid (5b)

To a solution of DOTA-maleimide (80 mg, 0.102 mmol) and triethylamine (52.5 mg, 0.519 mmol) in acetonitrile (3.5 ml) was added a solution of tert-butyl(5-(6-mercaptohexanamido)pentyl)carbamate (40.6 mg, 0.122 mmol) in acetonitrile (1.5 ml) and the reaction mixture was stirred for 6 h at room temperature. Approximately half of the solvent was then removed under reduced pressure, water was added (3 ml) and the mixture was purified with preparative RP HPLC with the following solvent system: water/0.1% TFA (solvent A), acetonitrile (solvent B); 0-5 min: 0% B, 5-20 min: 0-50% B; t$_R$=17.4 min; UV=214 nm; XB-C18 column. The product was obtained as a white solid after lyophilization (58 mg, 57% yield). ESI-MS m/z calculated for C$_{38}$H$_{66}$N$_8$O$_{12}$S [M+H]$^+$ 859.46, measured 859.39.

5-(3-((2-((5-((tert-butoxycarbonyl)amino)pentyl)amino)-2-oxoethyl)thio)-2,5-dioxopyrrolidin-1-yl)-2-(6-hydroxy-3-oxo-3H-xanthen-9-yl)benzoic acid (5c)

A solution of tert-butyl(5-(2-mercaptoacetamido)pentyl)carbamate (14.22 mg, 0.051 mmol) in DMF (0.3 ml) was added to a solution of 5-(2,5-dioxo-2,5-dihydro-1H-pyrrol-1-yl)-2-(6-hydroxy-3-oxo-3H-xanthen-9-yl)benzoic acid (18.32 mg, 0.043 mmol) and triethylamine (4.29 µmol) and the clear yellow solution was stirred for 3 h at room temperature. After this time, the reaction was diluted with water (3 ml) and purified with preparative RP HPLC with the following solvent system: water/0.1% HCOOH (solvent A), acetonitrile (solvent B); 0-5 min: 30% B, 5-20 min: 30-80% B; UV=254 nm; t$_R$=15.4 min; XB-C18 column. The product was obtained as a bright yellow solid after lyophilization (22 mg, 73% yield). ESI-MS m/z calculated for C$_{36}$H$_{37}$N$_3$O$_{10}$S [M+H]$^+$ 704.23, measured 704.05.

2,2',2''-(10-(2-((2-(3-((2-((5-aminopentyl)amino)-2-oxoethyl)thio)-2,5-dioxopyrrolidin-1-yl)ethyl)amino)-2-oxoethyl)-1,4,7,10-tetraazacyclododecane-1,4,7-triyl)triacetic acid (6a) (C2-DOTA linker)

2,2',2''-(10-(2-((2-(3-((2-((5-((tert-butoxycarbonyl)amino)pentyl)amino)-2-oxoethyl)thio)-2,5-dioxo-pyrrolidin-1-yl)ethyl)amino)-2-oxoethyl)-1,4,7,10-tetraazacyclododecane-1,4,7-triyl)triacetic acid (18 mg, 0.022 mmol) was dissolved in a mixture of dichloromethane/TFA 1:1 (2.7 ml) at 0° C. The reaction mixture was stirred for 10 min at this temperature and was then allowed to reach room temperature where it was stirred for 1 h at which point HPLC confirmed complete consumption of the starting material. The volatiles were removed under reduced pressure at 20° C. and the crude was dried under high vacuum for 30 min. The residue was dissolved in 1 ml water and was purified with preparative HPLC to provide 12.7 mg (81%) of a white solid after lyophilization. The solvent systems that were used were the same as in the case of 5a ($t_R$=12.8 min and $t_R$=11 6 min for analytical and preparative HPLC respectively). $^1$H NMR (500 MHz, $D_2O$): δ 4.26-2.89 (br, 28H), 4.07 (dd, $J_1$=9.1 Hz, $J_2$=4.1 Hz, 1H), 3.58 (d, J=15.3 Hz, 1H), 3.42 (d, J=15.3 Hz, 1H), 3.31 (dd, $J_1$=19.1 Hz, $J_2$=9.1 Hz, 1H), 3.22, (t, J=7.1 Hz, 2H), 2.99 (t, J=7.5 Hz, 2H), 2.74 (dd, $J_1$=19.1 Hz, $J_2$=4.1 Hz, 1H), 1.72-1.64 (m, 2H), 1.60-1.52 (m, 2H), 1.44-1.36 (m, 2H). $^{13}$C NMR (100 MHz, $D_2O$): δ 178.8, 178.1, 171.3, 163.0, 162.7, 117.4, 115.1, 54.7, 40.3, 39.4, 39.3, 38.3, 37.1, 35.5, 34.5, 27.7, 27.6, 26.3, 22.9 ESI-MS m/z calculated for $C_{29}H_{51}N_8O_{10}S$ [M+H]$^+$ 703.34, measured 703.32.

2,2',2''-(10-(2-((2-(3-((6-((5-aminopentyl)amino)-6-oxohexyl)thio)-2,5-dioxopyrrolidin-1-yl)ethyl)-amino)-2-oxoethyl)-1,4,7,10-tetraazacyclododecane-1,4,7-triyl)triacetic acid (6b) (C6-DOTA linker)

Compound 5b (45 mg, 0.045 mmol) was dissolved in a mixture of dichloromethane/TFA 1:1 (5.4 ml) at 0° C. and after stirring for 10 min at this temperature, the reaction mixture was allowed to reach room temperature where it was stirred for 2 h. The volatiles when then removed under reduced pressure at 30° C. and traces of TFA were removed with drying under high vacuum for 30 min. The residue was dissolved in water (4 ml) and was purified with preparative RP HPLC using the method described for 5b; $t_R$=13.5 min. ESI-MS m/z calculated for $C_{33}H_{58}N_8O_{10}S$ [M+H]$^+$ 759.41, measured 759.40.

5-(3-((2-((5-aminopentyl)amino)-2-oxoethyl)thio)-2,5-dioxopyrrolidin-1-yl)-2-(6-hydroxy-3-oxo-3H-xanthen-9-yl)benzoic acid (6c) (C2-fluorescein linker)

To an ice cold suspension of 5c (10 mg, 0.014 mmol) in dichloromethane (2 ml), TFA (200 μl, 2.60 mmol) was added dropwise and the clear bright yellow solution was stirred for 10 min at 0° C. for 10 min before allowing it to reach room temperature where it was stirred for 40 min. Toluene was then added and the volatiles were removed under reduced pressure. The crude was purified with semi-preparative RP HPLC with the following system: water/0.1% TFA (solvent A), acetonitrile (solvent B); 0-3 min: 5% B, 3-10 min: 5-25% B, 10-20 min: 25% B; UV=254 nm; $t_R$=15.3 min; Xbridge column. The product was obtained as a bright yellow solid after lyophilization (6.7 mg, 78% yield). ESI-MS m/z calculated for $C_{31}H_{29}N_3O_8S$ [M+H]$^+$ 604.18, measured 604.04.

Synthesis of PEG Linkers

For Compounds 7-9 and reaction schemes, see FIG. 18A.

S-(2,2-dimethyl-4,12-dioxo-3,15,18,21,24-pentaoxa-5,11-diazahexacosan-26-yl) ethanethioate (7)

HBTU (421 mg, 1.11 mmol) was slowly added to a solution of 2-oxo-6,9,12,15-tetraoxa-3-thiaocta-decan-18-oic acid (300 mg, 0.925 mmol) and DIPEA (0.32 ml, 1.85 mmol) in DMF (4.5 ml) and the resulting solution was stirred for 15 min. A solution of tert-butyl(5-aminopentyl)carbamate (225 mg, 1.11 mmol) in DMF (0.6 ml) was then added dropwise and the reaction was stirred for 14 h. The reaction was then diluted with 60 ml ethyl acetate and was washed with water (2×25 ml) and brine (1×25 ml). The organic layer was dried under sodium sulfate, filtered and evaporated under reduced pressure. The crude was purified by flash column chromatography on silica using chloroform/ethanol 95:5 to afford 380 mg (81%) of product as a slight yellow oil. $^1$H NMR (400 MHz, CDCl$_3$): δ 6.51 (br, 1H), 4.66 (br, 1H), 3.70 (t, J=5.8 Hz, 2H), 3.65-3.59 (m, 12H), 3.57 (t, J=6.6 Hz, 2H), 3.21 (dt, $J_1$=7.3 Hz, $J_2$=6.9 Hz, 2H), 3.12-3.02 (m, 4H), 2.44 (t, J=5.8, 2H), 2.31 (s, 3H), 1.53-1.43 (m, 4H), 1.41 (s, 9H), 1.36-1.27 (m, 2H). $^{13}$C NMR (100 MHz, CDCl$_3$): δ 195.4, 171.5, 156.0, 78.9, 70.6, 70.5, 70.3, 70.2, 70.1, 69.7, 67.3, 40.3, 39.0, 36.9, 30.5, 29.6, 29.2, 28.7, 28.4, 24.0. ESI-QTOF MS m/z calculated for $C_{23}H_{44}N_2O_8S$ [M+H]$^+$ 509.2891, measured 509.2884

S-(21-amino-15-oxo-3,6,9,12-tetraoxa-16-azahenicosyl)ethanethioate (8) (PEG-4-SAc linker)

To an ice cold solution of S-(2,2-dimethyl-4,12-dioxo-3,15,18,21,24-pentaoxa-5,11-diazahexacosan-26-yl) ethanethioate (370 mg, 0.73 mmol) in dichloromethane (9.7 ml) was added trifluoroacetic acid (1.1 ml, 14.55 mmol). After stirring for 10 min, the reaction mixture was allowed to reach room temperature and stirred for 2 h. The volatiles were then removed under reduced pressure, followed by drying under high vacuum. A light yellow oil resulted which was sufficiently pure as revealed by NMR (quantitative yield). $^1$H NMR (400 MHz, CDCl$_3$): δ 7.79 (br, 1H), 7.23 (br, 3H), 2.33 (t, J=5.3 Hz, 2H), 3.69-3.56 (m, 14H), 3.31 (dt, $J_1$=7.5 Hz, $J_2$=6.1 Hz, 2H), 3.06 (t, J=6.7 Hz, 2H), 3.03-2.92 (m, 2H), 2.58 (t, J=5.3 Hz, 2H), 2.32 (s, 3H), 1.77-1.65 (m, 2H), 1.64-1.51 (m, 2H), 1.49-1.38 (m, 2H). $^{13}$C NMR (100 MHz, CDCl$_3$): δ 195.7, 174.0, 70.2, 69.99, 69.97, 69.9, 69.8, 69.6, 67.2, 40.0, 38.8, 35.8, 30.4, 28.1, 27.2, 26.0, 22.5. ESI-QTOF MS m/z calculated for $C_{18}H_{36}N_2O_6S$ [M+H]$^+$ 409.2367, measured 409.2381

Tert-butyl (1-mercapto-15-oxo-3,6,9,12-tetraoxa-16-azahenicosan-21-yl)carbamate (9)

A solution of sodium methoxide 0.5 M in methanol (1.8 ml, 0.904 mmol) was added dropwise to a solution of 7 (92 mg, 0.181 mmol) in degassed (freeze-pump-thaw) methanol and the reaction was stirred at room temperature for 3 h. After neutralization with Amberlite 120, the solution was filtered and evaporated to dryness. The crude was purified by flash column chromatography on silica using chloroform/ethanol 95:5 to yield a clear colorless oil (75 mg, 89%). $^1$H NMR (400 MHz, CDCl$_3$): δ 6.48 (br, 1H), 4.64 (br, 1H), 3.71 (t, J=5.7 Hz, 2H), 3.66-3.61 (m, 12H), 3.60 (t, J=6.4 Hz, 2H, partially overlapped by the previous multiplet), 3.22 (q, $J_1$≈$J_2$=7.0, 2H), 3.09 (dt, $J_1$=6.4 Hz, $J_2$=7.8 Hz, 2H), 2.68 (td, $J_1$=6.4 Hz, $J_2$=8.2 Hz, 2H), 2.45 (t, J=5.7 Hz, 2H), 1.59 (t, J=8.2 Hz, 1H), 1.55-1.46 (m, 4H), 1.43 (s, 9H), 1.37-1.30 (m, 2H). $^{13}$C NMR (100 MHz, CDCl$_3$): δ 171.5, 156.0, 79.0, 72.8, 70.6, 70.5, 70.3, 70.2, 67.3, 40.3, 39.1, 37.0, 29.6, 29.2, 28.4, 24.2, 24.0

Synthesis of Azide Linkers

Figure 18B:
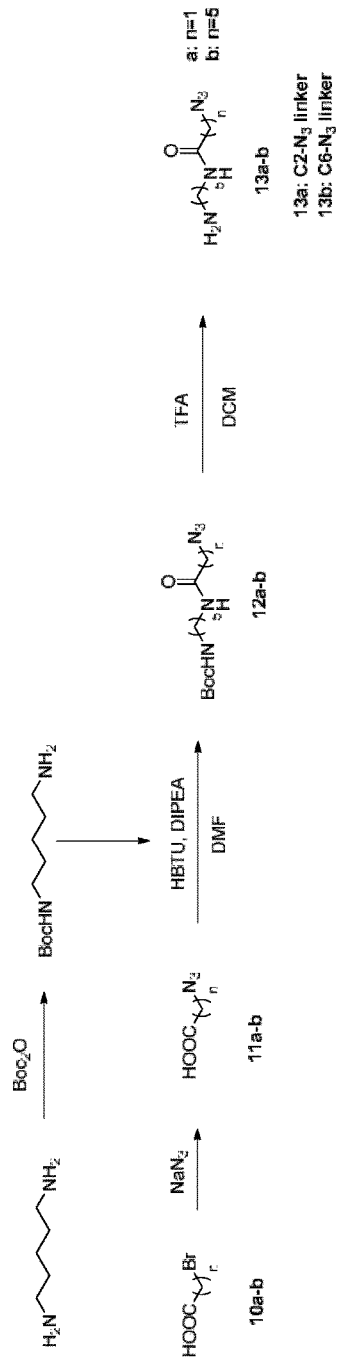

For Compounds 10-13 and reaction schemes, see FIG. 18B. Compounds 11a and 11b were synthesized by following procedures already published in the literature (Brabez N.

et al, Journal of Medicinal Chemistry, 2011, 54(20), 7375-7384 for 11a and Kuil J. et al, Organic and Biomolecular Chemistry, 2009, 7, 4088-4094 for 11b)

tert-butyl (5-(2-azidoacetamido)pentyl)carbamate (12a)

In a solution of 2-azidoacetic acid (50 mg, 0.495 mmol), tert-butyl (5-amino-pentyl)carbamate (120 mg, 0.594 mmol) and DIPEA (128 mg, 0.989 mmol) in DMF (2.7 ml), HBTU (225 mg, 0.594 mmol) was added slowly at room temperature. After stirring for 3 hours, the slight yellow solution was diluted with ethyl acetate (30 ml) and was washed with HCl 0.5 M (3×15 ml) and sat. NaHCO$_3$ (1×15 ml) solutions, water (1×15 ml) and brine (1×15 ml). The organic layer was dried under sodium sulfate, filtered and evaporated to dryness. The crude was purified by flash column chromatography on silica using chloroform/EtOH 95:5 to yield a clear colorless oil (128 mg, 91%). $^1$H NMR (400 MHz, CDCl$_3$): δ 6.35 (br, 1H), 4.55 (br, 1H), 3.97 (s, 2H), 3.28 (dt, J$_1$=7.2 Hz, =6.9 Hz, 2H), 3.11 (dt, J$_1$=7.8 Hz, J$_2$=6.5 Hz, 2H), 1.61-1.47 (m, 4H), 1.43 (s, 9H), 1.40-1.31 (m, 2H). $^{13}$C NMR (100 MHz, CDCl$_3$): δ 166.5, 156.0, 79.1, 52.7, 40.2, 39.2, 29.7, 29.0, 28.4, 23.9.

Tert-butyl (5-(6-azidohexanamido)pentyl)carbamate (12b)

HBTU (290 mg, 0.764 mmol) was slowly added to a solution of 6-azidohexanoic acid (100 mg, 0.636 mmol) and DIPEA (164 mg, 1.273 mmol) in DMF (3 ml) and the resulting solution was stirred for 15 min. A solution of tert-butyl(5-aminopentyl)carbamate (154 mg, 0.764 mmol) in DMF (0.5 ml) was then added dropwise and the reaction was stirred for 3 h. After this time, the reaction mixture was diluted with ethyl acetate (40 ml) and washed with HCl 0.5 M (3×20 ml) and sat. NaHCO$_3$ (1×20 ml) solutions, water (1×20 ml) and brine (1×20 ml). The organic layer was dried under sodium sulfate, filtered and evaporated to dryness. The crude was purified by flash column chromatography on silica using chloroform/EtOH 95:5 to yield a clear colorless oil (189 mg, 87%). $^1$H NMR (400 MHz, CDCl$_3$): δ 5.61 (br, 1H), 4.58 (br, 1H), 3.30-3.20 (m, 4H), 3.10 (dt, J$_1$=8.0 Hz, J$_2$=6.8 Hz, 2H), 2.16 (t, J=7.4 Hz, 2H), 1.56-1.45 (m, 4H), 1.56-1.45 (m, 4H), 1.43 (s, 9H), 1.41-1.29 (m, 4H). $^{13}$C NMR (100 MHz, CDCl$_3$): δ 172.7, 156.1, 79.1, 51.3, 40.2, 39.3, 36.5, 29.8, 29.2, 28.6, 28.4, 26.4, 25.2, 23.9.

N-(5-aminopentyl)-2-azidoacetamide (13a) (C2-N$_3$ linker)

To an ice cold solution of 12a (19.2 mg, 0.067 mmol) in dichloromethane (0.9 ml) was added trifluoroacetic acid (153 mg, 1.346 mmol). After stirring for 10 min, the reaction mixture was allowed to reach room temperature and stirred for 2 h. Toluene (4 ml) was then added and the volatiles were removed under reduced pressure. The crude was azeotroped again with toluene to remove traces of TFA and was then dried under HVP for 3 hours to yield a light yellow oil (quantitative yield) which was sufficiently pure for further use, as revealed by NMR. $^1$H NMR (400 MHz, CD$_3$OD): δ 3.87 (s, 2H), 3.24 (t, J=7.1 Hz, 2H), 2.92 (t, J=7.5 Hz, 2H), 1.72-1.63 (m, 2H), 1.62-1.53 (m, 2H), 1.46-1.36 (m, 2H). $^{13}$C NMR (100 MHz, CD$_3$OD): δ 170.3, 53.1, 40.7, 40.1, 30.0, 28.3, 24.7.

N-(5-aminopentyl)-6-azidohexanamide (13b) (C6-N$_3$ linker)

Compound 13b was synthesized by following a similar procedure as described above for 13a (starting with 22.8 mg, 0.067 mmol of 12b). $^1$H NMR (400 MHz, CD$_3$OD): δ 3.29 (t, J=6.8 Hz, 2H), 3.19 (t, J=7 Hz, 2H), 2.92 (t, J=7.7 Hz, 2H), 2.20 (t, J=7.3 Hz, 2H), 1.73-1.51 (m, 8H), 1.46-1.35 (m, 4H). $^{13}$C NMR (100 MHz, CD$_3$OD): δ 176.2, 52.5, 40.7, 40.0, 37.0, 30.1, 29.8, 28.3, 27.5, 26.7, 24.8.

MMAF-6C Thiol Linker Synthesis

Figure 18C:
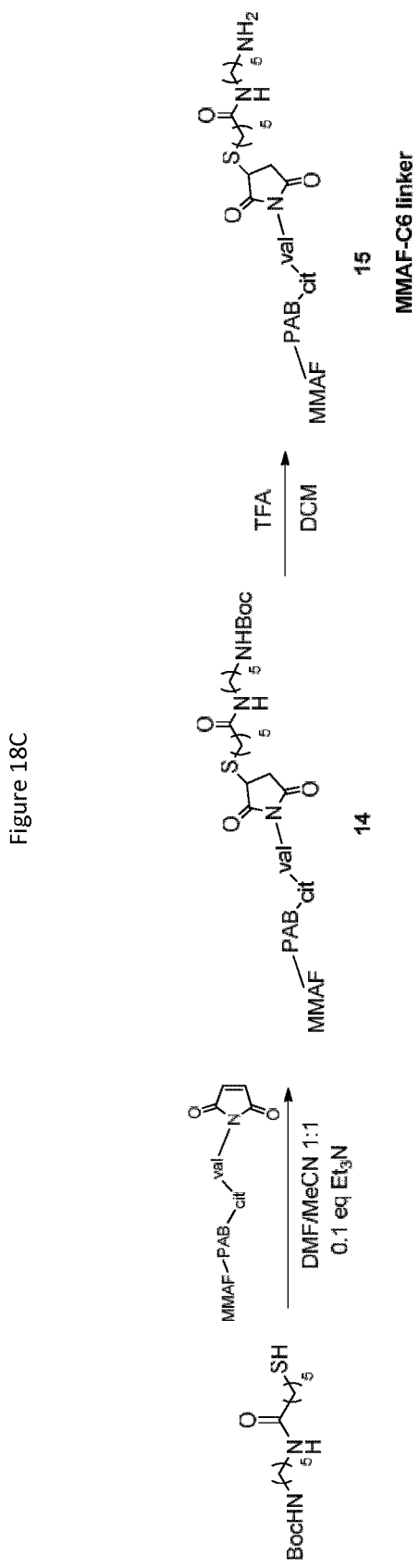

Compounds 14-15 and reaction schemes are shown in FIG. 18C.

maleimide-valine-citrullin-PAB-MMAF+6C thiol linker (Boc protected) (14)

To a solution of maleimide-valine-citrullin-PAB-MMAF (8.8 mg, 6.61 μmol) in DMF (0.6 ml) was added 6.6 μl of a 0.1 M solution of triethylamine in DMF (0.66 μmol Et$_3$N), followed by the dropwise addition of a solution of tert-butyl (5-(6-mercaptohexanamido)pentyl)carbamate (3 mg, 9.02 μmol) in acetonitrile (0.3 ml). The reaction was stirred for 3 h, diluted with water (2 ml) and purified with semi-preparative RP HPLC with the following system: water/50 mM NH$_4$HCO$_3$ (solvent A), acetonitrile (solvent B); 0-5 min: 40% B, 5-20 min: 40-80% B; UV=254 nm; t$_R$=10.3 min; Xbridge column. The product was obtained as a white solid after lyophilization (8.7 mg, 79% yield).

maleimide-valine-citrullin-PAB-MMAF+6C thiol linker (MMAF-6C linker) (15)

Compound 14 (8 mg, 4.81 μm) was dissolved in an ice cold solution of dichloromethane/TFA 95:5 (8 ml). The reaction mixture was allowed to reach room temperature and stirred for 40 min after which time the volatiles were removed under reduced pressure with the addition of toluene. Traces of solvents were removed under high vacuum and the residue was purified by semi-preparative HPLC with the following system: water/50 mM NH$_4$HCO$_3$ (solvent A), acetonitrile (solvent B); 0-5 min: 30% B, 5-20 min: 30-70% B; UV=254 nm; t$_R$=11.7 min; Xbridge column. The product was obtained as a white solid after lyophilization (4.86 mg, 65% yield). ESI-QTOF MS m/z calculated for C$_{79}$H$_{127}$N$_{13}$O$_{17}$5 [M+2H]$^{2+}$ 781.9670, measured 781.9667.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. An antibody lacking an Fc domain selected from the group consisting of a scFv, an affibody, a $V_H$ domain, a $V_L$ domain, a V-NAR domain and a $V_H H$ domain, comprising a TGase recognition tag comprising a functionalized acceptor glutamine residue (Q) of Formula IV, below, $$(Q)\text{-NH---}(C)_n\text{---X-L-}(V\text{---}(Y\text{-}(M)_z)_q)_r \qquad \text{Formula IV}$$

where:
- Q is glutamine residue present in the TGase recognition tag;
- $(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
- n is an integer selected from among the range of 2 to 20;
- X is NH, O, S, absent, or a bond;
- L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
- r is an integer selected from among 1, 2, 3 or 4;
- q is an integer selected from among 1, 2, 3 or 4;
- z is an integer selected from among 1, 2, 3 or 4; and
- V is independently absent, a non-cleavable moiety or a conditionally-cleavable moiety;
- Y is independently absent, a bond or a continuation of a bond, or a spacer system which is comprised of 1 or more spacers;
- M is $((RR')-L'-(V'-(Y'-(Z)_{z'})_{q'})_{r'})$,
  - wherein Z is a moiety-of-interest, optionally a moiety that improves the pharmacokinetic properties, or a therapeutic moiety or a diagnostic moiety,
  - wherein each of L', V', Y', z', q', and r' are as defined as L, V, Y, z, q and r, and
  - wherein RR' is an addition product between a reactive moiety R and a complementary reactive moiety R', wherein R and R' are moieties capable of undergoing a Huisgen 1,3-cycloaddition reaction, wherein one of the R and R' is an azide and the other is a strained cycloalkyene.

2. The antibody of claim 1, wherein Z is an organic compound, having a molecular weight of at least 300 g/mol, 400 g/mol, 500 g/mol, 600 g/mol, 700 g/mol, 800 g/mol, 900 g/mol, 1,000 g/mol or 2,000 g/mol.

3. The antibody of claim 1, wherein Z is a cytotoxic agent.

4. The antibody of claim 1, wherein the TGase recognition tag comprises an amino acid sequence of SEQ ID NO: 1 or a variant thereof comprising 1, 2, 3, 4, 5 or 6 amino acid modifications.

5. The antibody of claim 1, wherein the antibody is selected from an scFv, an affibody, a $V_H$ domain, a $V_L$ domain, a V-NAR domain and a $V_HH$ domain, fused at its N- or C-terminus to a TGase recognition tag comprising an amino acid sequence of SEQ ID NO: 1 or a variant thereof comprising 1, 2, 3, 4, 5 or 6 amino acid modifications.

6. A kit comprising a library of at least 100 antibodies of claim 4.

7. The kit of claim 6, wherein the library is produced from a phage display library.

8. The antibody of claim 1, wherein Z is chemical compound displaying hydrophobic properties.

* * * * *